(12) United States Patent
Van Ostrand et al.

(10) Patent No.: US 11,935,397 B2
(45) Date of Patent: Mar. 19, 2024

(54) ORGANIC AND INORGANIC TEST SYSTEM

(71) Applicant: SIGMASENSE, LLC., Wilmington, DE (US)

(72) Inventors: Daniel Keith Van Ostrand, Leander, TX (US); Richard Stuart Seger, Jr., Belton, TX (US); Gerald Dale Morrison, Redmond, WA (US); Patrick Troy Gray, Cedar Park, TX (US); Phuong Huynh, Fairfax, VA (US); Timothy W. Markison, Mesa, AZ (US); Patricia A. Markison, Phoenix, AZ (US)

(73) Assignee: SIGMASENSE, LLC., Austin, TX (US)

( * ) Notice: Subject to any disclaimer, the term of this patent is extended or adjusted under 35 U.S.C. 154(b) by 750 days.

(21) Appl. No.: 16/730,118

(22) Filed: Dec. 30, 2019

(65) Prior Publication Data

US 2021/0201659 A1 Jul. 1, 2021

(51) Int. Cl.
*G08C 15/02* (2006.01)
*G01D 21/02* (2006.01)
(Continued)

(52) U.S. Cl.
CPC .............. *G08C 15/02* (2013.01); *G01D 21/02* (2013.01); *G01N 27/028* (2013.01); *G01N 33/4836* (2013.01)

(58) Field of Classification Search
CPC ...... G08C 15/02; G01D 21/02; G01N 27/028; G01N 33/4836
See application file for complete search history.

(56) References Cited

U.S. PATENT DOCUMENTS 5,437,178 A 8/1995 Esin et al.
6,218,972 B1 4/2001 Groshong
(Continued)

FOREIGN PATENT DOCUMENTS

CN 104536627 A 4/2015
CN 107771273 A 3/2018
(Continued)

OTHER PUBLICATIONS

Chawla, Ketki, et al. "Integrating impedance-based growth-rate monitoring into a microfluidic cell culture platform for live-cell microscopy." Microsystems & nanoengineering 4.1 (2018): 1-12. (Year: 2018).*

(Continued)

*Primary Examiner* — Robert J Eom
(74) *Attorney, Agent, or Firm* — Garlick & Markison; Patricia M. Healy

(57) ABSTRACT

A test system includes a test container array including a plurality of test containers and a plurality of electrodes integrated into the test container array. The test system further includes a plurality of drive-sense circuits coupled to the plurality of electrodes, where, when enabled, the plurality of drive-sense circuits detect changes in electrical characteristics of the plurality of electrodes. The test system further includes a processing module operably coupled to receive, from the drive-sense circuits, changes in the electrical characteristics of the plurality of electrodes, and interpret the changes in the electrical characteristics of the plurality of electrodes as impedance values representative of electrical characteristics of biological material present in the test container. The test system further includes a communication module operably coupled to communicate the electrical characteristics of the biological material.

11 Claims, 46 Drawing Sheets

(51) Int. Cl.
*G01N 27/02* (2006.01)
*G01N 33/483* (2006.01)

(56) References Cited

U.S. PATENT DOCUMENTS

| | | |
|---|---|---|
| 6,331,274 B1 | 12/2001 | Ackley et al. |
| 6,665,013 B1 | 12/2003 | Fossum et al. |
| 7,476,233 B1 | 1/2009 | Wiener et al. |
| 7,528,755 B2 | 5/2009 | Hammerschmidt |
| 8,031,094 B2 | 10/2011 | Hotelling |
| 8,089,289 B1 | 1/2012 | Kremin et al. |
| 8,279,180 B2 | 10/2012 | Hotelling et al. |
| 8,547,114 B2 | 10/2013 | Kremin |
| 8,625,726 B2 | 1/2014 | Kuan |
| 9,201,547 B2 | 12/2015 | Elias |
| 2003/0052657 A1 | 3/2003 | Koernle et al. |
| 2005/0235758 A1 | 10/2005 | Kowal et al. |
| 2011/0063154 A1 | 3/2011 | Hotelling et al. |
| 2011/0298745 A1 | 12/2011 | Souchkov |
| 2013/0278447 A1 | 10/2013 | Kremin |
| 2014/0346058 A1 | 11/2014 | Robitzki et al. |
| 2014/0377850 A1 | 12/2014 | Handique et al. |
| 2016/0188049 A1 | 6/2016 | Yang et al. |
| 2018/0157354 A1 | 6/2018 | Blondin et al. |
| 2018/0275824 A1 | 9/2018 | Li |
| 2018/0364861 A1 | 12/2018 | Gray |

FOREIGN PATENT DOCUMENTS

| | | |
|---|---|---|
| EP | 2284637 A1 | 2/2011 |
| KR | 101100604 B1 | 12/2011 |

OTHER PUBLICATIONS

Baker; How delta-sigma ADCs work, Part 1; Analog Applications Journal; Oct. 1, 2011; 6 pgs.

Brian Pisani, "Digital Filter Types in Delta-Sigma ADCs", Application Report SBAA230, May 2017, pp. 1-8, Texas Instruments Incorporated, Dallas, Texas.

International Searching Authority; International Search Report and Written Opinion; International Application No. PCT/US2020/063812; dated Mar. 26, 2021; 12 pgs.

European Patent Office; Extended European Search Report; Application No. 19853507.2; dated Jun. 13, 2023; 7 pgs.

\* cited by examiner

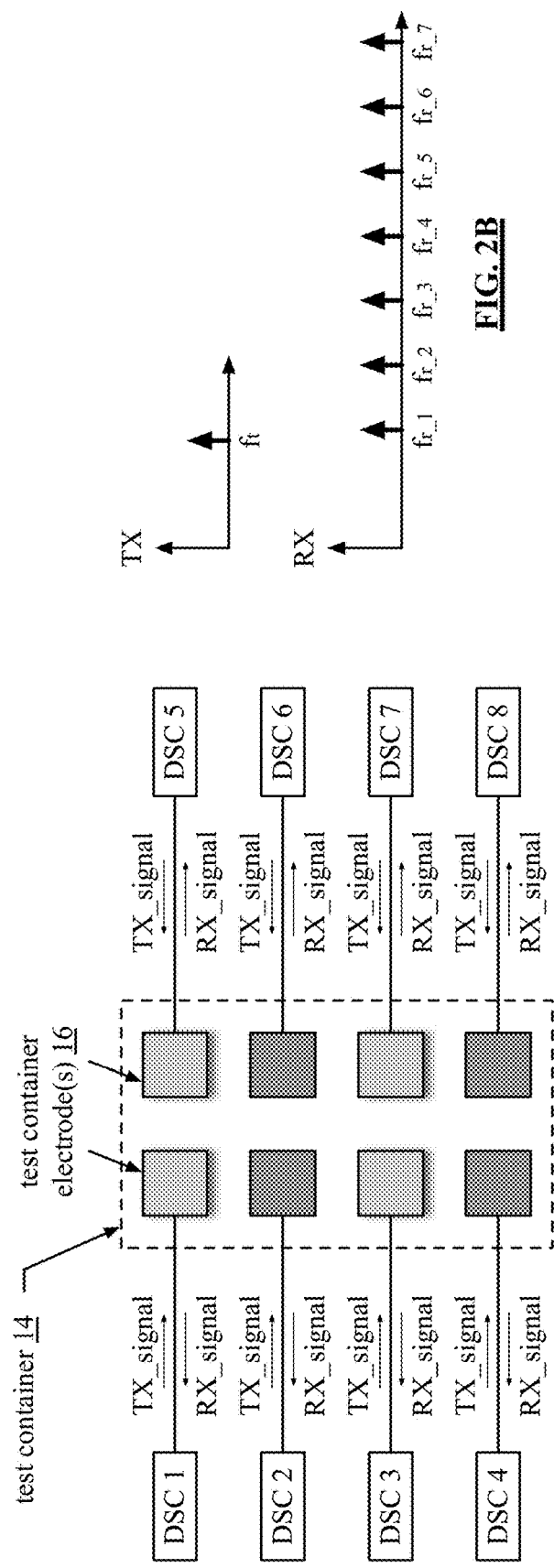
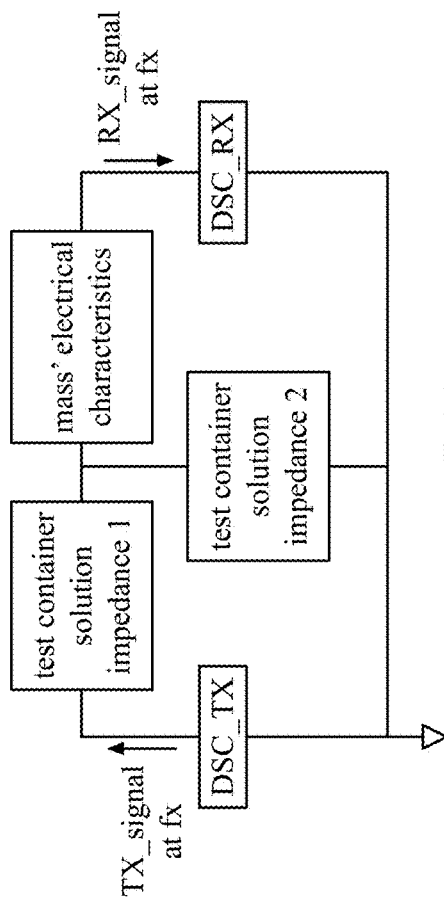

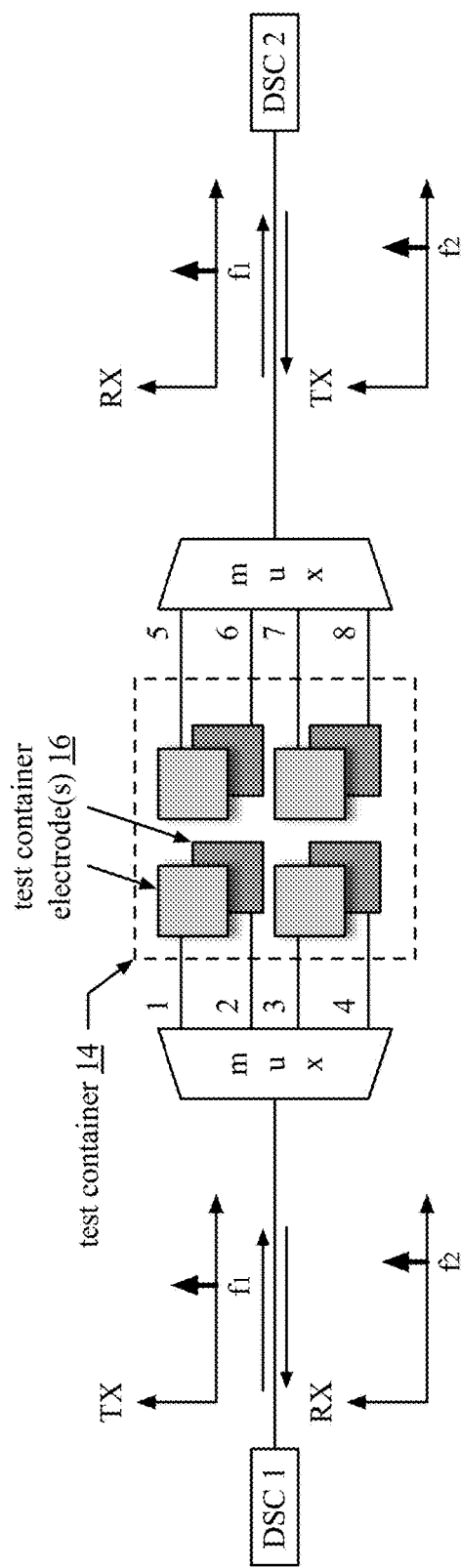

with solution 20 only test container equivalent circuit 106
(solution only)

1st set of impedances of impedance map

2nd set of impedances
of impedance map

| | | | | | | | |
|---|---|---|---|---|---|---|---|
| | 1-2 | 1-3 | 1-4 | 1-5 | 1-6 | (1-7) | 1-8 |
| 2-1 | | 2-3 | 2-4 | 2-5 | 2-6 | 2-7 | 2-8 |
| 3-1 | 3-2 | | 3-4 | 3-5 | 3-6 | 3-7 | 3-8 |
| 4-1 | 4-2 | 4-3 | | 4-5 | 4-6 | 4-7 | 4-8 |
| 5-1 | 5-2 | 5-3 | 5-4 | | 5-6 | 5-7 | 5-8 |
| 6-1 | 6-2 | 6-3 | 6-4 | 6-5 | | 6-7 | 6-8 |
| (7-1) | 7-2 | 7-3 | 7-4 | 7-5 | 7-6 | | 7-8 |
| 8-1 | 8-2 | 8-3 | 8-4 | 8-5 | 8-6 | 8-7 | |

Row labels: 1st set of impedances, 2nd set of impedances, 3rd set of impedances, 4th set of impedances, 5th set of impedances, 6th set of impedances, 7th set of impedances, 8th set of impedances

FIG. 11 test container impedance map
118 (solution 20 only)

with solution 20 and cell 18 test container equivalent circuit 106
(with cell & solution)

impedance 110 = solution (Z_sol) + cell (Z_mass)

1st set of impedances of impedance map 118-1

7th set of impedances of impedance map 118-1

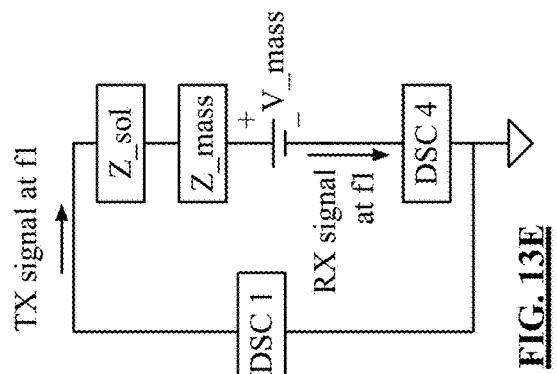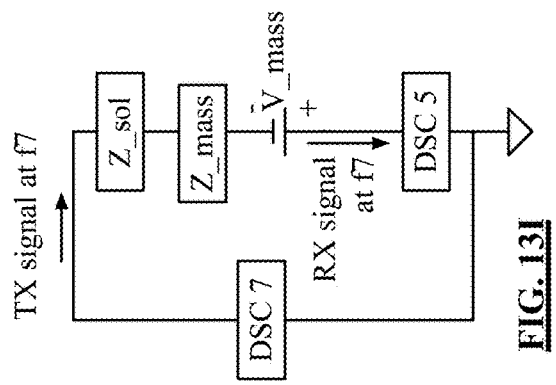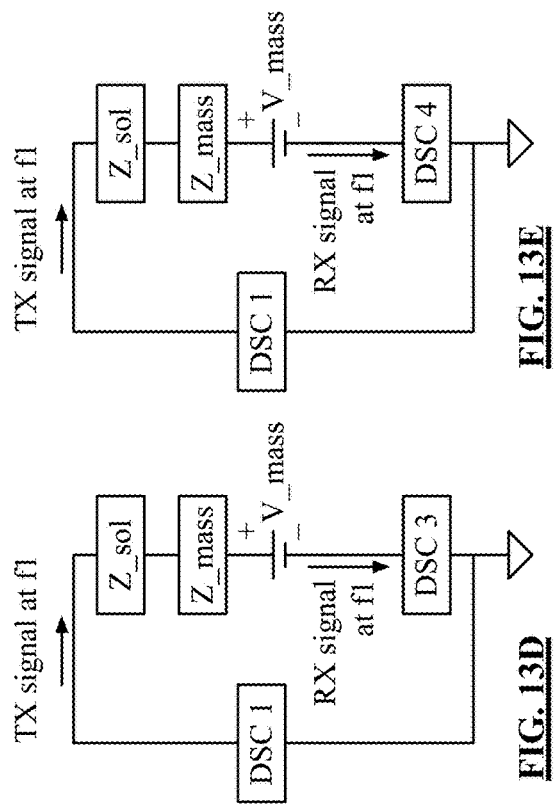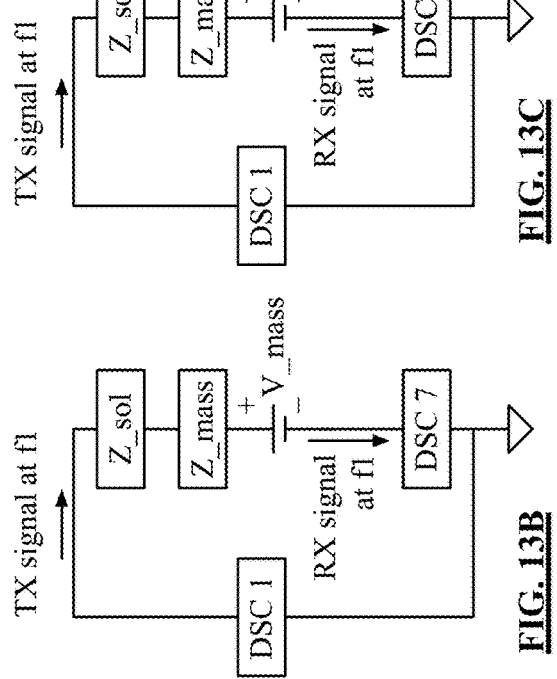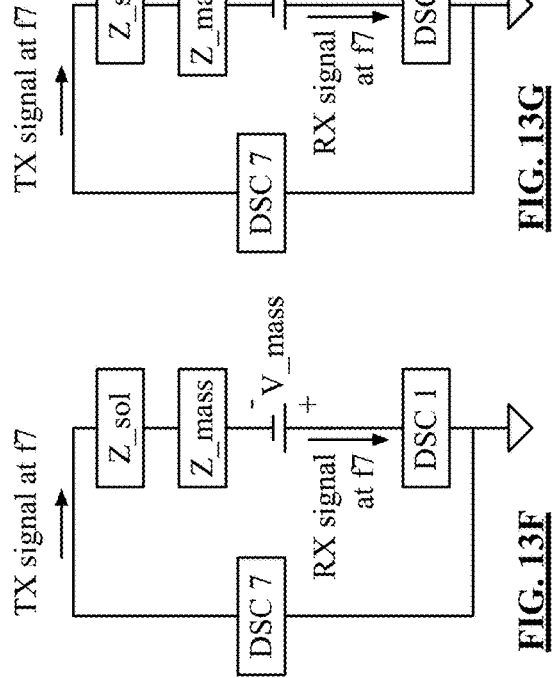

with solution 20 and cell 18
and testing substance 122

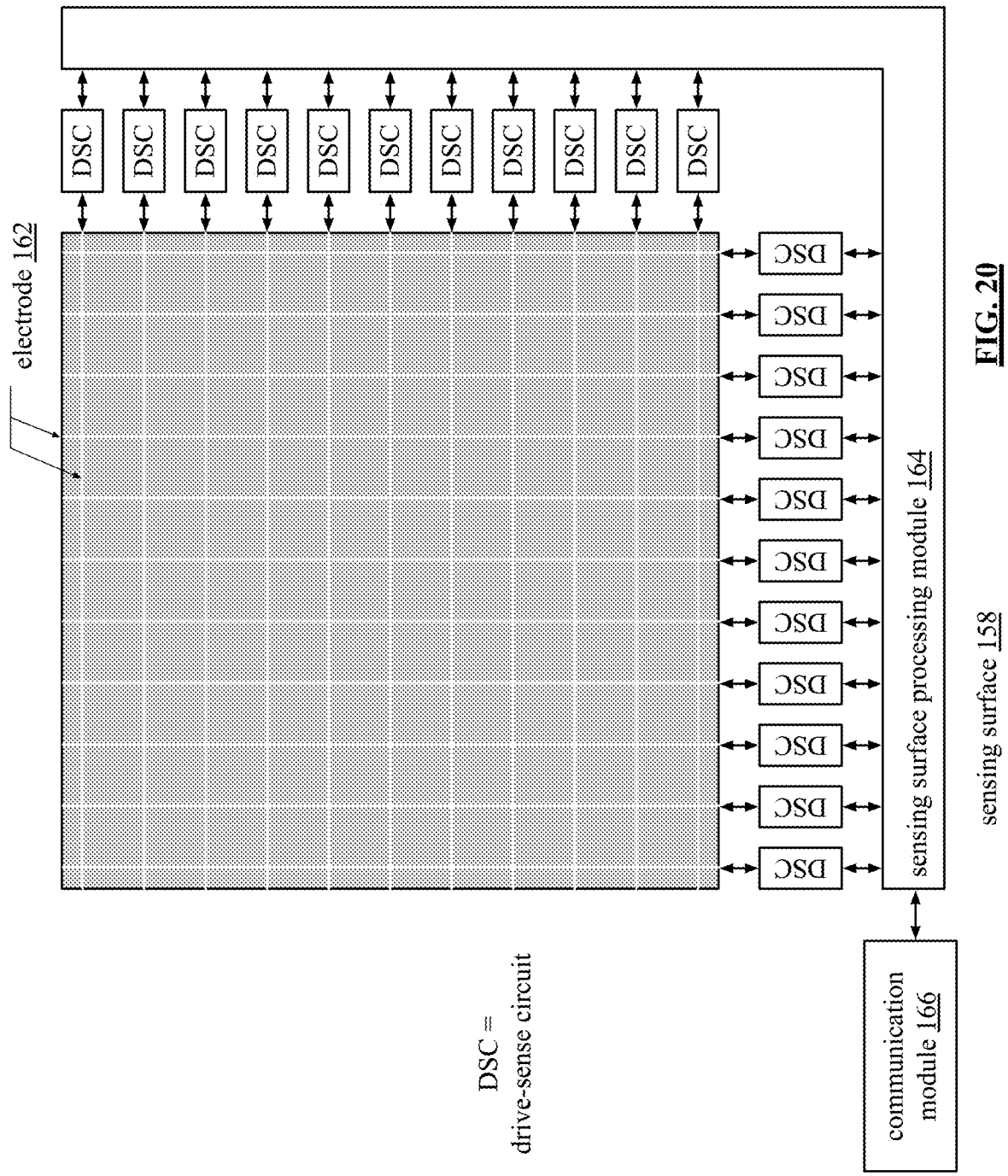

test system 10 test system 10 test system 10

ORGANIC AND INORGANIC TEST SYSTEM

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

Technical Field of the Invention

This invention relates generally to data communication systems and more particularly to sensed data collection and/or communication.

Description of Related Art

Sensors are used in a wide variety of applications ranging from in-home automation, to industrial systems, to health care, to transportation, and so on. For example, sensors are placed in bodies, automobiles, airplanes, boats, ships, trucks, motorcycles, cell phones, televisions, touch-screens, industrial plants, appliances, motors, checkout counters, etc. for the variety of applications.

In general, a sensor converts a physical quantity into an electrical or optical signal. For example, a sensor converts a physical phenomenon, such as a biological condition, a chemical condition, an electric condition, an electromagnetic condition, a temperature, a magnetic condition, mechanical motion (position, velocity, acceleration, force, pressure), an optical condition, and/or a radioactivity condition, into an electrical signal.

A sensor includes a transducer, which functions to convert one form of energy (e.g., force) into another form of energy (e.g., electrical signal). There are a variety of transducers to support the various applications of sensors. For example, a transducer is capacitor, a piezoelectric transducer, a piezoresistive transducer, a thermal transducer, a thermal-couple, a photoconductive transducer such as a photoresistor, a photodiode, and/or phototransistor.

A sensor circuit is coupled to a sensor to provide the sensor with power and to receive the signal representing the physical phenomenon from the sensor. The sensor circuit includes at least three electrical connections to the sensor: one for a power supply; another for a common voltage reference (e.g., ground); and a third for receiving the signal representing the physical phenomenon. The signal representing the physical phenomenon will vary from the power supply voltage to ground as the physical phenomenon changes from one extreme to another (for the range of sensing the physical phenomenon).

The sensor circuits provide the received sensor signals to one or more computing devices for processing. A computing device is known to communicate data, process data, and/or store data. The computing device may be a cellular phone, a laptop, a tablet, a personal computer (PC), a work station, a video game device, a server, and/or a data center that support millions of web searches, stock trades, or on-line purchases every hour.

The computing device processes the sensor signals for a variety of applications. For example, the computing device processes sensor signals to determine temperatures of a variety of items in a refrigerated truck during transit. As another example, the computing device processes the sensor signals to determine a touch on a touch screen. As yet another example, the computing device processes the sensor signals to determine behavior of biological cells.

In vitro study of the behavior of cells is conventionally done using petri dishes, glass slides, or microplates (e.g., flat assay plates with multiple testing wells) as culture substrates and a form of optical analysis such as absorbance, fluorescence intensity, luminescence, time-resolved fluorescence, and/or fluorescence. Chemicals such as drugs and pesticides have different effects on cells such as destruction of cell membrane, prevention of protein synthesis, irreversible binding to receptors, enzymatic reactions, etc. Such effects can cause voltage changes, presence or absence of particular ions or molecules, etc. Dyes sensitive to those changes are applied to cells and different cellular effects are indicated through visual changes (e.g., a level of fluorescence). The dyes adversely affect the cells such that the cells usually die within a few hours. This substantially limit the usefulness of such testing techniques, especially when testing the cells' responses to a variety of stimuli.

BRIEF DESCRIPTION OF THE SEVERAL VIEWS OF THE DRAWING(S)

FIG. 2A is a schematic block diagram of an embodiment of a set of test container electrodes coupled to drive-sense circuits (DSCs) in accordance with the present invention;

FIG. 2B is a diagram of an example of a transmit signal and a receive signal, in the frequency domain, of a drive-sense circuit (DSC) of the embodiment of FIG. 2A in accordance with the present invention;

FIG. 2C is a diagram of an example of a frequency pattern used by the drive-sense circuits (DSCs) of the embodiment of FIG. 2A in accordance with the present invention;

FIG. 2D is a schematic diagram of an example of a generic circuit of a transmit drive-sense circuit (DSC) and a receive DSC of the embodiment of FIG. 2A in accordance with the present invention;

FIG. 3A is a schematic block diagram of another embodiment of a set of test container electrodes coupled to drive-sense circuits (DSCs) in accordance with the present invention;

FIG. 3B is a diagram of an example of a frequency pattern used by the drive-sense circuits (DSCs) of the embodiment of FIG. 3A in accordance with the present invention;

FIG. 11 is a schematic block diagram of a test container impedance map in accordance with the present invention;

FIGS. 13B-13E are schematic block diagrams of equivalent circuits of the embodiment of FIG. 12 with respect to the drive-sense circuit (DSC) 1 as the source of the transmit signal;

FIGS. 13F-13I are schematic block diagrams of equivalent circuits of the embodiment of FIG. 12 with respect to the drive-sense circuit (DSC) 7 as the source of the transmit signal;

FIG. 20 is a schematic block diagram of an embodiment of a sensing surface in accordance with the present invention;

DETAILED DESCRIPTION OF THE INVENTION

Figure 1:
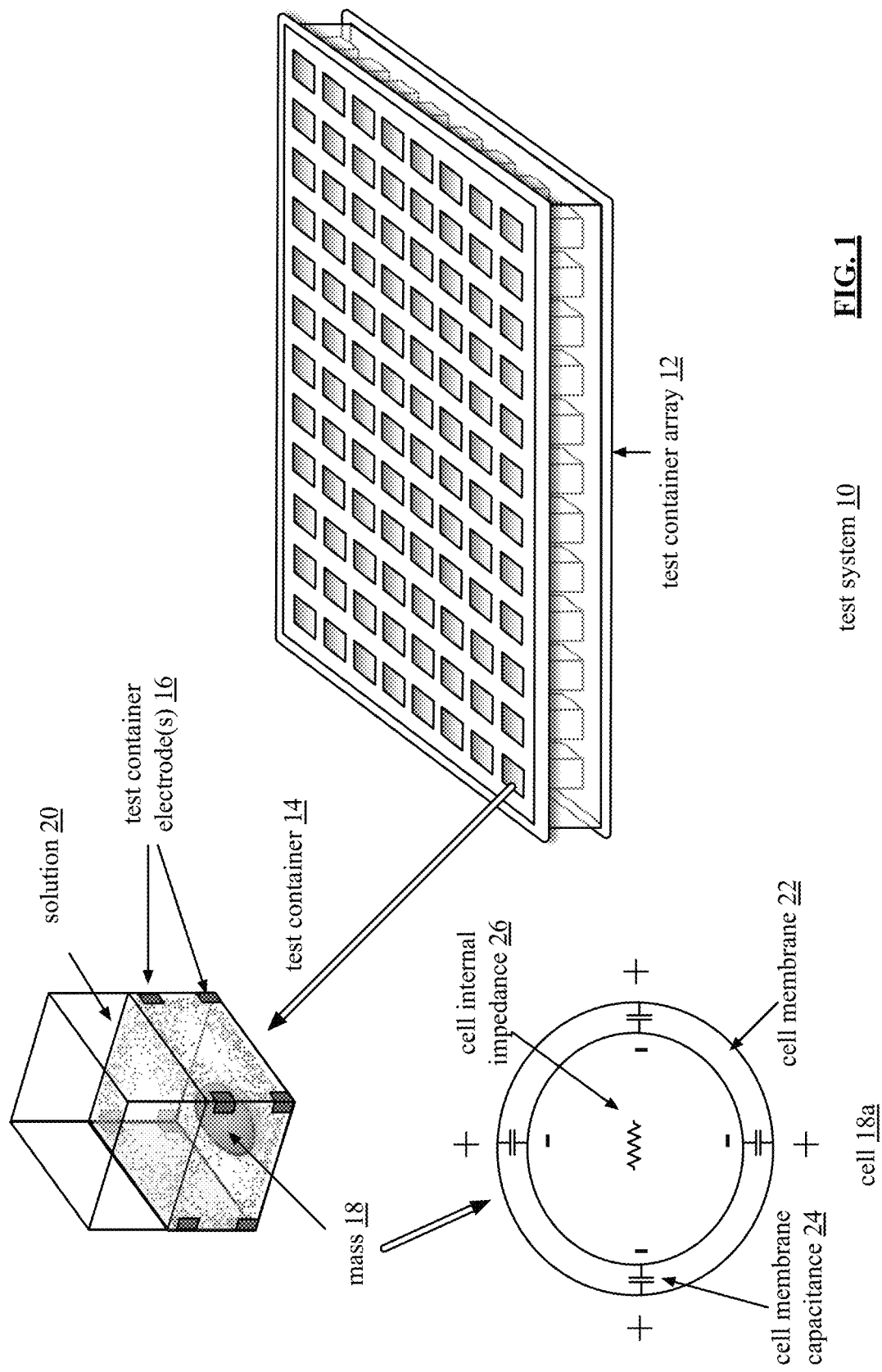
FIG. 1 is a schematic block diagram of an embodiment of a test system in accordance with the present invention.

FIG. 1 is a schematic block diagram of an embodiment of an organic and inorganic test system 10 ("test system') that includes a test container array 12 including a plurality of test containers 14. The test container array 12 may be comprised of a variety of materials such as polystyrene, polypropylene, glass, flexible plastic tape, and quartz, and may be a variety of shapes and sizes. The test container array 12 is shown as a rectangular array of 8×12 cubical test containers 14. The test container array may include more or less test containers 14 than shown and the test containers 14 may be a variety of shapes, depths, and sizes (e.g., cylindrical, rectangular prism, circular, test tube, petri dish, etc.). Each test container 14 includes a set of test container electrodes 16. The set of test container electrodes 16 includes one or more test container electrodes.

The test container electrodes 16 are electric conductors used to monitor electrical characteristics of contents within the test container 14. The test container electrodes 16 are constructed of electrically conductive material (e.g., a conductive metal such as copper, silver, gold, tin, or a non-metallic conductor such as graphite, conductive polymer, etc.). The test container electrodes 16 may be a transparent conductive material, such that optical observations of the testing container 14 are unobstructed. For instance, an electrode is constructed from one or more of: Indium Tin Oxide, Graphene, Carbon Nanotubes, Thin Metal Films, Silver Nanowires Hybrid Materials, Aluminum-doped Zinc Oxide (AZO), Amorphous Indium-Zinc Oxide, Gallium-doped Zinc Oxide (GZO), and poly polystyrene sulfonate (PEDOT). The electrodes may be a variety of shapes (e.g., coil, cylindrical, conical, flat, square, circular, domed, spherical, spear shaped, etc.) and may be placed in a variety of positions within the test container 14. For example, four test container electrodes 16 are shown near the bottom corners of the test container 14 and four test container electrodes 16 are below a solution 20 fill line of the test container 14.

The test system 10 is operable to detect and interpret electrical characteristics of an organic mass or an inorganic mass ("mass" 18) present in a test container 14 of the test container array 12. An organic mass includes living organisms or portions thereof. For example, the organic mass includes one or more cells (e.g., an individual cell 18, multiple cells, tissue, etc.) and/or one or more portions of a cell (e.g., a section of cell membrane). A cell may be from an animal, human, plant, and/or other biological cell and is any type of cell (e.g., heart, brain, neuron, muscle, skin, lung, etc.). An inorganic mass includes non-living organisms that produce an electrical characteristic (e.g., voltage, current, impedance, resistance, reactance, etc.) with or without a stimulus. For example, the inorganic mass is a chemical composition.

A cell 18a is a complex structural entity consisting of many organelles that can be electrically characterized as an impedance. Animal cells are surrounded by a cell membrane 22 composed of a lipid bilayer with proteins embedded in it. The cell membrane 22 acts as both an insulator and a diffusion barrier to the movement of ions. Internal and external ion concentrations of the cell 18a are different resulting in a cell membrane capacitance 24. The cell 18a has an internal impedance 26 (resistance and/or reactance) and a cell membrane impedance that arises from the fact that the cell membrane 22 impedes the movement of charges across it. Depending on the nature of testing, the inductance of a cell may or may not be negligible. The cell membrane capacitance 24 is relatively unaffected by molecules embedded in it and has a value estimated at about 0.9-2 $\mu F/cm^2$ (i.e., 90-200 $pF/\mu m^2$) where the total capacitance of the membrane is proportional to its area. There are hundreds of different types of biological cells ranging in size from about 5 $\mu m$-150 $\mu m$ in diameter with cell membrane thicknesses ranging from 7.5 nm to 10 nm.

A cell 18a can also be electrically characterized by cell membrane 22 potential. Cell membrane 22 potential or cell membrane 22 voltage is the difference in electric potential between the interior and exterior of the cell 18. Typical values of cell membrane 22 potential from the exterior of the cell are measured in ranges from a few nano-volts to milli-volts. In electrically excitable cells such as neurons and muscle cells, membrane potential changes occur when signals are transmitted within the cell. Signals are transmitted by the opening and closing of ion channels in the cell membrane 22 which can make the interior voltage of the cell more negative (hyperpolarization) or less negative (depolarization). For non-excitable cells, membrane potential is held at a relatively stable value called resting potential.

In FIG. 1, a mass 18 (e.g., one or more cells 18a) is shown in a solution 20 in the testing container 14. The solution 20 maintains the integrity and viability of the mass 18 and negligibly interferes with testing substances and/or biochemical reactions. For example, the solution 20 is a saline solution, a preservative, a cell culture solution, etc., that is electrical conductive. The test system 10 is operable to detect and interpret the electrical characteristics of the materials present in the testing container 14. For example, the test system 10 is operable to detect and interpret the electrical characteristics of the solution 20, the electrical characteristics of the mass 18 in the solution 20, and the electrical characteristics of the mass 18 in the solution 20 when a testing substance is added.

Based on the differences between the detected electrical characteristics of the mass 18 (e.g., with and without the testing substance), the test system 10 can determine the effect of a testing substance on a cell. The electrical characteristics of the mass 18 include one or more of impedance, membrane potential, size, shape, density, movement, orientation, cell excitation (e.g., beat amplitude), etc. For example, in a cell becoming non-viable, the cell membrane 22 is unable to maintain its potential resulting in a decreased capacitance (e.g., as a cell dies, its impedance drops). The test system 10 is able to detect this change in impedance and interpret the effect as cell death.

As another example, the size and shape of a cell responds to chemical, biological, and/or physical stimuli. Based on which test container electrodes 16 experience changes in electrical characteristics and at what level, the size, shape, and movement of a cell can be mapped. The test system 10 is able to detect changes in cell size, shape, and position (e.g., migration) in response to a testing substance and interpret the effect as a cell condition (e.g., a shrinking cell may indicate cell destruction, etc.).

As another example, a testing substance can have an impact the ion concentration of a cell 18 and thus affect the cell membrane 22 voltage. The test system 10 is able to detect this change in cell membrane 22 voltage and interpret the effect as the change in ion concentration caused by the testing substance. A more detailed discussion of data processing of the test system 10 is discussed with reference to FIGS. 7-16.

Figure 2:
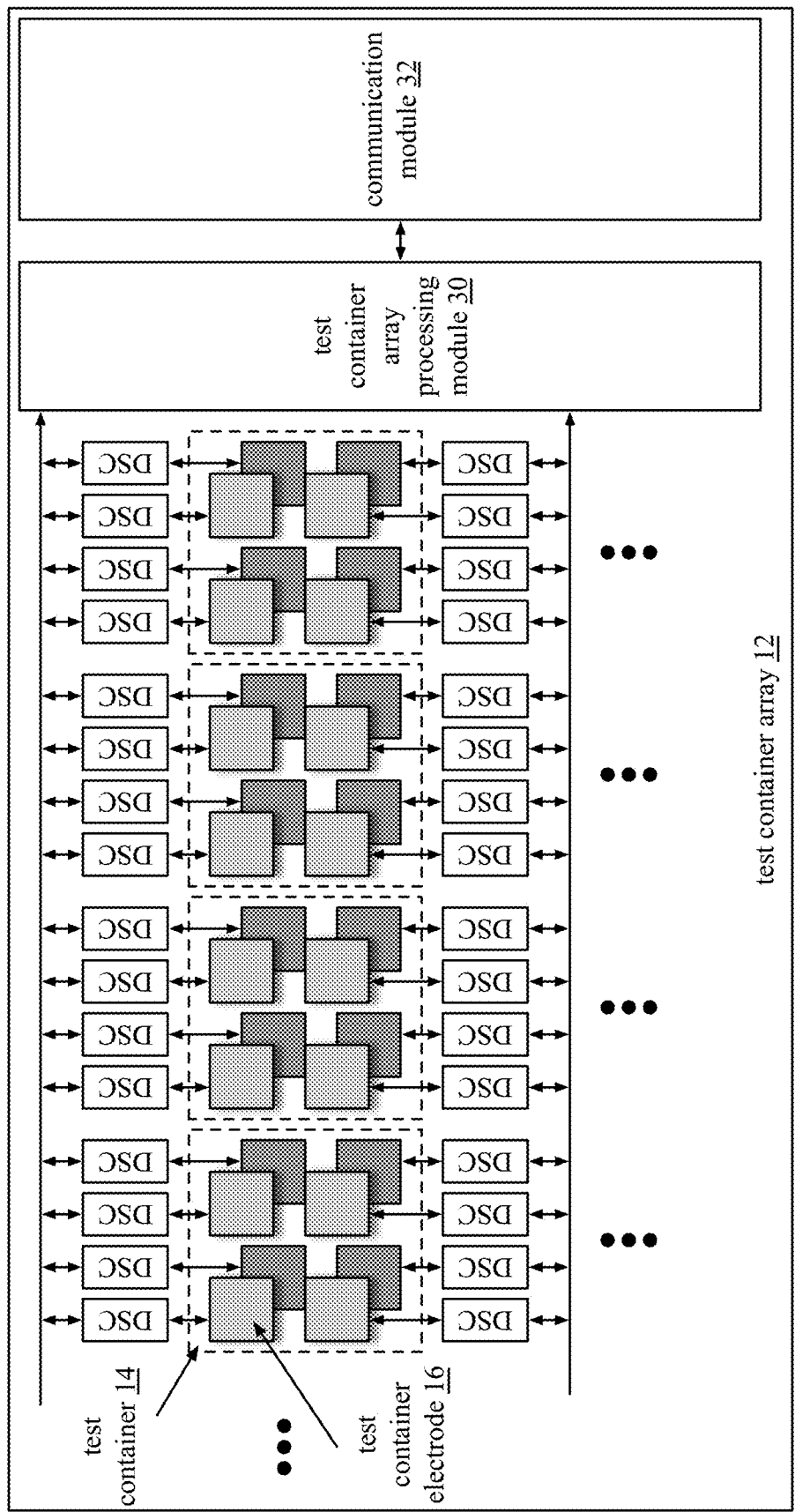
FIG. 2 is a schematic block diagram of another embodiment of a test system in accordance with the present invention.

FIG. 2 is a schematic block diagram of another embodiment of a test system 10 that includes a test container array 12 including a plurality of test containers 14, a plurality of test container electrodes 16, a plurality of drive-sense circuits (DSCs), a test container array processing module 30, and a communication module 32.

One or more of the test container array processing module 30 and the communication module 32 are integrated into the test container array 12 or within separate devices. The communication module 32 includes a wireless communication unit and/or a wired communication unit. A wireless communication unit includes a wireless local area network (WLAN) communication device, a cellular communication device, a Bluetooth device, and/or a ZigBee communication device. A wired communication unit includes a Gigabit LAN connection, a Firewire connection, and/or a proprietary computer wired connection. Regardless of the specific implementation of the communication module 32, it is constructed in accordance with one or more wired communication protocol and/or one or more wireless communication protocols that is/are in accordance with the one or more of the Open System Interconnection (OSI) model, the Transmission Control Protocol/Internet Protocol (TCP/IP) model, and other communication protocol module.

Each test container 14 includes a set of test container electrodes 16. For example, eight test container electrodes 16 are included in each test container 14. The eight test container electrodes 16 are shown staggered and in different shades of gray to indicate different positions within the test container 14. For example, the darker shaded electrodes are near the bottom the container 14 and the lighter shaded electrodes are near a fill line of the test container.

Each test container electrode 16 is coupled to a drive-sense circuit (DSC). The DSCs provide electrode signals to the test container electrodes 16 and detect changes in electrical characteristics of the test container electrodes 16 without the use of electric field enhancers. As such, the cell(s) are not damaged during testing, since an electric field enhancer is not used, and the changes to the electrical characteristics of the cell(s) are directly attributable to the stimulus added to the solution (e.g., various medications, various environmental elements, pollutants, viruses, bacteria, etc.). This provides a significant benefit for individualized medicine where a patient's cells can be tested for a variety of conditions and responses. And not just an immediate reaction, but over time since the testing itself does not kill the cells. The DSC functions as described in co-pending patent application entitled, "DRIVE SENSE CIRCUIT WITH DRIVE-SENSE LINE", having a serial number of Ser. No. 16/113,379, and a filing date of Aug. 27, 2018.

The DSCs provide the detected changes in electrical characteristics of the test container electrodes 16 to the test container array processing module 30. The test container array processing module 30 (i.e., the processing module) is described in greater detail at the end of the detailed description of the invention section. The test container array processing module 30 processes the detected changes in electrical characteristics of the test container electrodes 16 from DSCs to determine the electrical characteristics of cells of the test system 10. For example, the test container array processing module 30 filters the data (e.g., via a bandpass filter) received from the DSCs and interprets the filtered data to determine impedance values representative of the electrical characteristics of cells. A more detailed discussion of data processing of the test system 10 is discussed with reference to FIGS. 7-16.

The test container array processing module 30 communicates the electrical characteristics of cells to the communication module 32. Communicating the electrical characteristics of cells to the communication module 32 may include formatting the data in a particular format with respect to the communication protocol of the communication module. The communication module 32 is operable to communicate the electrical characteristics of cells via one or more communication protocols.

FIG. 2A is a schematic block diagram of an embodiment of a set of test container electrodes 16 coupled to drive sense circuits (DSCs 1-8). For example, DSC 1 is coupled to a first test container electrode 16, DSC 2 is coupled to a second test container electrode 16, and so on. Each DSC 1-8 is operable to transmit a transmit signal (TX_signal) at a particular frequency and receive a set of receive signals (RX_signals) from the other DSCs at a set of different frequencies.

Because each of the DSCs 1-8 are operable to transmit and receive signals at different frequencies, each DSC 1-8 is able to obtain different seven impedance measurements based on seven different orientations within the test container 14. Different frequencies provide different impedance measurements for analysis. For example, the impedance of a capacitor (i.e., capacitor reactance) is equal to $1/(2\pi fC)$ where f is the frequency in Hz and C is the capacitance in farads.

FIG. 2B is a diagram of an example of a transmit signal and a receive signal, in the frequency domain, of drive sense circuits (DSCs 1-8) of the embodiment of FIG. 2A. Each DSC 1-8 is operable to transmit a transmit signal (TX_signal) at a particular frequency and receive a set of receive signals (RX signals) at different frequencies from the other DSCs. For example, a DSC transmits a transmit signal at frequency ft and is operable to receive a set of receive signals from the other seven DSCs at frequencies f1-f7.

FIG. 2C is a diagram of an example of a frequency pattern used by the drive-sense circuits (DSCs 1-8) of the embodiment of FIG. 2A. In this example, the DSC 1 transmits a transmit signal at a frequency f_1, the DSC 2 transmits a transmit signal at a frequency f_2, the DSC 3 transmits a transmit signal at a frequency f_3, the DSC 3 transmits a transmit signal at a frequency f_3, the DSC 4 transmits a transmit signal at a frequency f_4, the DSC 5 transmits a transmit signal at a frequency f_5, the DSC 6 transmits a transmit signal at a frequency f_6, the DSC 7 transmits a transmit signal at a frequency f_7, and the DSC 8 transmits a transmit signal at a frequency f_8. The DSCs may transmit the transmit signals one at a time, all at the same time, or in a combination thereof.

The DSC 1 receives a set of receive signals from DSCs 2-8 at frequencies f_2, f_3, f_4, f_5, f_6, f_7, and f_8. The DSC 2 receives a set of receive signals from DSCs 1 and 3-8 at frequencies f_1, f_3, f_4, f_5, f_6, f_7, and f_8. The DSC 3 receives a set of receive signals from DSCs 1-2 and 4-8 at frequencies f_1, f_2, f_4, f_5, f_6, f_7, and f_8. The DSC 4 receives a set of receive signals from DSCs 1-3 and 5-8 at frequencies f_1, f_2, f_3, f_5, f_6, f_7, and f_8. The DSC 5 receives a set of receive signals from DSCs 1-4 and 6-8 at frequencies f_1, f_2, f_3, f_4, f_6, f_7, and f_8. The DSC 6 receives a set of receive signals from DSCs 1-5 and 7-8 at frequencies f_1, f_2, f_3, f_4, f_5, f_7, and f_8. The DSC 7 receives a set of receive signals from DSCs 1-6 and 8 at frequencies f_1, f_2, f_3, f_4, f_5, f_6, and f_8. The DSC 8 receives a set of receive signals from DSCs 1-7 at frequencies f_1, f_2, f_3, f_4, f_5, f_6, and f_7.

Each of the eight DSCs are operable to receive information from eight different locations within a test container 14 (e.g., from 7 other DSCs and from itself). Thus, 64 different circuits (e.g., a circuit between one transmit DSC and one receive DSC) are created for test container analysis.

FIG. 2D is a schematic diagram of an example of a generic circuit of a transmit drive-sense circuit (DSC) and a receive DSC of the embodiment of FIG. 2A. The DSC that is transmitting a transmit signal is referred to as a transmit drive-sense circuit (DSC) (e.g., DSC_TX) and the DSC that is receiving a receive signal is referred to as a receive drive-sense circuit (DSC) (e.g., DSC_RX).

Here, the DSC_TX is transmitting a transmit signal (TX_signal) at a frequency fx. The DSC_RX receives a receive signal (RX signal) at a frequency fx where the RX signal at the frequency fx includes a representation of the test container solution impedance and information pertaining to the mass' (e.g., organic or inorganic material) electrical characteristics with respect to the orientation relationship between the DSC_TX and the DSC_RX.

Figure 2E:
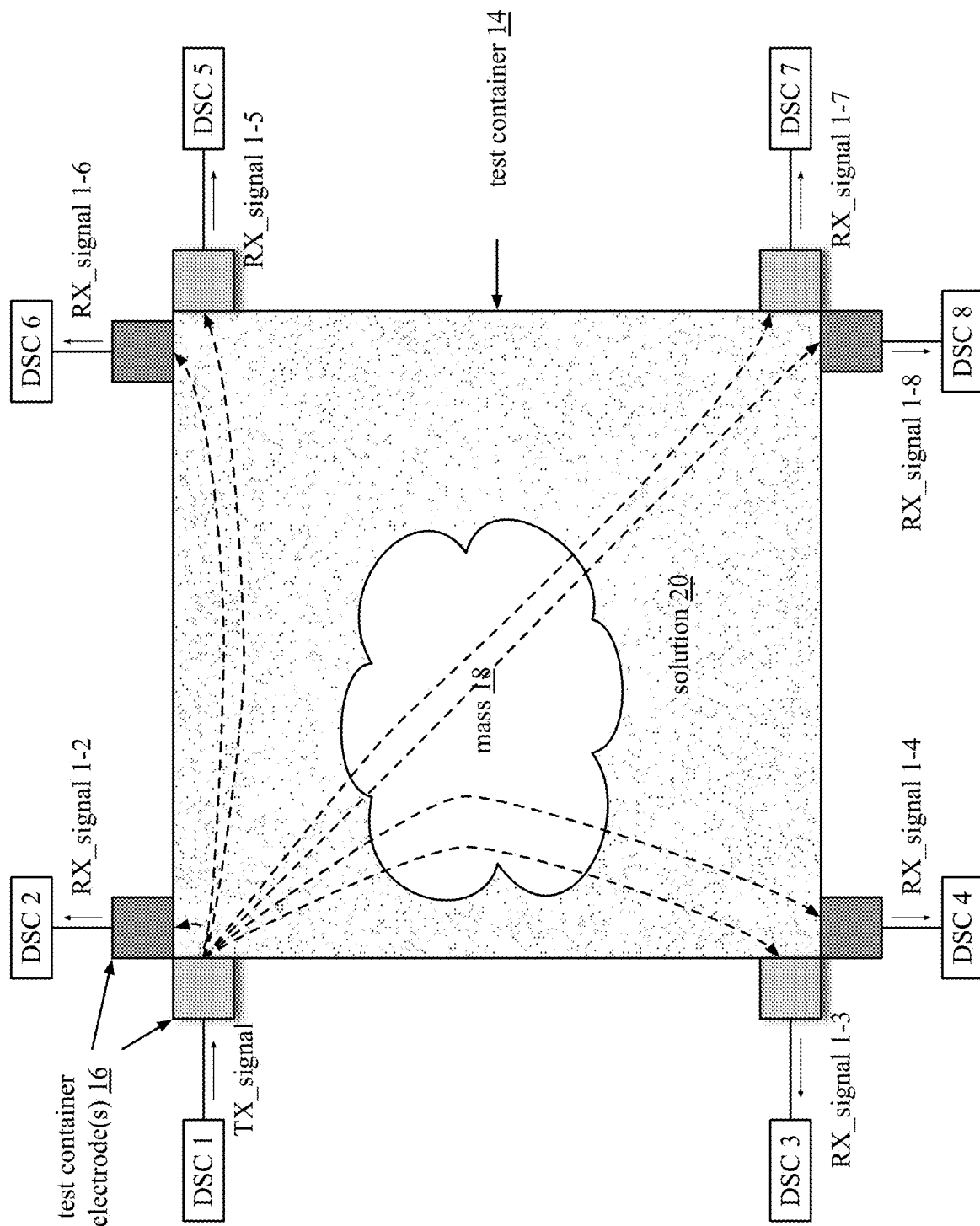
FIG. 2E is a schematic diagram of an example of a drive-sense circuit (DSC) transmitting a signal that is being received by the other DSCs within the embodiment of FIG. 2A in accordance with the present invention.

FIG. 2E is a schematic diagram of an example of a drive-sense circuit (DSC) transmitting a signal that is being received by the other DSCs within the embodiment of FIG. 2A. FIG. 2E includes a test container 14 including eight test container electrodes 16 where each electrode is coupled to a drive-sense circuit (DSCs 1-8). The test container 14 contains a solution 20 and mass 18 (e.g., one or more cells, etc.).

The DSC 1 is transmitting a transmit signal TX_signal. The DSC 2 receives the RX_signal 1-2, where the RX_signal 1-2 is at the same frequency of TX_signal and includes a representation of the test container solution 20 impedance and the mass' 18 electrical characteristics measured with respect to DSC 2 from DSC 1. The DSC 3 receives the RX_signal 1-3, where the RX_signal 1-3 is at the same frequency of TX_signal and includes a representation of the test container solution 20 impedance and the mass' 18 electrical characteristics measured with respect to DSC 3 from DSC 1.

The DSC 4 receives the RX_signal 1-4, where the RX_signal 1-4 is at the same frequency of TX_signal and includes a representation of the test container solution 20 impedance and the mass' 18 electrical characteristics measured with respect to DSC 4 from DSC 1. The DSC 5 receives the RX_signal 1-5, where the RX_signal 1-5 is at the same frequency of TX_signal and includes a representation of the test container solution 20 impedance and the mass' 18 electrical characteristics measured with respect to DSC 5 from DSC 1. The DSC 6 receives the RX_signal 1-6, where the RX_signal 1-6 is at the same frequency of the TX_signal and includes a representation of the test container solution 20 impedance and the mass' 18 electrical characteristics measured with respect to DSC 6 from DSC 1.

The DSC 6 receives the RX_signal 1-7, where the RX_signal 1-7 is at the same frequency of the TX_signal and includes a representation of includes the test container solution 20 impedance and the mass' 18 electrical characteristics measured with respect to DSC 7 from DSC 1. The DSC 8 receives the RX_signal 1-8, where the RX_signal 1-8 is at the same frequency of the TX_signal and includes a representation of the test container solution 20 impedance and the mass' 18 electrical characteristics measured with respect to DSC 8 from DSC 1. As such, the impedance information obtained in the RX signals 1-2 through 1-8 provides an impedance map of the materials present in the test container 14 (e.g., the solution 20 and the mass 18).

Figure 2F:
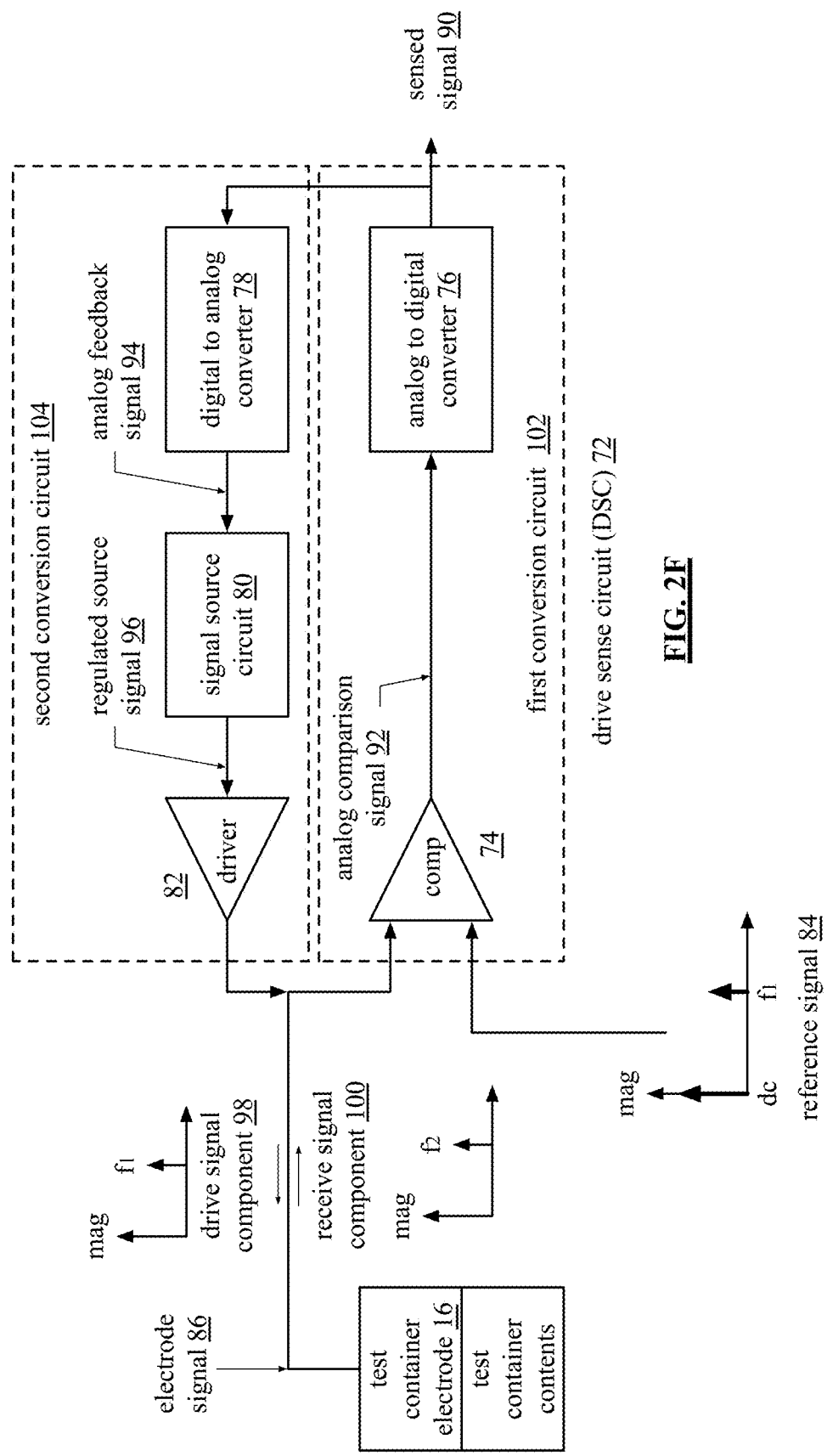
FIG. 2F is a schematic block diagram an embodiment of a drive-sense circuit (DSC) in accordance with the present invention.

FIG. 2F is a schematic block diagram an embodiment of a drive-sense circuit (DSC) 72 that includes a first conversion circuit 102 and a second conversion circuit 104. The first conversion circuit 102 includes comparator (comp) 74 and an analog to digital converter (ADC) 76. The second conversion circuit 104 includes a digital to analog converter (DAC) 78, a signal source circuit 80, and a driver 82. The analog to digital converter (ADC) 76 may be implemented in a variety of ways. For example, the (ADC) 76 is one of: a flash ADC, a successive approximation ADC, a ramp-compare ADC, a Wilkinson ADC, an integrating ADC, a delta encoded ADC, and/or a sigma-delta ADC. The digital to analog converter (DAC) 214 may be a sigma-delta DAC, a pulse width modulator DAC, a binary weighted DAC, a successive approximation DAC, and/or a thermometer-coded DAC.

The feedback loop of the drive sense circuit 72 functions to keep the electrode signal 86 substantially matching the analog reference signal 84. As such, the electrode signal 86 will have a similar waveform to that of the analog reference signal 84. The electrode signal 86 includes a drive signal component 98 and a receive signal component 100. The drive signal component 98 corresponds to the transmit signal at f1 produced by the DSC and the receive signal component 100 corresponds to a received transmit signal at f2 produced by another DSC circuit.

The first conversion circuit 102 converts the electrode signal 86 into a sensed signal 90. The second conversion circuit 104 generates the drive signal component 98 from the sensed signal 90. As an example, the first and second conversion circuits 102 and 104 function to keep the electrode signal 86 substantially constant (e.g., substantially matching the reference signal 84) with the first conversion circuit creating the sensed signal 90 to correspond to changes in a receive signal component 100 of the electrode signal 86 and the second conversion circuit 104 functions generating the drive signal component 98 based on the sensed signal 90.

In an example, the electrode signal 86 is provided to a test container electrode 16 as a regulated current signal. The regulated current (I) signal in combination with the impedance (Z) of the contents of test container (e.g., solution and/or mass) creates a voltage (V), where V=I*Z. As the impedance (Z) of test container contents changes, the regulated current (I) signal is adjusted to keep the voltage (V) substantially unchanged. To regulate the current signal, the DSC adjusts the sensed signal 90 and the drive signal component 98 based on the receive signal component 100, which is indicative of the impedance of the test container contents and changes thereof.

More specifically, the comparator 74 compares the electrode signal 86 to the analog reference signal 84 having the oscillating component frequency f1 to produce an analog comparison signal 92. The analog reference signal 84 (e.g., a current signal or a voltage signal) includes a DC component and an oscillating component at a first frequency f1. The DC component is a DC voltage in the range of a few tens of milli-volts to tens of volts or more. The oscillating component includes a sinusoidal signal, a square wave signal, a triangular wave signal, a multiple level signal (e.g., has varying magnitude over time with respect to the DC component), and/or a polygonal signal (e.g., has a symmetrical or asymmetrical polygonal shape with respect to the DC component). In another example, the frequency of the oscillating component may vary so that it can be tuned to the impedance of the electrode and/or to be off-set in frequency from other electrode signals.

In an embodiment, a processing module (e.g., one or more of a test container processing module and a test container array processing module) provides analog reference signals to the drive sense circuits. For example, each drive sense circuit receives a unique analog reference signal. As another example, a first group of drive sense circuits receive a first analog reference signal and a second group of drive sense circuits receive a second analog reference signal. In yet another example, the drive sense circuits receive the same analog reference signal. Note that the processing module uses a combination of analog reference signals with control signals to ensure that different frequencies are used for oscillating components of the analog reference signal.

The analog to digital converter 76 converts the analog comparison signal 84 into the sensed signal 90. Because the analog reference signal 84 includes a DC component and an oscillating component the sensed signal 90 will have a substantially matching DC component and oscillating component at frequency f1.

The second conversion circuit 104 adjusts the regulated current based on the changes to the sensed signal 90. More specifically, the digital to analog converter (DAC) 78 converts the sensed signal 90 into an analog feedback signal 94. The signal source circuit 80 (e.g., a dependent current source, a linear regulator, a DC-DC power supply, etc.) generates a regulated source signal 96 (e.g., a regulated current signal or a regulated voltage signal) based on the analog feedback signal 94. The driver 82 increases power of the regulated source signal 94 to produce the drive signal component 86. Note that, in an embodiment, the driver may be omitted.

As another example, the electrode signal 86 is provided to the test container electrode 16 as a regulated voltage signal. The regulated voltage (V) signal in combination with the impedance (Z) of the test container contents creates an electrode current (I), where I=V/Z. As the impedance (Z) of electrode changes, the regulated voltage (V) signal is adjusted to keep the electrode current (I) substantially unchanged. To regulate the voltage signal, the first conversion circuit 102 adjusts the sensed signal 90 based on the receive signal component 100, which is indicative of the impedance of the test container contents and changes thereof. The second conversion circuit 104 adjusts the regulated voltage based on the changes to the sensed signal 90.

Multiplexing of a DSC to a test container 14 is possible since the sampling rate of a cell(s) is very low (e.g., in the range of 100 Hz to 0.1 Hz). For example, a cell's electrical characteristics are sampled once per second. Further, at this sampling rate, the digital filtering of the DSC outputted signals can have a very narrow bandwidth (e.g., 100 Hz or less). The combination of low sampling rate, greater than 100 dBm SNR of the DSCs, and very narrow bandwidth allows for very accurate measurements of very low voltage (and/or current) changes of the cells (e.g., of a few nano-volts to tens of pico-volts) in this embodiment and in others.

Figure 2G:
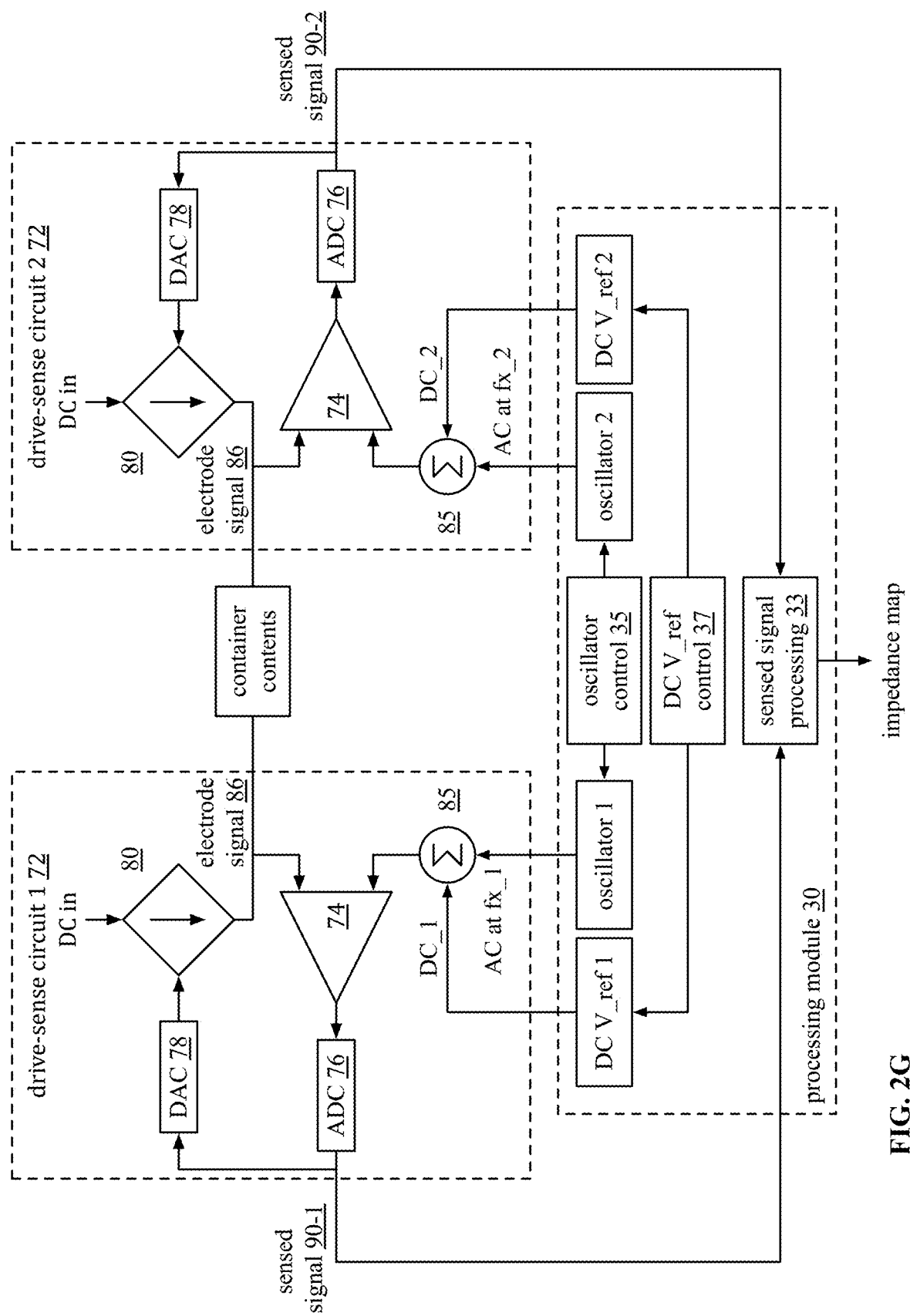
FIG. 2G is a schematic block diagram an example of drive-sense circuits (DSCs) sensing contents of a test container in accordance with the present invention.

FIG. 2G is a schematic block diagram an example of drive-sense circuits (DSCs 1-2) 72 sensing contents of a test container 14. Each DSC includes a comparator 74, an analog to digital converter (ADC) 76, a digital to analog converter (DAC) 78, a regulated current source circuit 80, and an adder 85. The processing module 30 (e.g., the test container array processing module) includes a sensed signal processing unit 33, a DC V_ref control unit 37, and an oscillator control unit 35.

The DC V_ref control 37 generates DC voltage components (e.g., DC_1 and DC_2) of analog reference signals to provide to the DSCs. The DC V_ref control 37 generates DC V_ref 1 at a voltage of DC_1 to provide to DSC 1 and a DC V_ref 2 at a voltage of DC_2 to provide to DSC 2. DC_1 and DC_2 are voltages in the range of a few tens of milli-volts to tens of volts or more. The DC V_ref control 37 generates DC_1 and DC_2 to be different such that a voltage potential exists between the DSCs 1-2 72.

The oscillator control 35 generates the AC oscillating components of analog reference signals provided to the DSCs. The oscillator control 35 generates an oscillator 1 at frequency fx_1 to provide to DSC 1 and an oscillator 2 at a frequency fx_2 to provide to DSC 2. The oscillating components include a sinusoidal signal, a square wave signal, a triangular wave signal, a multiple level signal (e.g., has varying magnitude over time with respect to the DC component), and/or a polygonal signal (e.g., has a symmetrical or asymmetrical polygonal shape with respect to the DC component).

The adders 85 of the DSCs 1-2 72 combine the DC components with the oscillating components to produce analog reference signals for input to the comparators 74. The DSCs function to keep the electrode signal 86 substantially constant (e.g., substantially matching the reference signal).

For example, an electrode signal 86 is provided to a test container electrode as a regulated current signal. The regulated current (I) signal in combination with the impedance (Z) of the contents of test container (e.g., solution and/or biological material) creates a voltage (V), where V=I*Z. As the impedance (Z) of test container contents changes, the regulated current (I) signal is adjusted to keep the voltage (V) substantially unchanged. To regulate the current signal, each DSC 1-2 72 adjusts the sensed signals 90-1 and 90-2 based on the receive signal component of the electrode signal 86, which is indicative of the impedance of the test container contents and changes thereof.

The DSCs 72 provide the sensed signals 90-1 and 90-2 to the sensed signal processing unit 33 of the processing module 30. The processing module 30 generates an impedance map of the test container based on the sensed signals.

Figure 2I:
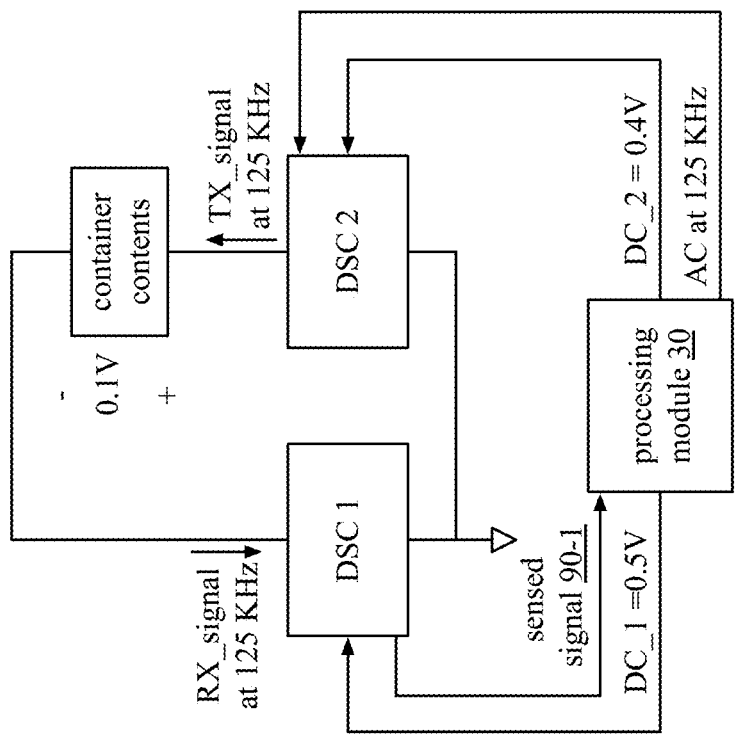
FIG. 2I is a schematic block diagram another example of drive-sense circuits (DSCs) sensing contents of a test container in accordance with the present invention.
Figure 2H:
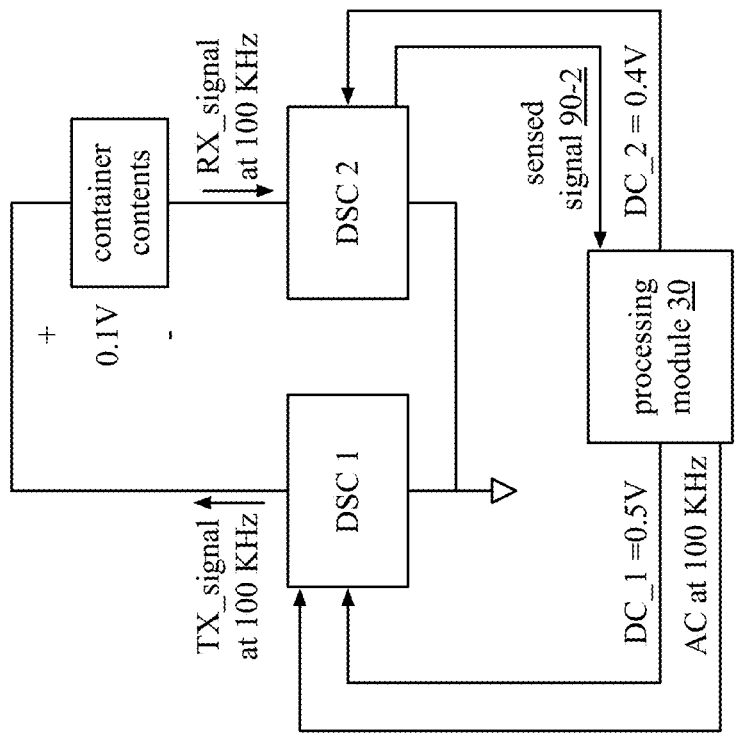
FIG. 2H is a schematic block diagram another example of drive-sense circuits (DSCs) sensing contents of a test container in accordance with the present invention.

FIG. 2H is a schematic block diagram another example of drive-sense circuits (DSCs 1-2) sensing contents of a test container. The processing module 30 provides the DSC 1 a DC voltage signal component DC_1=0.5 V and an AC oscillating signal component at a frequency of 100 KHz. The processing module 30 provides the DSC 2 a DC voltage component DC_2=0.4 V such that a voltage potential of 0.1 V exists between DSC 1 and DSC 2.

The DSC 1 transmits a transmit signal (TX_signal) at 100 KHz through the test container. The DSC 2 receives a receive signal (RX_signal) at the same frequency as the TX_signal, 100 KHz. To regulate the current signal, the DSC 2 adjusts the sensed signal 90-2 based on the RX_signal at 100 KHz, which is indicative of the impedance of the test container contents and changes thereof.

FIG. 2I is a schematic block diagram another example of drive-sense circuits (DSCs 1-2) sensing contents of a test container. The processing module 30 provides the DSC 2 a DC voltage component DC_2=0.4 V and an AC oscillating signal component at a frequency of 125 KHz. The processing module 30 provides the DSC 1 a DC voltage component DC_1=0.5 V such that a voltage potential of 0.1 V exists between DSC 2 and DSC 1.

The DSC 2 transmits a transmit signal (TX_signal) at 125 KHz through the test container. The DSC 2 receives the receive signal (RX_signal) at the same frequency as the TX_signal, 125 KHz. To regulate the current signal, the DSC 1 adjusts the sensed signal 90-1 based on the RX_signal at 125 KHz, which is indicative of the impedance of the test container contents and changes thereof.

Figure 3:
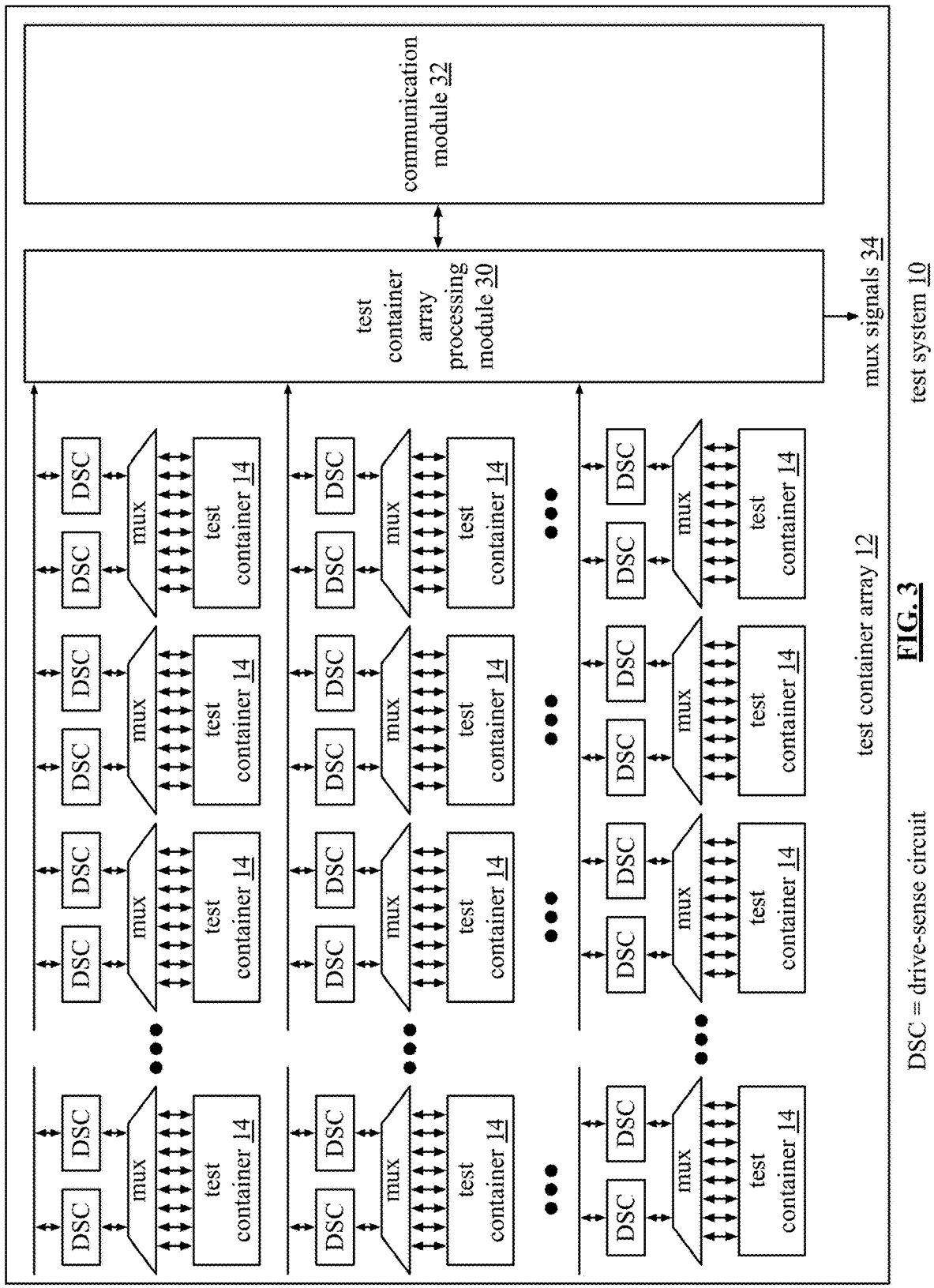
FIG. 3 is a schematic block diagram of another embodiment of a test system in accordance with the present invention.

FIG. 3 is a schematic block diagram of another embodiment of a test system 10 that includes a test container array 12 including a plurality of test containers 14, a plurality of test container electrodes 16, a plurality of drive-sense circuits (DSCs), a plurality of multiplexors (muxes), a test container array processing module 30, and a communication module 32. FIG. 3 operates similarly to FIG. 2 except that the test container electrodes of a test container 14 are coupled to a pair of drive-sense circuits (DSC) via multiple inputs of a multiplexor. The test container processing module 30 provides control signals (e.g., mux signals 34) to the multiplexors.

FIG. 3A is a schematic block diagram of another embodiment of a set of test container electrodes 16 coupled to drive-sense circuits (DSCs). The set of test container electrodes 16 are coupled to a pair of DSCs 1-2 via multiple inputs of two multiplexors. The DSC 1 is coupled to test container electrodes 1-4 via a first multiplexor and the DSC 2 is coupled to test container electrodes 5-8 via a second multiplexor.

The DSC 1 transmits a transmit signal at a frequency f1 to the electrodes 1-4 and the DSC 2 transmits a transmit signal at a frequency f2 to the electrodes 5-8. Therefore, the DSC 1 receives the receive signals from the electrodes 1-4 at frequency f2 and the DSC 2 the receive signals from the electrodes 5-8 at frequency f1.

FIG. 3B is a diagram of an example of a frequency pattern used by the drive-sense circuits (DSCs) of the embodiment of FIG. 3A. The first two columns show 32 different circuits created between DSC 1 and DSC 2. For example, when DSC 1 transmits at a first frequency via electrode 1, DSC 2 transmits at a fifth frequency via electrode 5. Therefore, the DSC 1 receives a receive signal at the fifth frequency via electrode 1 and the DSC 5 receives a receive signal at the first frequency via electrode 5.

The second two columns shows 32 additional circuits created between DSC 1 and DSC 2. For example, when DSC 1 transmits at a third frequency via electrode 3, DSC 2 transmits at a fifth frequency via electrode 5. Therefore, the DSC 1 receives a receive signal at the fifth frequency via electrode 3 and the DSC 2 receives a receive signal at the third frequency via electrode 5. The two sets of 32 circuits are run at the same time.

Figure 3C:
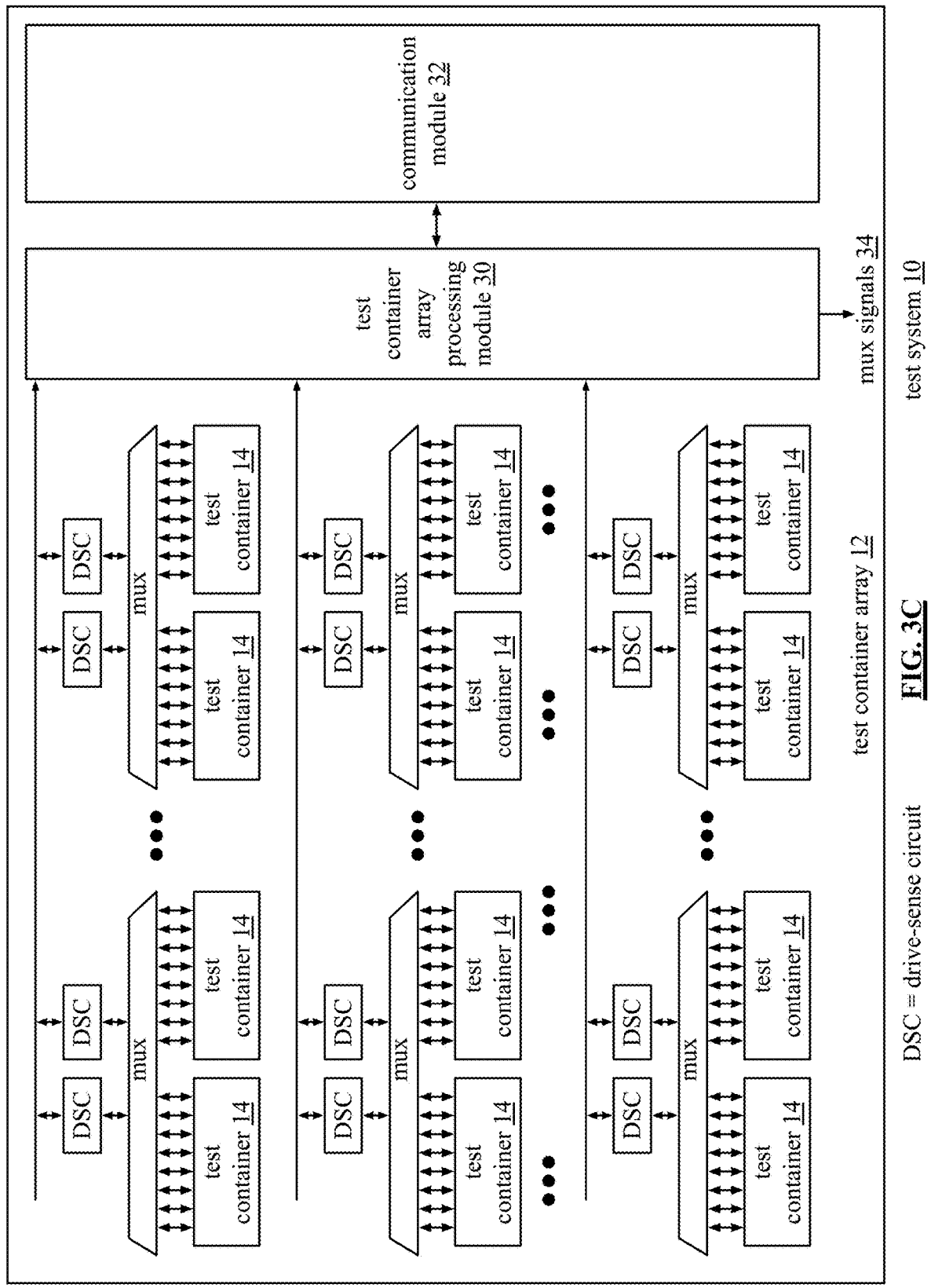
FIG. 3C is a schematic block diagram of another embodiment of a test system in accordance with the present invention.

FIG. 3C is a schematic block diagram of another embodiment of a test system 10 that includes a test container array 12 including a plurality of test containers 14, a plurality of test container electrodes 16, a plurality of drive-sense circuits (DSCs), a plurality of multiplexors (muxes), a test container array processing module 30, and a communication module 32. FIG. 3C operates similarly to FIG. 3 except that the test container electrodes of two test containers 14 are coupled to a pair of drive-sense circuits (DSC) via multiple inputs of a multiplexor.

Figure 4:
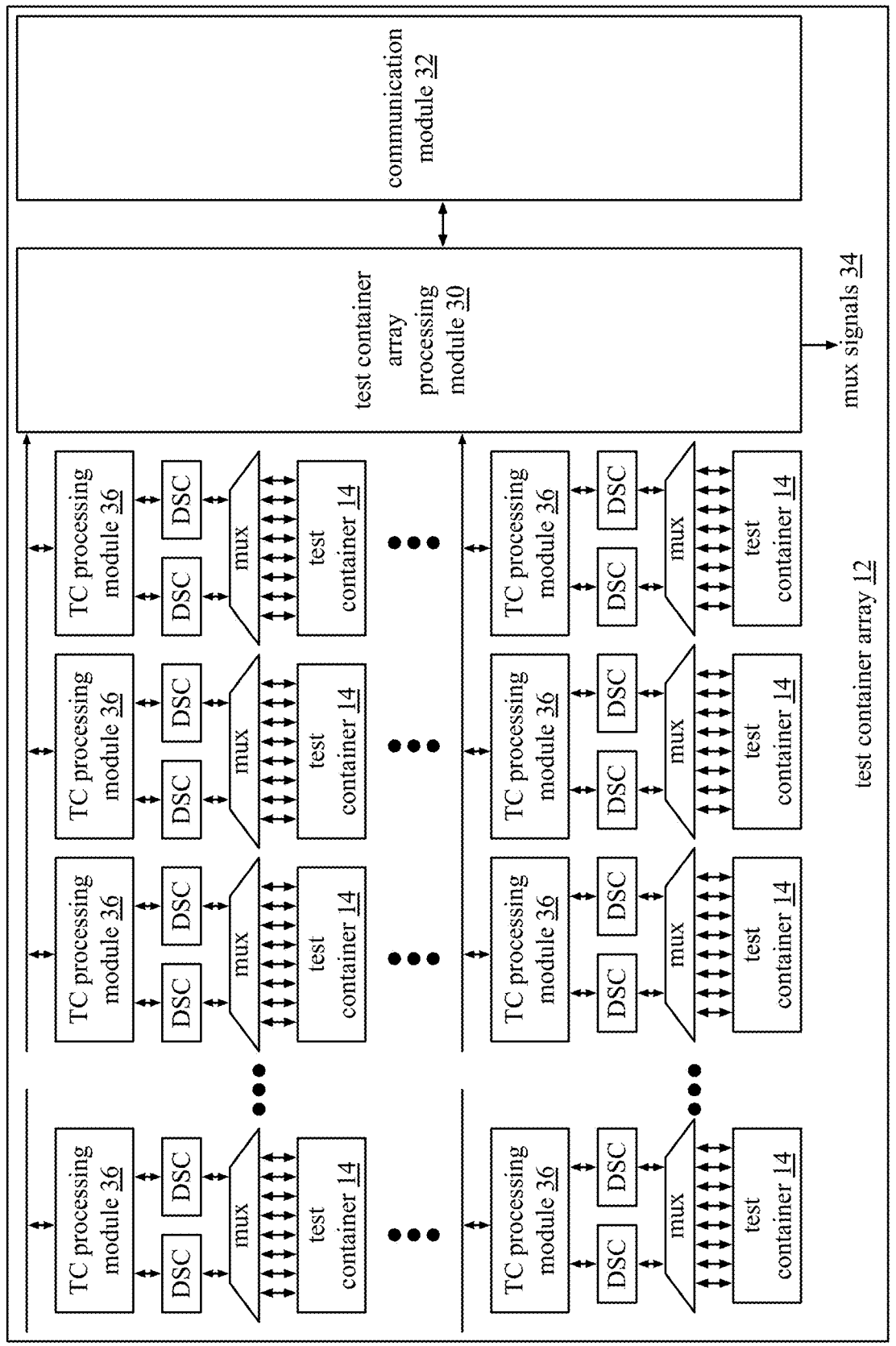
FIG. 4 is a schematic block diagram of another embodiment of a test system in accordance with the present invention.

FIG. 4 is a schematic block diagram of another embodiment of a test system 10 that includes a test container array 12 including a plurality of test containers 14, a plurality of test container electrodes 16, a plurality of drive-sense circuits (DSCs), a plurality of multiplexors (muxes), a test container array processing module 30, and a communication module 32. FIG. 4 operates similarly to FIG. 3 except that each test container 14 includes a test container (TC) processing module 36.

The pair of DSCs coupled to a test container, provides the TC processing module 36 the detected changes in electrical characteristics of the test container electrodes 16 in the form of receive signals. The test container processing modules 36 process the received signals representative of the detected changes in electrical characteristics to produce digital data that quantifies the electrical characteristics of cells (and/or changes thereto) of the test system 10. For example, the test container processing modules 36 filter the data (e.g., via a bandpass filter) received from the DSCs. Digital processing of received signals of drive sense circuits (DSCs) is further described in pending patent application entitled, "Receive Analog To Digital Circuit Of A Low Voltage Drive Circuit Data Communication System", having a filing date of Feb. 4, 2019, and an application number of Ser. No. 16/266,953.

The test container processing modules 36 communicate the processed (e.g., filtered) data representing the electrical characteristics, and/or changes thereto, of cells to the test container array processing module 30. The test container array processing module 30 interprets the filtered data as an impedance value representative of electrical characteristics of a cell, formats the impedance values for communication, and communicates the formatted data representing electrical characteristics of cells to the communication module 32 for communication.

Figure 5:
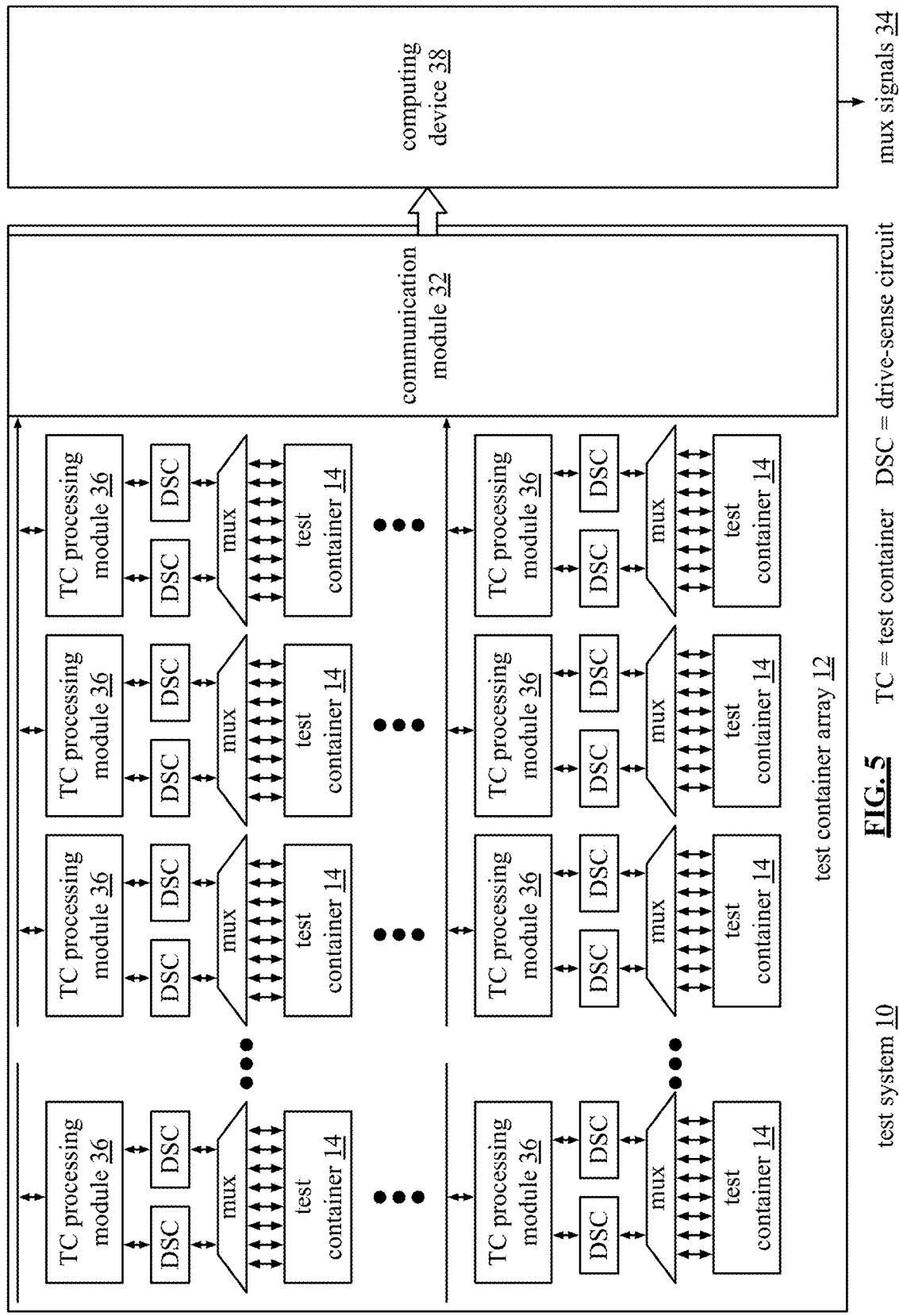
FIG. 5 is a schematic block diagram of another embodiment of a test system in accordance with the present invention.

FIG. 5 is a schematic block diagram of another embodiment of the test system 10 that includes a computing device 38 and a test container array 12 including a plurality of test containers 14, a plurality of test container electrodes 16, a plurality of drive-sense circuits (DSCs), a plurality of multiplexors (muxes), a plurality of test container (TC) processing modules 36, and a communication module 32. Computing device 38 may be a portable computing device and/or a fixed computing device. A portable computing device may be a social networking device, a gaming device, a cell phone, a smart phone, a digital assistant, a digital music player, a digital video player, a laptop computer, a handheld computer, a tablet, a video game controller, and/or any other portable device that includes a computing core (e.g., having a processing module).

A fixed computing device may be a computer (PC), an interactive white board, an interactive table top, an interactive desktop, an interactive display, a computer server, a cable set-top box, vending machine, an Automated Teller Machine (ATM), an automobile, a satellite receiver, a television set, a printer, a fax machine, home entertainment equipment, a video game console, and/or any type of home or office computing equipment.

FIG. 5 operates similarly to FIG. 4 except that the test container array 12 does not include the test container array processing module 30. The pair of DSCs coupled to a test container provides the TC processing module 36 of the test container 14 the detected changes in electrical characteristics of the test container electrodes 16 in the form of received signals. The test container processing module 36 processes the detected changes in electrical characteristics of the test container electrodes 16 from DSC to determine the electrical characteristics of cell and/or changes thereto. For example, the test container processing modules 36 filter the data (e.g., via a bandpass filter) received from the DSCs to produce filtered data. The test container processing modules 36 also format the data and communicates the filtered, formatted data representing electrical characteristics of cells to the communication module 32.

The communication module 32 communicates the filtered, formatted data representing electrical characteristics, and/or changes thereto, of cells to the computing device 38. As an example, the computing device 38 interprets the filtered data from the communication module 32 as impedance values representative of electrical characteristics of a cell. The computing device 38 communicates the multiplexor signals 34 to the DSCS via the communication module 32 and the TC processing modules 36. Alternatively, the test container processing modules 36 provide the multiplexor signals 34 to its respective multiplexors.

Figure 6:
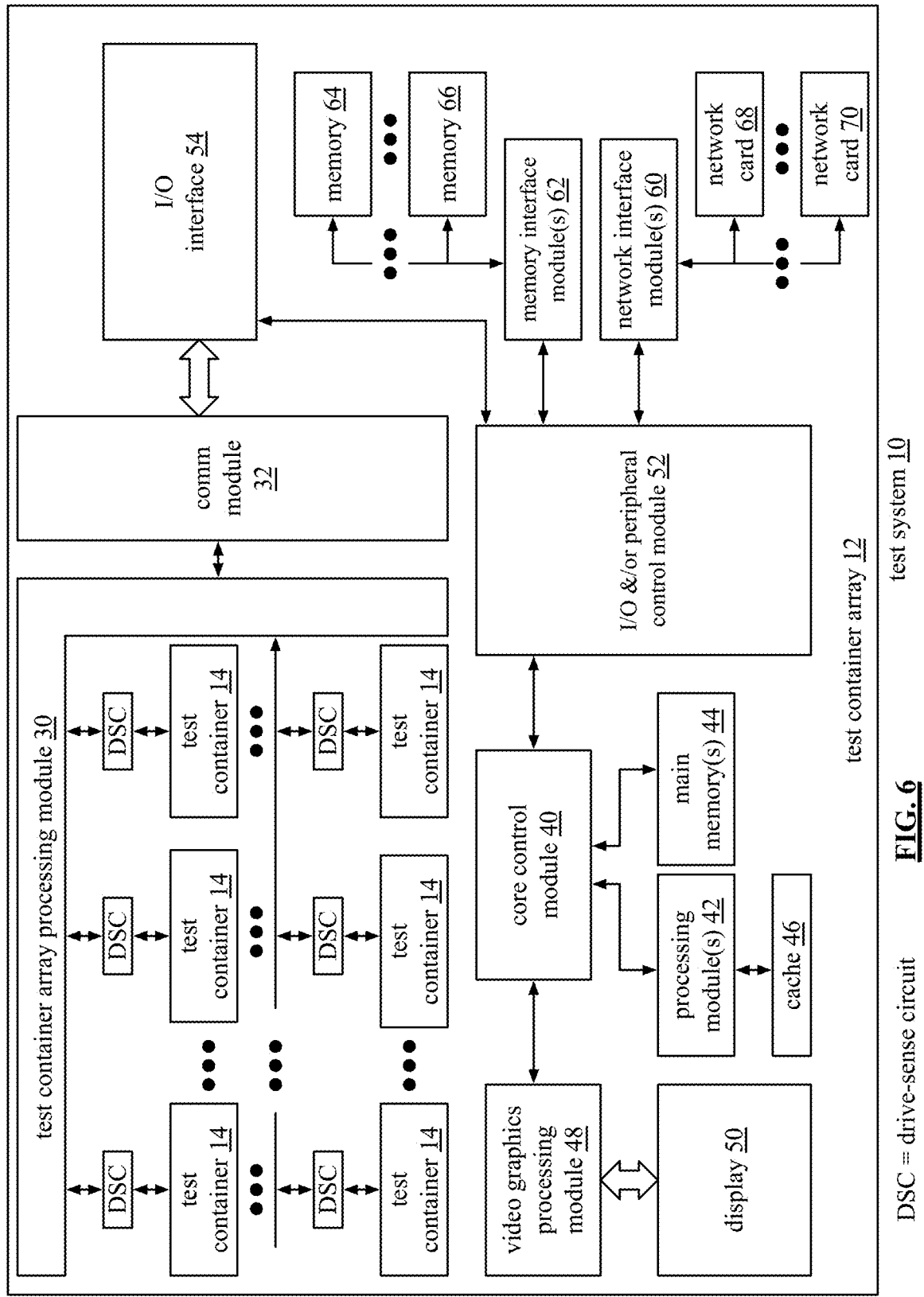
FIG. 6 is a schematic block diagram of another embodiment of a test system in accordance with the present invention.

FIG. 6 is a schematic block diagram of another embodiment of a test system 10 that includes a test container array 12 including a plurality of test containers 14, a plurality of test container electrodes 16, a plurality of drive-sense circuits (DSCs), a plurality of multiplexors (muxes), a test container array processing module 30, a communication module 32, a core control module 40, one or more additional processing modules 42, one or more main memories 44, cache memory 46, a video graphics processing module 48, a display 50, an Input-Output (I/O) peripheral control module 52, one or more input interface modules, one or more output interface modules, one or more network interface modules 60, and one or more memory interface modules 62.

The additional processing module 42 is described in greater detail at the end of the detailed description of the invention section and, in an alternative embodiment, has a direct connection to the main memory 44. In an alternate embodiment, the core control module 40 and the I/O and/or peripheral control module 52 are one module, such as a chipset, a quick path interconnect (QPI), and/or an ultra-path interconnect (UPI).

Each of the main memories 44 includes one or more Random Access Memory (RAM) integrated circuits, or chips. For example, a main memory 44 includes four DDR4 ($4^{th}$ generation of double data rate) RAM chips, each running at a rate of 2,400 MHz. In general, the main memory 44 stores data and operational instructions most relevant for the processing module 42. For example, the core control module 40 coordinates the transfer of data and/or operational instructions from the main memory 44 and the memory 64-66. The data and/or operational instructions retrieve from memory 64-66 are the data and/or operational instructions requested by the processing module or will most likely be needed by the processing module. When the processing module is done with the data and/or operational instructions in main memory, the core control module 40 coordinates sending updated data to the memory 64-66 for storage.

The memory 64-66 includes one or more hard drives, one or more solid state memory chips, and/or one or more other large capacity storage devices that, in comparison to cache memory and main memory devices, is/are relatively inexpensive with respect to cost per amount of data stored. The memory 64-66 is coupled to the core control module 40 via the I/O and/or peripheral control module 52 and via one or more memory interface modules 62. In an embodiment, the I/O and/or peripheral control module 52 includes one or more Peripheral Component Interface (PCI) buses to which peripheral components connect to the core control module 40. A memory interface module 62 includes a software driver and a hardware connector for coupling a memory device to the I/O and/or peripheral control module 52. For example, a memory interface 62 is in accordance with a Serial Advanced Technology Attachment (SATA) port.

The core control module 40 coordinates data communications between the processing module(s) 42 and a network, or networks, via the I/O and/or peripheral control module 52, the network interface module(s) 60, and a network card 68 or 70. A network card 68 or 70 includes a wireless communication unit or a wired communication unit. A wireless communication unit includes a wireless local area network (WLAN) communication device, a cellular communication device, a Bluetooth device, and/or a ZigBee communication device. A wired communication unit includes a Gigabit LAN connection, a Firewire connection, and/or a proprietary computer wired connection. A network interface module 60 includes a software driver and a hardware connector for coupling the network card to the I/O and/or peripheral control module 52. For example, the network interface module 60 is in accordance with one or more versions of IEEE 802.11, cellular telephone protocols, 10/100/1000 Gigabit LAN protocols, etc.

The core control module 40 coordinates data communications between the processing module(s) 42 and input device(s) via the input interface module(s) and the I/O and/or peripheral control module 52. An input device includes a keypad, a keyboard, control switches, a touchpad, a microphone, a camera, etc. An input interface module includes a software driver and a hardware connector for coupling an input device to the I/O and/or peripheral control module 52. In an embodiment, an input interface module is in accordance with one or more Universal Serial Bus (USB) protocols.

The core control module 40 coordinates data communications between the processing module(s) 42 and output device(s) via the output interface module(s) and the I/O and/or peripheral control module 52. An output device includes a speaker, etc. An output interface module includes a software driver and a hardware connector for coupling an output device to the I/O and/or peripheral control module 52. In an embodiment, an output interface module is in accordance with one or more audio codec protocols.

The processing module 42 communicates directly with a video graphics processing module 48 to display data on the display 50. The display 50 includes an LED (light emitting diode) display, an LCD (liquid crystal display), and/or other type of display technology. The display has a resolution, an aspect ratio, and other features that affect the quality of the display. The video graphics processing module 48 receives data from the processing module 42, processes the data to produce rendered data in accordance with the characteristics of the display, and provides the rendered data to the display 50.

The DSCs provide the detected changes in electrical characteristics of the test container electrodes 16 to the test container array processing module 30 which may be a separate processing module or integrated into the processing module 42. The test container array processing module 30 processes the detected changes in electrical characteristics of the test container electrodes 16 from DSCs to determine the electrical characteristics of cells of the test system 10. For example, the test container array processing module 30 filters the data (e.g., via a bandpass filter) received from the DSCs to produce impedance values representative of the electrical characteristics of cells.

The test container array processing module 30 communicates the electrical characteristics of cells to the communication module 32. Communicating the electrical characteristics of cells to the communication module 32 may include formatting the data in a particular format with respect to the communication protocol of the communication module. The communication module 32 is operable to communicate the electrical characteristics of cells via the I/O interface to the core control module 40 where the core control module 40 can provide the data representing the electrical characteristics of cell to the video graphics processing module 48 such that the data can be displayed on display 50.

Figure 7:
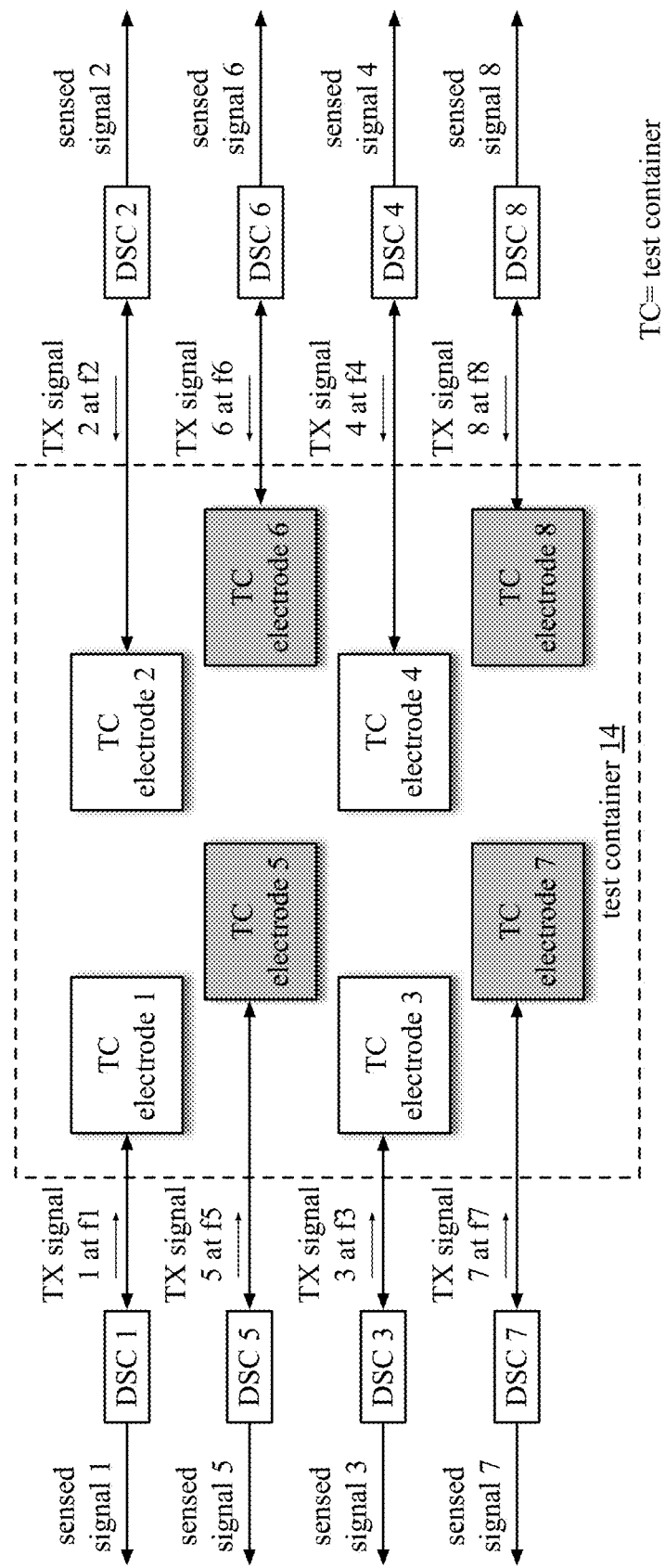
FIG. 7 is a schematic block diagram of an example of data processing of a test system in accordance with the present invention.

FIG. 7 is a schematic block diagram of an example of data processing of a test system that includes a test container 14 of the test container array and a set of drive-sense circuits (DSCs) 1-8. The test container 14 includes a set of test container (TC) electrodes 1-8. The set of TC electrodes 1-8 are shown staggered and in different colors to represent their different positions within the test container 14. Each TC electrode of the TC electrodes 1-8 is coupled to a drive-sense circuit (DSC). For example, TC electrode 1 is coupled to DSC 1.

As discussed above, the set of drive-sense circuits 1-8 are operable to detect changes in electrical characteristics of the contents of the test container. The set of drive-sense circuits (DSCs) 1-8 are coupled to one or more of a test container processing module and a test container array processing module operable to receive, from the set of drive-sense circuits 1-8, a set of changes in electrical characteristics of the test container contents (e.g., the sensed signals 1-8) and interpret the set of changes in electrical characteristics as a set of impedance values representative of electrical characteristics of biological material (e.g., a cell) present in the test container 14.

To begin data processing, the DSCs 1-8 are enabled to generate sensed signals 1-8 based on received signals from one or more of the other DSCs when only a solution 20 is present in the test container 14 (i.e., the test container does not yet include a biological material).

Figure 8:
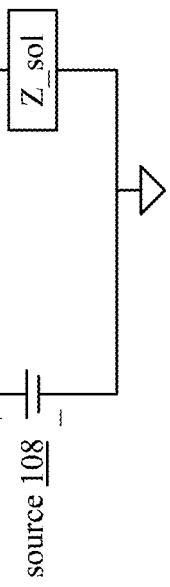
FIG. 8 is a schematic block diagram of an example a test container equivalent circuit in accordance with the present invention.

FIG. 8 illustrates the test container equivalent circuit 106, which includes a source 108 and an impedance 110. The impedance 110 in this example is representative of the impedance of the solution 20 (e.g., saline solution) present in the test container 14. The example of data processing continues in the following FIGS. 9-15.

Figure 9:
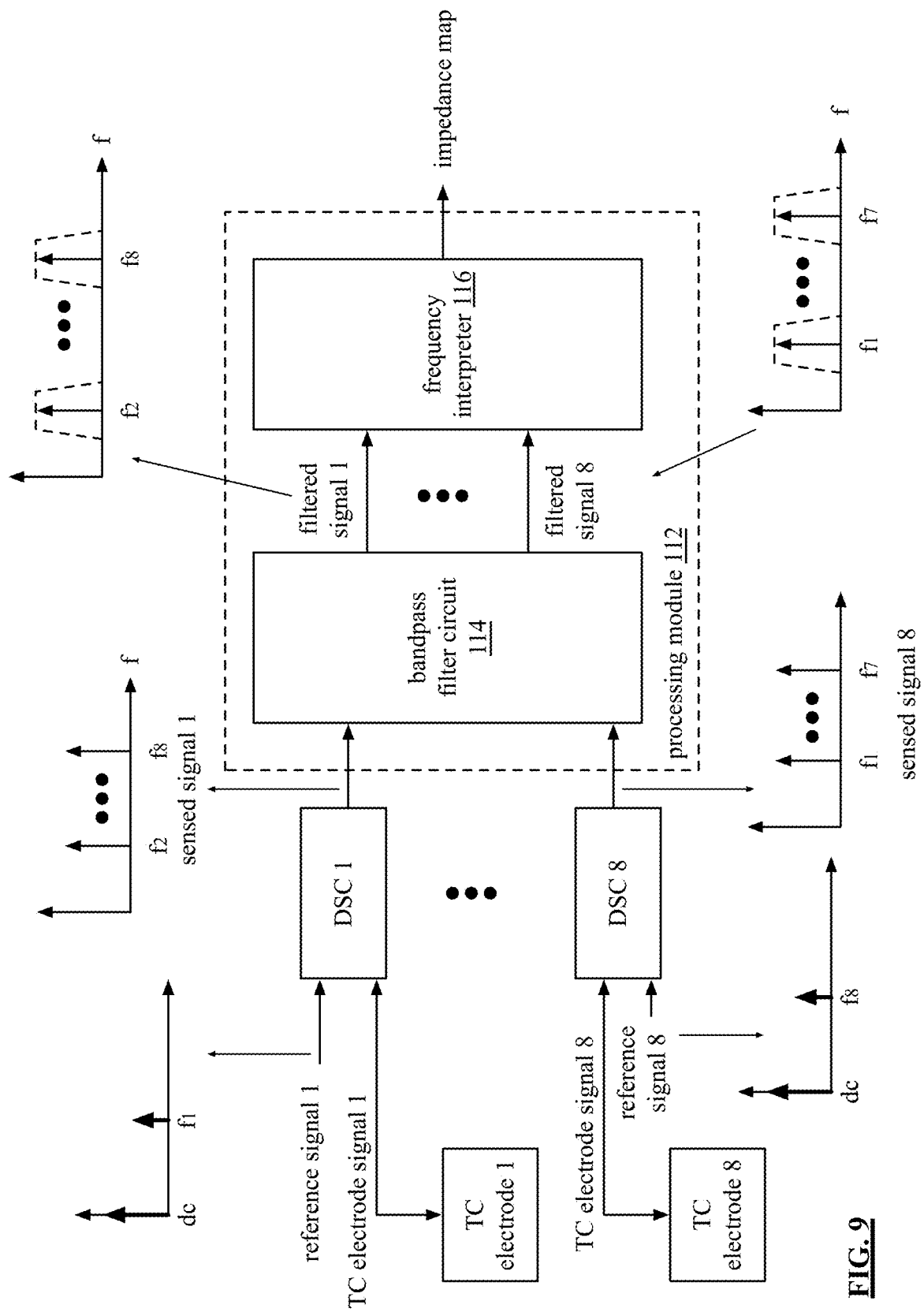
FIG. 9 is a schematic block diagram of an example of data processing of a test system in accordance with the present invention.

FIG. 9 is a schematic block diagram of an example of data processing of a test system that includes a processing module 112 (e.g., a test container processing module and/or the test container array processing module), test container (TC) electrodes 1-8 of a test container 14 of the test container array, and a set of drive-sense circuits (DSCs) 1-8. FIG. 9 continues the example of FIG. 8 where the sensed signals 1-8 are sent to a processing module (e.g., a test container processing module and/or the test container array processing module) where they are processed to determine a set of impedance values (e.g., an impedance map) representative of the electrical characteristics of the test container 14 with solution 20. The processing module 112 processes the impedance map to produce test container content electrical characteristic data with respect to the positioning of the electrodes and transmit frequencies.

The drive sense circuits 1-8 provide electrode signals 1-8 to their respective test container electrodes 1-8 and produce respective sensed signals 1-8. In an embodiment, the processing module 112 provides analog reference signals 1-8 to the drive sense circuits 1-8. For example, each drive sense circuit 1-8 receives a unique analog reference signal.

The sensed signal 1 includes frequency components at f2-f8 that corresponds to the transmit signals of DSC 2-8. As such, sensed signal 1 includes 7 different frequencies, which will produce 7 different impedance values. For example, impedance 1 is the impedance between DSC 1's electrode and DSC 2's electrode at frequency f2; impedance 2 is the impedance between DSC 1's electrode and DSC 3's electrode at frequency f3; and so on. The sensed signal 2 includes frequency components at f1, and $f_3$-$f_8$ that corresponds to transmit signals of DSC 1, and DSCs 3-8. As such, sensed signal 7 includes 7 different frequencies, which will produce 7 different impedance values. For example, impedance 1 is the impedance between DSC 2's electrode and DSC 1's electrode at frequency f1; impedance 2 is the impedance between DSC 2's electrode and DSC 3's electrode at frequency f3; and so on.

The processing module 112 includes a bandpass filter 114 and a frequency interpreter 116. The bandpass filter circuit 114 passes (i.e., substantially unattenuated) signals in a bandpass region (e.g., tens of Hertz to hundreds of thousands of Hertz, or more) centered about frequencies $f_1$-$f_8$ and attenuates signals outside of the bandpass regions. The bandpass filter circuit 114 includes one or more digital filters, where a digital filter is implemented as a cascaded integrated comb (CIC) filter, a finite impulse response (FIR) filter, an infinite impulse response (IIR) filter, a Butterworth filter, a Chebyshev filter, an elliptic filter, etc.

In this example, the processing module 112 filters the sensed signals 1-8 at different times in order to use the bandpass filter circuit 114 in a round robin fashion on the sensed signals 1-8. The processing module 112 may receive sensed signals 1-8 at the same or different times. For example, the processing module 112 receives sensed signals 1-8 from DSCs 1-8 and the bandpass filter 114 filters sensed signal 1 at time T1 to produce a filtered signal 1, filters sensed signal 2 at time T2 to produce a filtered signal 2, filters sensed signal 3 at time T3 to produce a filtered signal 3, filters sensed signal 4 at time T4 to produce a filtered signal 4, filters sensed signal 5 at time T5 to produce a filtered signal 5, filters sensed signal 6 at time T6 to produce a filtered signal 6, filters sensed signal 7 at time T7 to produce a filtered signal 7, and filters sensed signal 8 at time T8 to produce a filtered signal 8.

The frequency interpreter 116 receives the filtered signal 1 at T1 and interprets it to render a first set of impedance values. As an example, the frequency interpreter 116 is a processing module, or portion thereof, that executes a function to convert the signal components of filtered signal 1 into the first set of impedance values, which are actual impedance values, relative impedance values (e.g., in a range), and/or difference impedance values (e.g., is the difference between a default impedance value and a sensed impedance value). As another example, the frequency interpreter 116 utilizes a look up table where the signal components of the filtered signal 1 are indexes for the table.

The frequency interpreter 116 produces eight sets of impedances (e.g., one for each DSC) and further processes them to produce an impedance map of the test container per sampling interval. As an alternative to time multiplexing the use of eight digital filters within the bandpass filter circuit 114, the bandpass filter circuit 114 includes 56 digital filters; seven for each sensed signal.

Figure 9A:
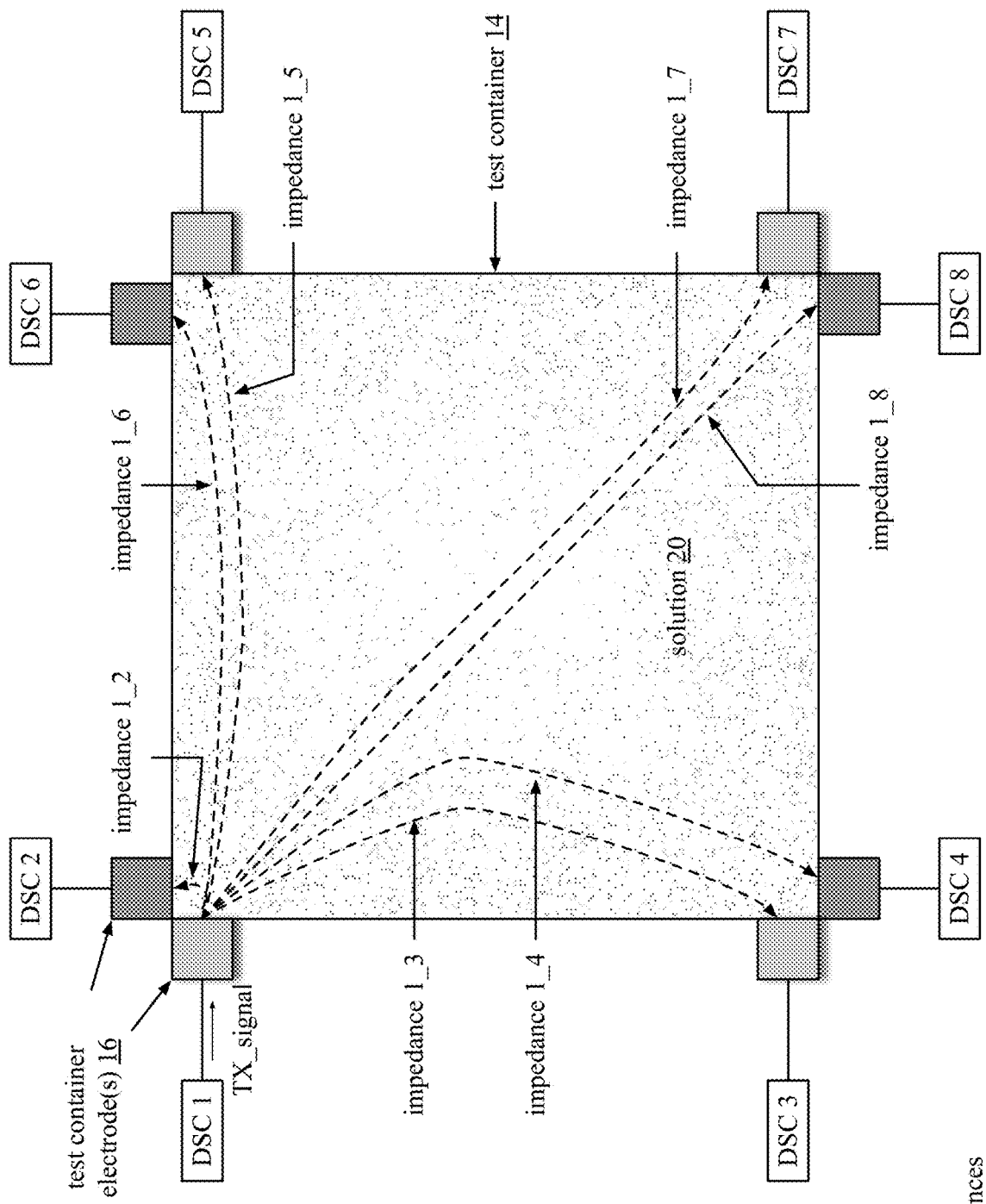
FIG. 9A is a schematic block diagram of an example of a first set of impedances of an impedance map in accordance with the present invention.

FIG. 9A is a schematic block diagram of an example of a first set of impedances of an impedance map. The first set of impedances corresponds to a sensed signal 1 produced by drive sense circuit (DSC) 1. DSCs 1-8 transmit signals at frequencies $f_1$-$f_8$. The sensed signal 1 includes frequency components at $f_2$-$f_8$ corresponding to the transmit signals of DSC 2-8. Sensed signal 1 includes 7 different frequencies that produce 7 different impedance values.

For example, impedance 1_2 is the impedance between DSC 1's electrode and DSC 2's electrode at frequency $f_2$; impedance 1_3 is the impedance between DSC 1's electrode and DSC 3's electrode at frequency f3; impedance 1_4 is the impedance between DSC 1's electrode and DSC 4's electrode at frequency f4; impedance 1_5 is the impedance between DSC 1's electrode and DSC 5's electrode at frequency f5; impedance 1_6 is the impedance between DSC 1's electrode and DSC 6's electrode at frequency f6; impedance 1_7 is the impedance between DSC 1's electrode and DSC 7's electrode at frequency f7; and impedance 1_8 is the impedance between DSC 1's electrode and DSC 8s electrode at frequency f8.

Figure 9B:
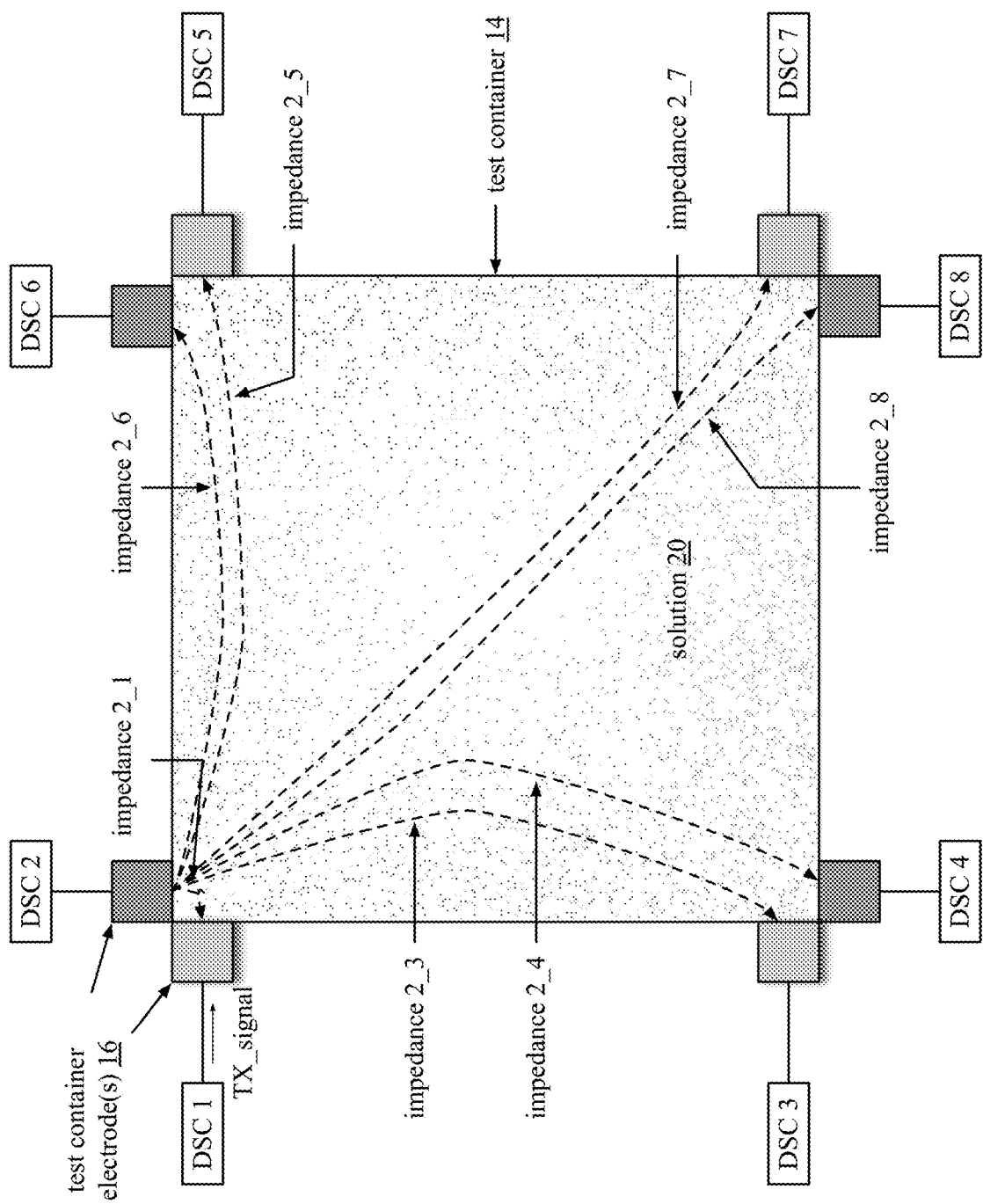
FIG. 9B is a schematic block diagram of an example of a second set of impedances of an impedance map in accordance with the present invention.

FIG. 9B is a schematic block diagram of an example of a second set of impedances of an impedance map. The second set of impedances corresponds to a sensed signal 2 produced by drive sense circuit (DSC) 2. DSCs 1-8 transmit signals at frequencies $f_1$-$f_8$. The sensed signal 2 includes frequency components at $f_1$ and $f_3$-$f_8$ corresponding to the transmit signals of DSC 1 and DSCs 3-8. Sensed signal 2 includes 7 different frequencies that produce 7 different impedance values.

For example, impedance 2_1 is the impedance between DSC 2's electrode and DSC 1's electrode at frequency f1; impedance 2_3 is the impedance between DSC 2's electrode and DSC 3's electrode at frequency f3; impedance 2_4 is the impedance between DSC 2's electrode and DSC 4's electrode at frequency f4; impedance 2_5 is the impedance between DSC 2's electrode and DSC 5's electrode at frequency f5; impedance 2_6 is the impedance between DSC 2's electrode and DSC 6's electrode at frequency f6; impedance 2_7 is the impedance between DSC 2's electrode and DSC 7's electrode at frequency f7; and impedance 2_8 is the impedance between DSC 2's electrode and DSC 8's electrode at frequency f8.

Figure 9C:
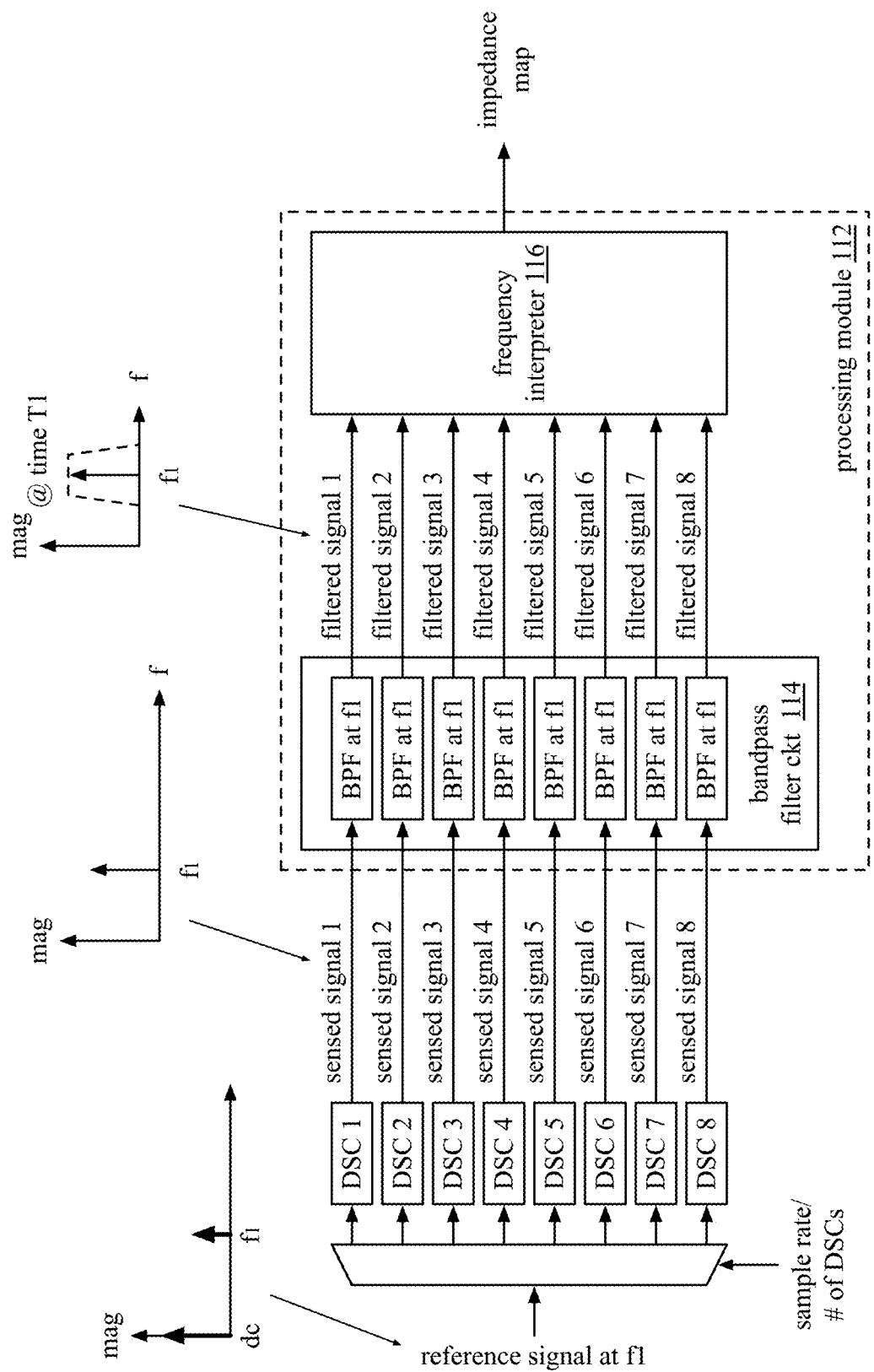
FIG. 9C is a schematic block diagram of another example of data processing of a test system in accordance with the present invention.

FIG. 9C is a schematic block diagram of another example of data processing of a test system that includes a processing module 112 (e.g., a test container processing module and/or the test container array processing module), a set of drive-sense circuits (DSCs) 1-8, and a multiplexor. The processing module 112 includes a bandpass filter circuit 114 and a frequency interpreter 116.

FIG. 9C operates similarly to FIG. 9 except that the multiplexor selects a reference signal input for each DSC such that the DSCs transmit signals one at a time using the same frequency. For example, a reference signal at a frequency f1 is selected as the transmit signal for each DSC. The sensed signals 1-8 each include a frequency components at $f_1$ corresponding to the transmit signal produced by the DSC that is currently transmitting. A set of 7 impedances are generated per cycle of multiplexing in this example.

The bandpass filter circuit 114 passes (i.e., substantially unattenuated) signals in a bandpass region centered about frequency $f_1$ and attenuates signals outside of the bandpass regions. In an example, when DSC 1 is transmitting, the sensed signals 2-8 includes frequency components at $f_1$ that corresponds to the transmit signal of DSC 1. The bandpass filter circuit 114 filters the set of sensed signals 2-8 at the frequency $f_1$ to produce a set of filtered signals 2-8 at the frequency $f_1$. The frequency interpreter 116 receives the filtered signals 2-8 and interprets it to render a first set of impedance values. As such, 7 different impedance values are provided at the same frequency.

Figure 10:
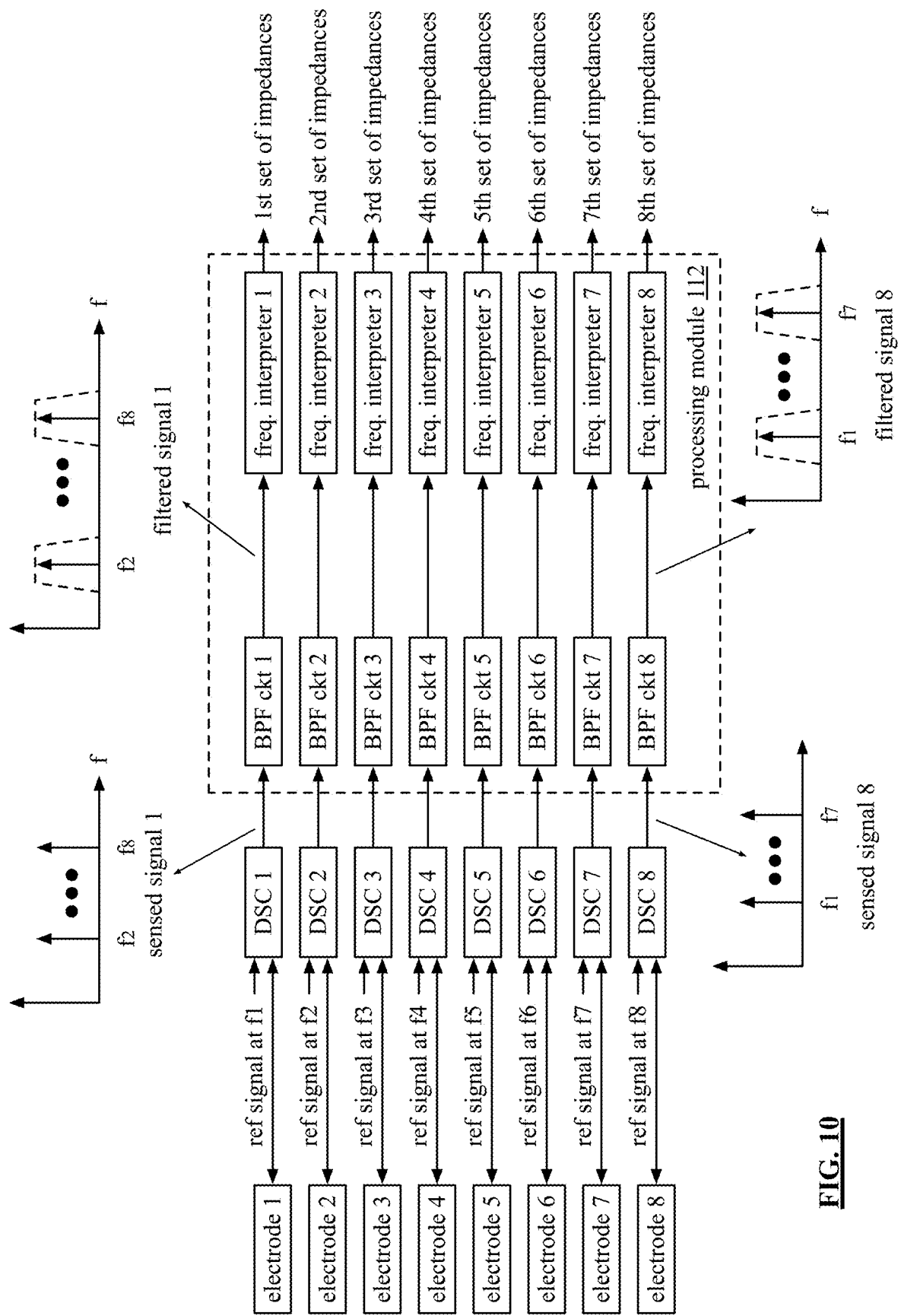
FIG. 10 is a schematic block diagram of an example of data processing of a test system in accordance with the present invention.

FIG. 10 is a schematic block diagram of an example of data processing of a test system that includes a processing module 112 (e.g., a test container processing module and/or the test container array processing module), test container (TC) electrodes 1-8 of a test container 14 of the test container array, and a set of drive-sense circuits (DSCs) 1-8.

FIG. 10 operates similarly to FIG. 9 except that the processing module 112 includes a plurality of narrow bandpass filters 1-8 (BPF ckts 1-8) and a plurality of frequency interpreters 1-8. In this embodiment, the processing module 112 receives sensed signals 1-8 from the DSCs 1-8 and processes the sensed signals 1-8 to produce eight sets of impedances (one from each DSC).

FIG. 11 is a schematic block diagram of an example of a test container impedance map 118. As discussed in FIGS. 8-10, a processing module of a test system (e.g., one or more of a test container processing module and a test container array processing module) is operable to convert a sensed signal from a drive-sense circuit into a set of impedances values (e.g., one or more impedance values). The processing module is further operable to generate and store a test container impedance map 118 that associates the sets of impedance values to their respective electrodes and physical placements within the testing container 14.

As shown, each set of impedances includes 7 impedances: a DSC receives the transmissions from the other 7 DSCs to produce a set of impedances. Note that the shaded impedances have a corresponding non-shaded impedance. For example, impedance 7-1 has a corresponding impedance 1-7. These impedance will be different since their reference signals are different (e.g., frequencies f1 and f7). While the impedances and frequencies are different, the resistive and reactive components between the first and seventh electrodes should be the same. Thus, from one or more of the two equations, the resistive and reactive components between the first and seventh electrodes can be readily determined. For example, the resistance, capacitance, and/or inductance between the first and seventh electrodes can be readily determined (e.g., V=I*R, impedance of a capacitor is $1/2\pi fC$, and the impedance of an inductor is $2\pi fL$).

Figure 12:
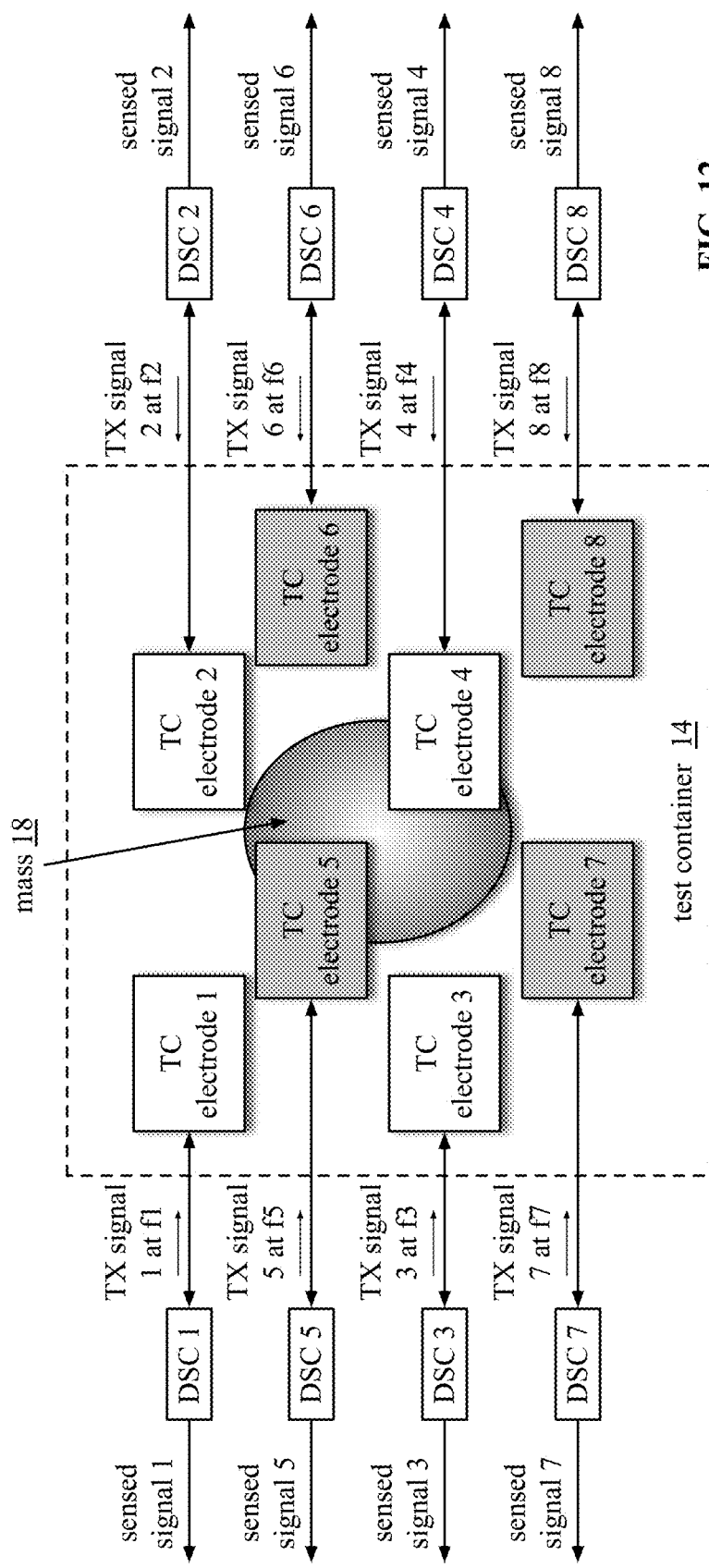
FIG. 12 is a schematic block diagram of an example of data processing of a test system in accordance with the present invention.

FIG. 12 is a schematic block diagram of an example of data processing of a test system that includes a test container 14 of the test container array and a set of drive-sense circuits (DSCs) 1-8. This example is similar to the example of FIG. 8, with a difference being that a mass is added to the test container 14. For example, the mass 18 is one or more cells and/or one or more portions of a cell. Here, one or more cells 18 are added to the test container 14. As in FIG. 8, the DSCs 1-8 are enabled to generate sensed signals 1 through 8. In alternative embodiment, the cells are grown in the test container 14 filled with the solution. Note that it can take months to grow a group of cells to be ready for testing.

Figure 12A:
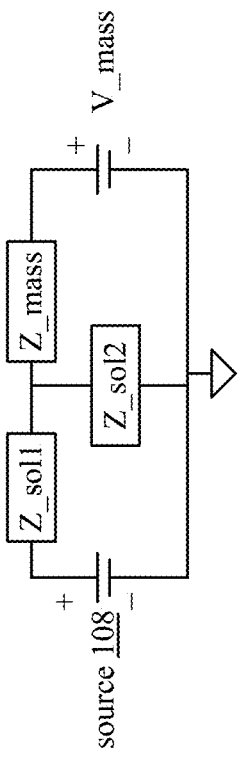
FIG. 12A is a schematic block diagram of another example a test container equivalent circuit in accordance with the present invention.

FIG. 12A is a schematic block diagram of the test container equivalent circuit 106, which includes a source 108 (e.g., a transmitting DSC), a mass 18 source due to the voltage potential of the mass and an impedance 110. The impedance 110 in this example is representative of the impedance of a first portion of the solution 20 (e.g., saline solution) and the impedance of the mass 18 (e.g., cell membrane capacitance and resistance) in parallel with a second portion of the solution added to the test container 14.

Figure 13:
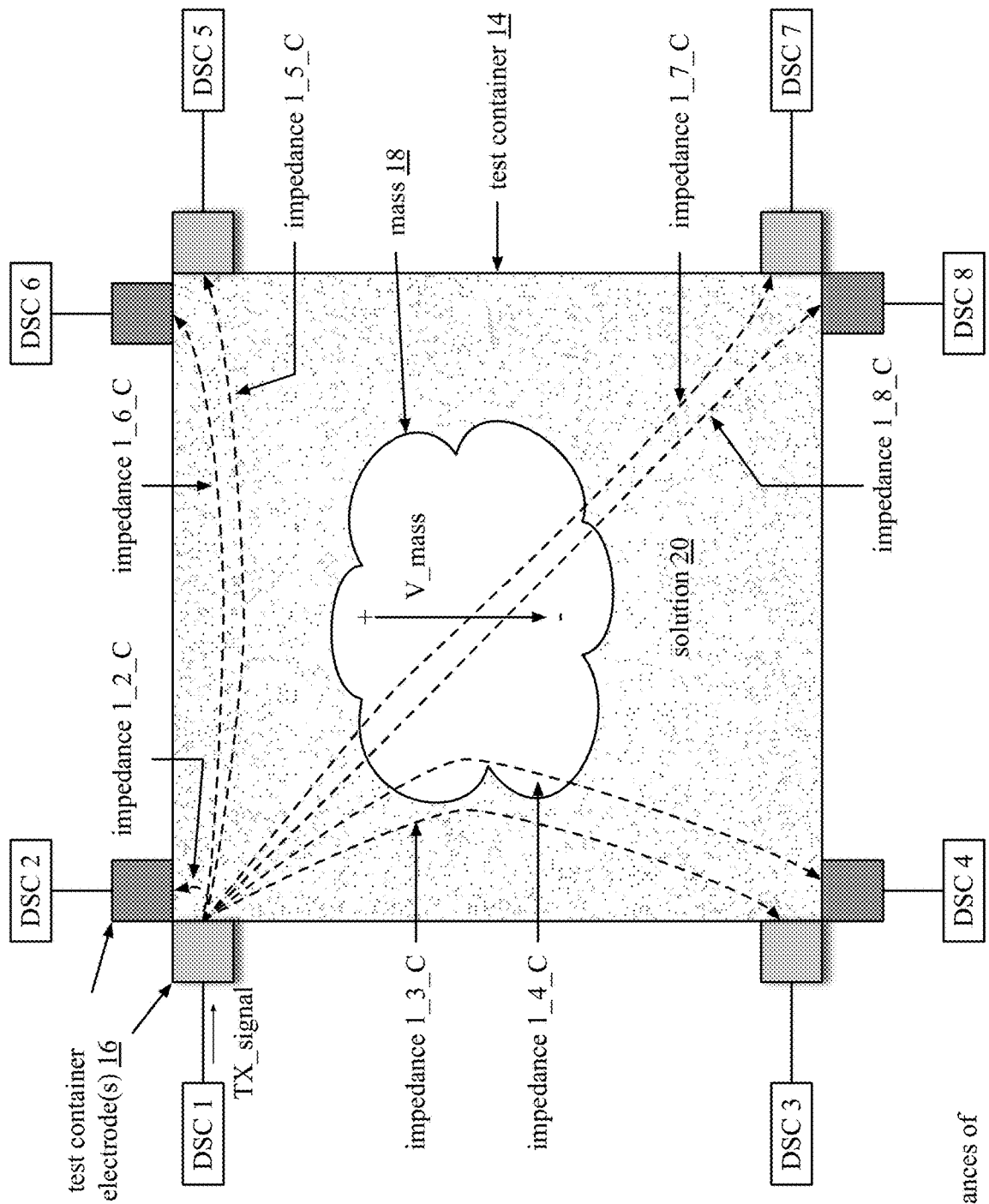
FIG. 13 is a schematic block diagram of an example of comparing test container impedance maps in accordance with the present invention.

FIG. 13 is a schematic block diagram of an example of a first set of impedances of an impedance map 118-1 for the example of FIG. 12. The first set of impedances is derived when the drive-sense circuit (DSC) 1 transmits a signal at f1 to the other DSCs (e.g., 2-7). As previously discussed, each of DSC 2-7 generates a sensed signal based on receiving the transmitted signal at f1, where an impedance is generated therefrom. For example, the sensed signal produced by DSC 7 is converted into an impedance 1_7_C, where the 1 indicates that the source of the signal is DSC 1, the 7 indicates that DSC 7 is recipient of the signal, and the C indicates that a mass 18 is present. Similarly, the sensed signal produced by DSC 4 is converted into impedance 1_4_C. In this example, the voltage produced by the mass (V_mass) is positively coupled in series with the impedance of the solution and the impedance of the mass per the equivalent circuit of FIG. 12A.

Figure 13A:
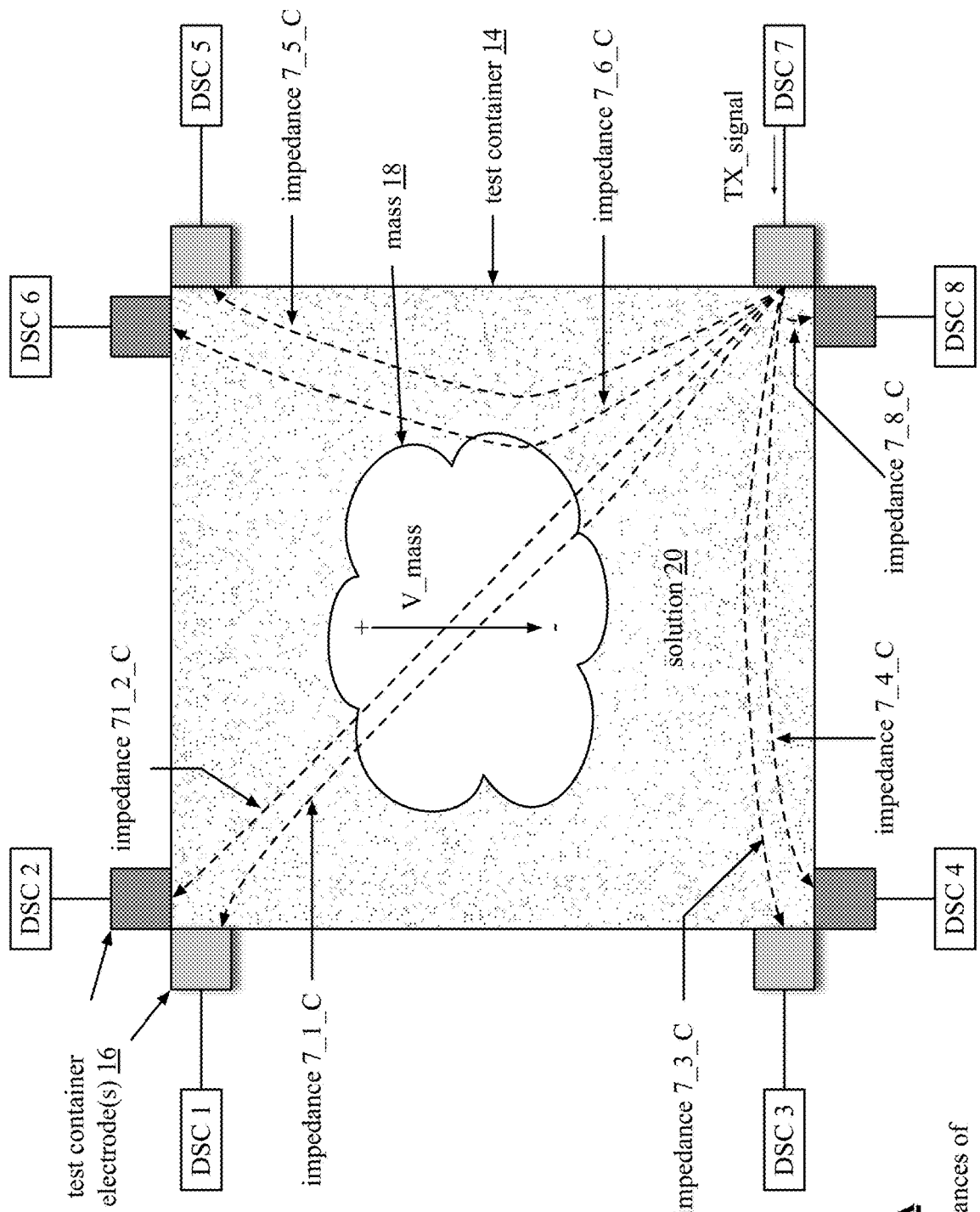
FIG. 13A is a schematic block diagram of another example of comparing test container impedance maps in accordance with the present invention.

FIG. 13A is a schematic block diagram of an example of a seventh set of impedances of an impedance map 118-1 for the example of FIG. 12. The seventh set of impedances is derived when the DSC 7 transmits a signal at f7 (or at f1 depending on time and frequency multiplexing patterns used for transmitting signals) to the other DSCs (e.g., 1-6, and 8). As previously discussed, each of DSC 1-6, and 8 generates a sensed signal based on receiving the transmitted signal at f7, where an impedance is generated therefrom. For example, the sensed signal produced by DSC 1 is converted into an impedance 7_1_C, where the 7 indicates that the source of the signal is DSC 7, the 1 indicates that DSC 1 is the recipient of the signal, and the C indicates that a mass is present. Similarly, the sensed signal produced by DSC 6 is converted into impedance 7_6_C. In this example, the voltage produced by the mass (V_mass) is negatively coupled in series with the impedance of the solution and the impedance of the mass.

The processing module of system 10 is operable to compare the impedance map 118 (solution only) with the impedance map 118-1 (solution and mass) to determine the electrical characteristics of the mass 18. The electrical characteristics of the mass 18 include impedance, membrane potential (if one or more cells), size, shape, density, movement, orientation, cell excitation (e.g., beat amplitude), etc.

FIGS. 13B-13E are schematic block diagrams of equivalent circuits of the embodiment of FIG. 12 with respect to the drive-sense circuit (DSC) 1 as the source of the transmit signal. FIG. 13B includes DSC 1 transmitting a TX signal at a frequency f1. The DSC 7 receives an RX signal at f1 and generates a sensed signal based on receiving the transmitted signal at f1, where an impedance is generated therefrom. For example, the sensed signal produced by DSC 7 is converted into an impedance 1_7_C, where the 1 indicates that the source of the signal is DSC 1, the 7 indicates that DSC 7 is the recipient of the signal, and the C indicates that a mass is present.

FIG. 13C includes DSC 1 transmitting a TX signal at a frequency f1. The DSC 8 receives an RX signal at f1 and generates a sensed signal based on receiving the transmitted signal at f1, where an impedance is generated therefrom. For example, the sensed signal produced by DSC 8 is converted into an impedance 1_8_C, where the 1 indicates that the source of the signal is DSC 1, the 8 indicates that DSC 7 is the recipient of the signal, and the C indicates that a mass is present.

FIG. 13D includes DSC 1 transmitting a TX signal at a frequency f1. The DSC 3 receives an RX signal at f1 and generates a sensed signal based on receiving the transmitted signal at f1, where an impedance is generated therefrom. For example, the sensed signal produced by DSC 3 is converted into an impedance 1_3_C, where the 1 indicates that the source of the signal is DSC 1, the 3 indicates that DSC 3 is the recipient of the signal, and the C indicates that a mass is present.

FIG. 13E includes DSC 1 transmitting a TX signal at a frequency f1. The DSC 4 receives an RX signal at $f_1$ and generates a sensed signal based on receiving the transmitted signal at f1, where an impedance is generated therefrom. For example, the sensed signal produced by DSC 4 is converted into an impedance 1_4_C, where the 1 indicates that the source of the signal is DSC 1, the 4 indicates that DSC 4 is the recipient of the signal, and the C indicates that a mass is present.

FIGS. 13F-13i are schematic block diagrams of equivalent circuits of the embodiment of FIG. 12 with respect to the drive-sense circuit (DSC) 7 as the source of the transmit signal. FIG. 13F includes DSC 7 transmitting a TX signal at a frequency f7. The DSC 1 receives an RX signal at f7 and generates a sensed signal based on receiving the transmitted signal at f7, where an impedance is generated therefrom. For example, the sensed signal produced by DSC 1 is converted into an impedance 7_1_C, where the 7 indicates that the source of the signal is DSC 7, the 1 indicates that DSC 1 is the recipient of the signal, and the C indicates that a mass is present.

FIG. 13G includes DSC 7 transmitting a TX signal at a frequency f7. The DSC 2 receives an RX signal at f7 and generates a sensed signal based on receiving the transmitted signal at f7, where an impedance is generated therefrom. For example, the sensed signal produced by DSC 2 is converted into an impedance 7_2_C, where the 7 indicates that the source of the signal is DSC 7, the 2 indicates that DSC 2 is the recipient of the signal, and the C indicates that a mass is present.

FIG. 13H includes DSC 7 transmitting a TX signal at a frequency f7. The DSC 6 receives an RX_signal at f7 and generates a sensed signal based on receiving the transmitted signal at f7, where an impedance is generated therefrom. For example, the sensed signal produced by DSC 6 is converted into an impedance 7_6_C, where the 7 indicates that the source of the signal is DSC 7, the 6 indicates that DSC 6 is the recipient of the signal, and the C indicates that a mass is present.

FIG. 13i includes DSC 7 transmitting a TX signal at a frequency f7. The DSC 5 receives an RX_signal at f7 and generates a sensed signal based on receiving the transmitted signal at f7, where an impedance is generated therefrom. For example, the sensed signal produced by DSC 5 is converted into an impedance 7_5_C, where the 7 indicates that the source of the signal is DSC 7, the 5 indicates that DSC 5 is the recipient of the signal, and the C indicates that a mass is present.

Figure 14:
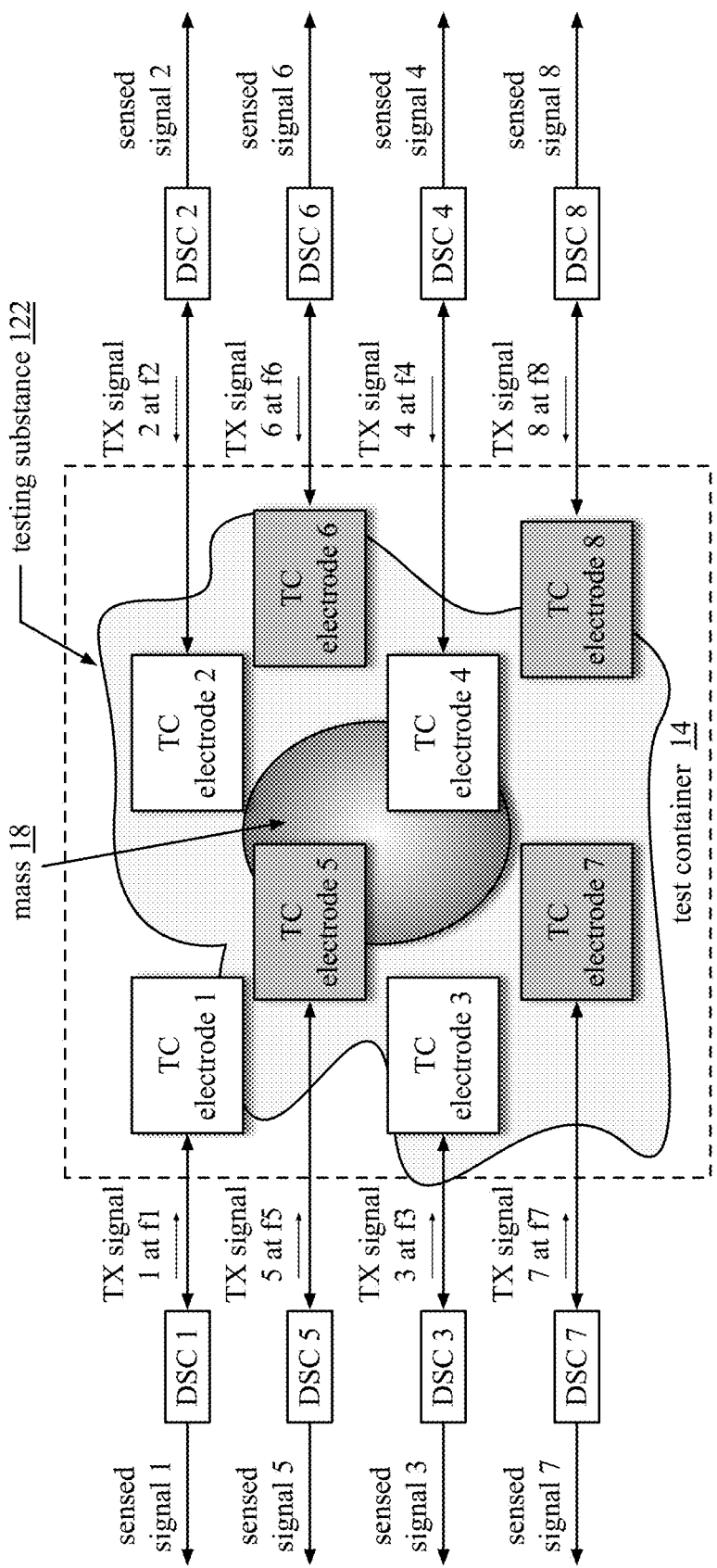
FIG. 14 is a schematic block diagram of an example of data processing of a test system in accordance with the present invention.

FIG. 14 is a schematic block diagram of an example of data processing of a test system that is similar to the example of FIG. 12 with the addition of a testing substance 122 included in the test container 14. The testing substance 122 may be one or more of an FDA approved prescription drug, an over the counter drug, an allergen, a not-yet-approved FDA drug, a food, a chemical, a pesticide, a combination of one or more drugs. In practice, there is no limit on the particular nature of the testing substance 122.

The purpose of adding the testing substance to the test container that already contains a solution 20 and a mass 18 (e.g., a biological material such as cells) is to determine how the mass reacts to the testing substance. With the use of testing system disclosed herein, dyes and electric field enhancers are not required, which kills the biological material. Because the testing system 10 is capable of measuring very small voltages (e.g., from a few nano-volts to tens of pico-volts) and/or very small currents (e.g., a few nano-amps to tens of pico-amps), a plethora of testing options are now available. Such a testing system 10 enables significant advancements in individualized medicine.

For example, a variety of a person's cells (e.g., skin, heart, lung, kidney, etc.) can be exposed to a wide variety of testing substances to determine, not only how the cell immediately reacts, but how does it react over time to the testing substances. This last aspect was not previously obtaining because the dyes and the electric field enhancer killed the cells.

Figure 15A:
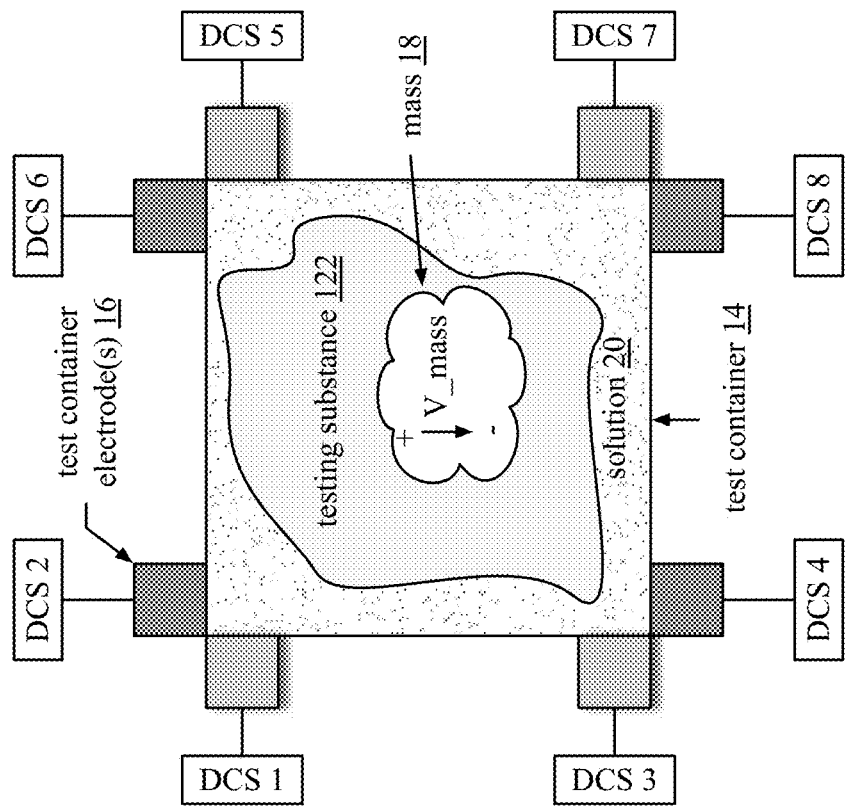
FIGS. 15-15C are schematic block diagrams of one or more examples of comparing test container impedance maps in accordance with the present invention.
Figure 15:
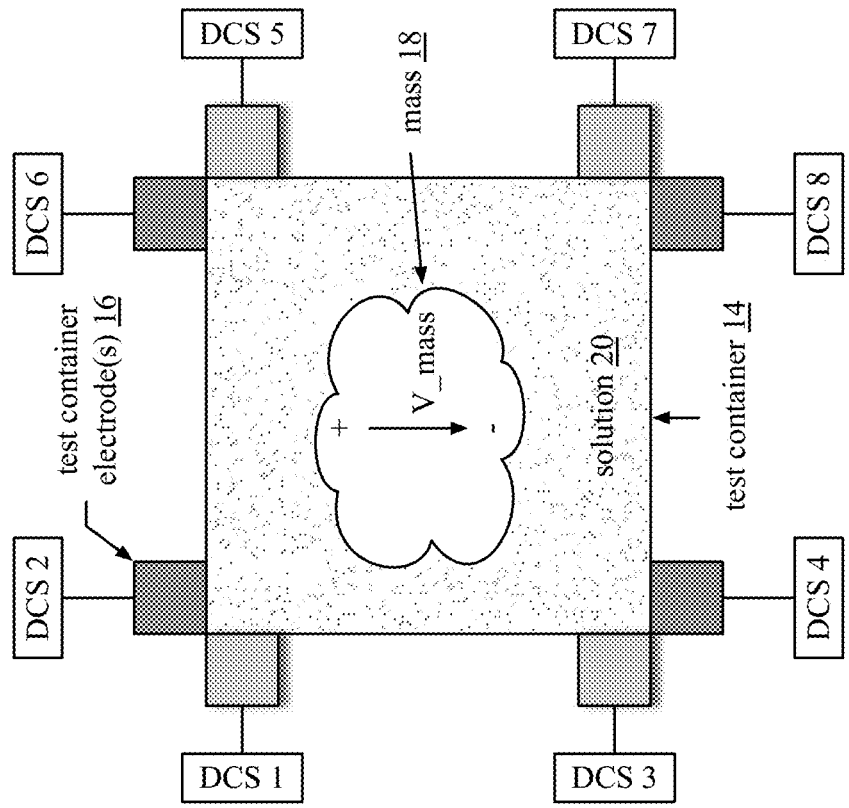
Figure 15C:
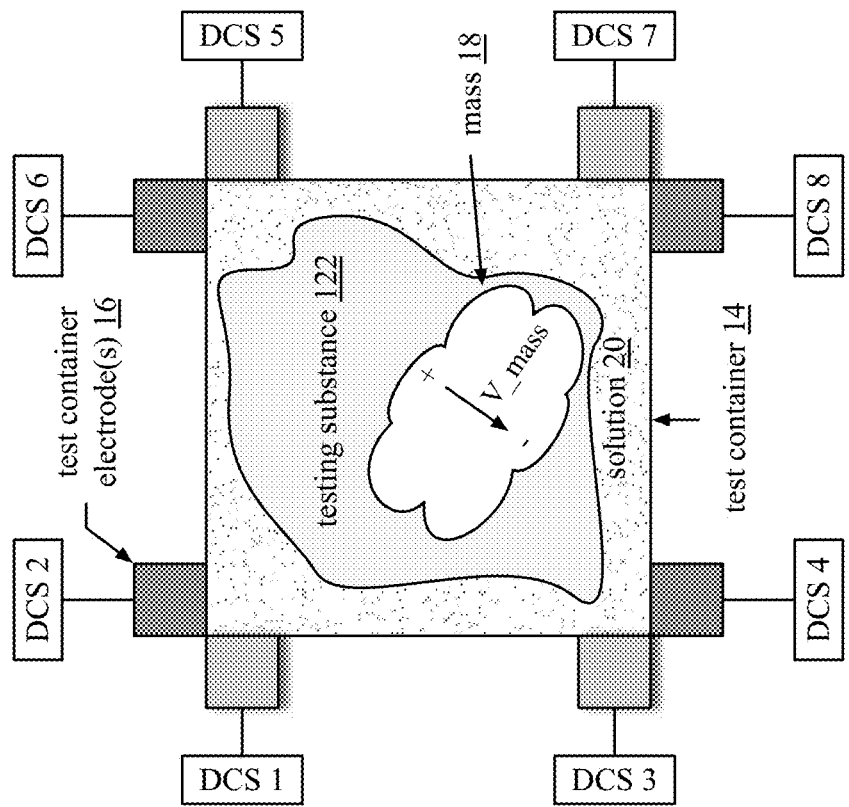

FIGS. 15-15C are schematic block diagrams of one or more examples of comparing test container impedance maps. FIG. 15 shows the test container including the solution and the mass 18, which will have an impedance map 118-1 as discussed with reference to FIGS. 13-13I.

When the testing substance 122 is added to the test container 14, another test container impedance map is generated using similar methods as previously discussed. With reference to FIG. 15A, the testing substance 122 caused the mass to shrink and its voltage to decrease. This will cause an impedance change, which is reflected in the impedance map for this test. The processing module of the testing system compares the impedance map of the mass without a testing substance to the impedance map of the mass with the testing substance to determine the changes to the mass. As time passes, multiple time-stamped impedance maps are generated for the mass exposed to the testing substance to determine how the mass reacts to the testing substance over time.

Figure 15B:
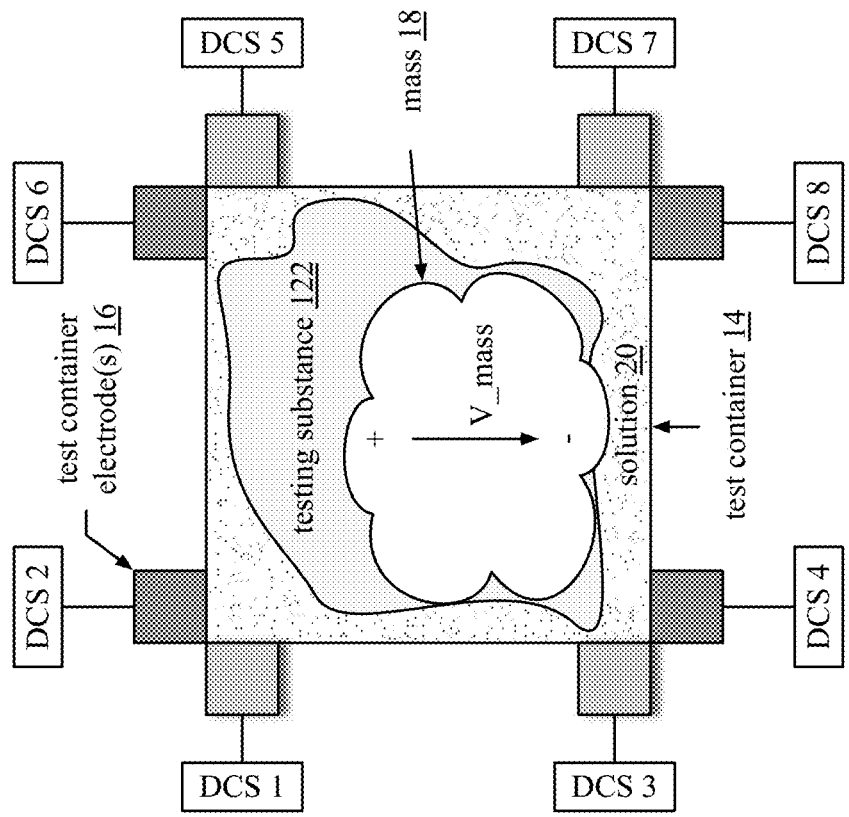

FIG. 15B is a diagram of an example of the mass growing and its voltage increasing as a result of the testing substance. This too causes an impedance change, which is reflected in the impedance map for this test. The processing module of the testing system compares the impedance map of the mass without a testing substance to the impedance map of the mass with the testing substance to determine the changes to the mass.

FIG. 15C is a diagram of an example of the mass changing in more or more manners. For example, the mass changes its shape. As another example, the orientation of the mass changes. As yet another example, the mass' voltage and/or impedance changes. Each of the changes causes an impedance change, which is reflected in the impedance map for this test. The processing module of the testing system compares the impedance map of the mass without a testing substance to the impedance map of the mass with the testing substance to determine the changes to the mass.

With the changes to the mass (e.g., cells) readily detectable by the testing system, medical professionals can interpret the changes to determine if the testing substance is beneficial to an individual and/or harmful to the individual. In addition, the level of benefit and/or harm can be determined. In another use case, a cell may be exposed to a combination of testing substances to determine the cell's reaction thereto.

Figure 16:
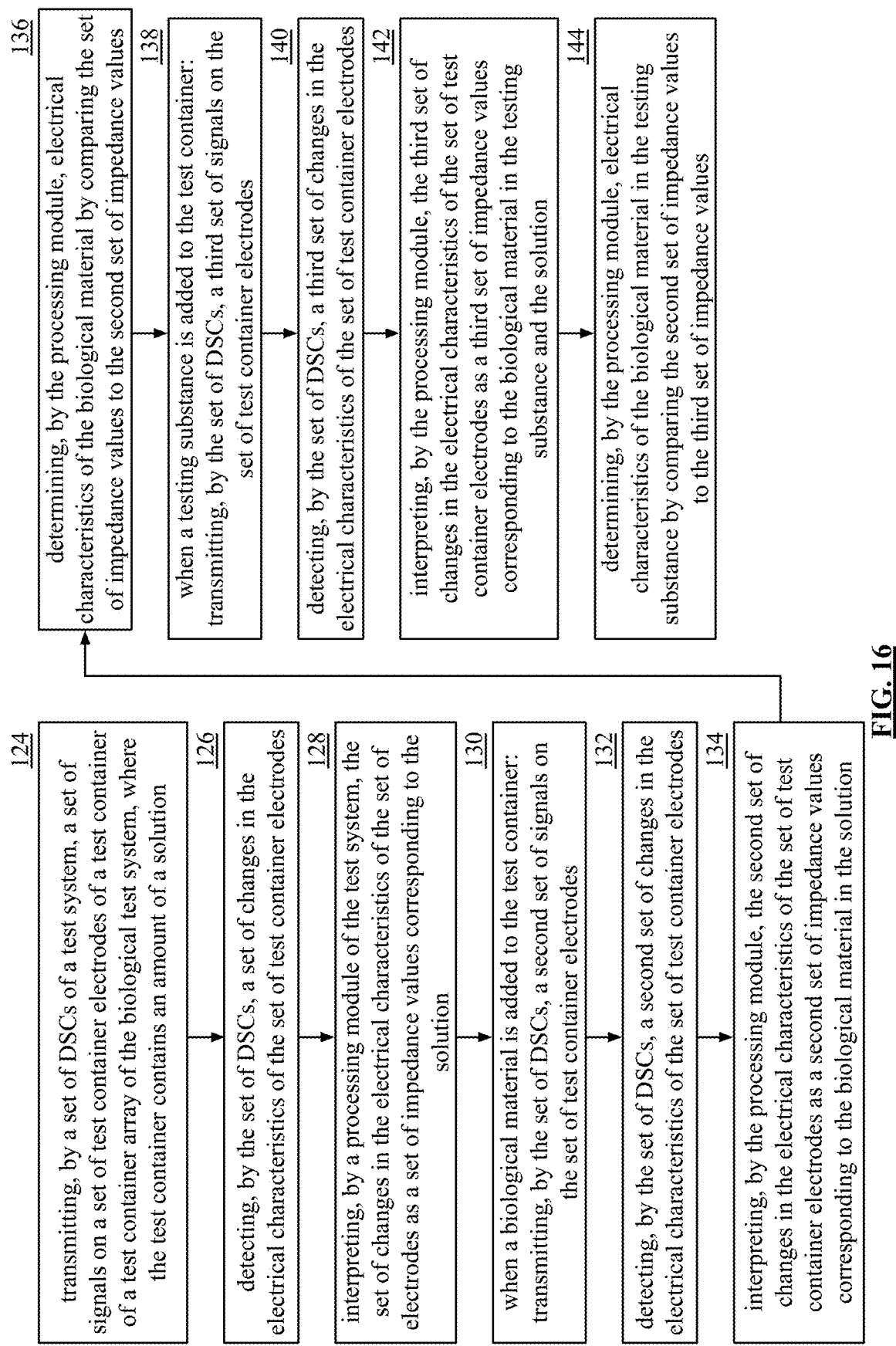
FIG. 16 is a logic diagram of an example of a method of data processing of a test system in accordance with the present invention.

FIG. 16 is a logic diagram of an example of a method of data processing of the test system. The method begins with step 124 a set of drive-sense circuits (DSCs) of a plurality of DSCs of a test system transmits a set of signals on a set of test container electrodes of a test container of a test container array of the test system. The test container contains an amount of a solution. The solution maintains the integrity and viability of biological material (e.g., a cell) and negligibly interferes with testing substances or biochemical reactions. For example, the solution is a saline solution, a preservative, a cell culture solution, etc.

The method continues with step 126 where the set of DSCs detect a set of changes in electrical characteristics of the set of test container electrodes. The method continues with step 128 where a processing module of the test system interprets the set of changes in the electrical characteristics of the set of electrodes as a set of impedance values corresponding to the solution. The processing module interprets the set of changes in the electrical characteristics of the set of electrodes as a set of impedance values as described with reference to FIGS. 8-10.

The method continues with step 130 where, when biological material is added to the test container, the set of DSCs transmit a second set of signals on the set of test container electrodes. The biological material includes one or more cells and/or one or more portions of a cell (e.g., a section of cell membrane). The method continues with step 132 where the set of DSCs detect a second set of changes in the electrical characteristics of the set of test container electrodes. The method continues with step 134 where the processing module interprets the second set of changes in the electrical characteristics of the set of electrodes as a second set of impedance values corresponding to the biological material in the solution. The processing module interprets the second set of changes in the electrical characteristics of the set of electrodes as the second set of impedance values corresponding to the biological material in the solution using similar method to those described with reference to FIGS. 8-10.

The method continues with step 136 where the processing module determines the electrical characteristics of the biological material by comparing the set of impedance values corresponding to the solution to the second set of impedance values corresponding to the biological material in the solution. The electrical characteristics of the biological material include cell impedance, membrane potential, size, shape, density, movement, orientation, cell excitation (e.g., beat amplitude), etc.

The method continues with step 138 where, when a testing substance is added to the test container, the set of DSCs transmit a third set of signals on the set of test container electrodes. A testing substance may be a chemical such as a drug or pesticide. The method continues with step 140 where the set of DSCs detect a third set of changes in the electrical characteristics of the set of test container electrodes. The method continues with step 142 where the processing module interprets the third set of changes in the electrical characteristics of the set of electrodes as a third set of impedance values corresponding to the biological material in the testing substance and the solution. The processing module interprets the third set of changes in the electrical characteristics of the set of electrodes as the third set of impedance values corresponding to the biological material in the solution using similar method to those described with reference to FIGS. 8-10.

The method continues with step 144 where the processing module determines electrical characteristics of the biological material in the testing substance by comparing the second set of impedance values corresponding to the biological material in the solution with the third set of impedance values corresponding to the biological material in the testing substance and the solution.

Figure 17:
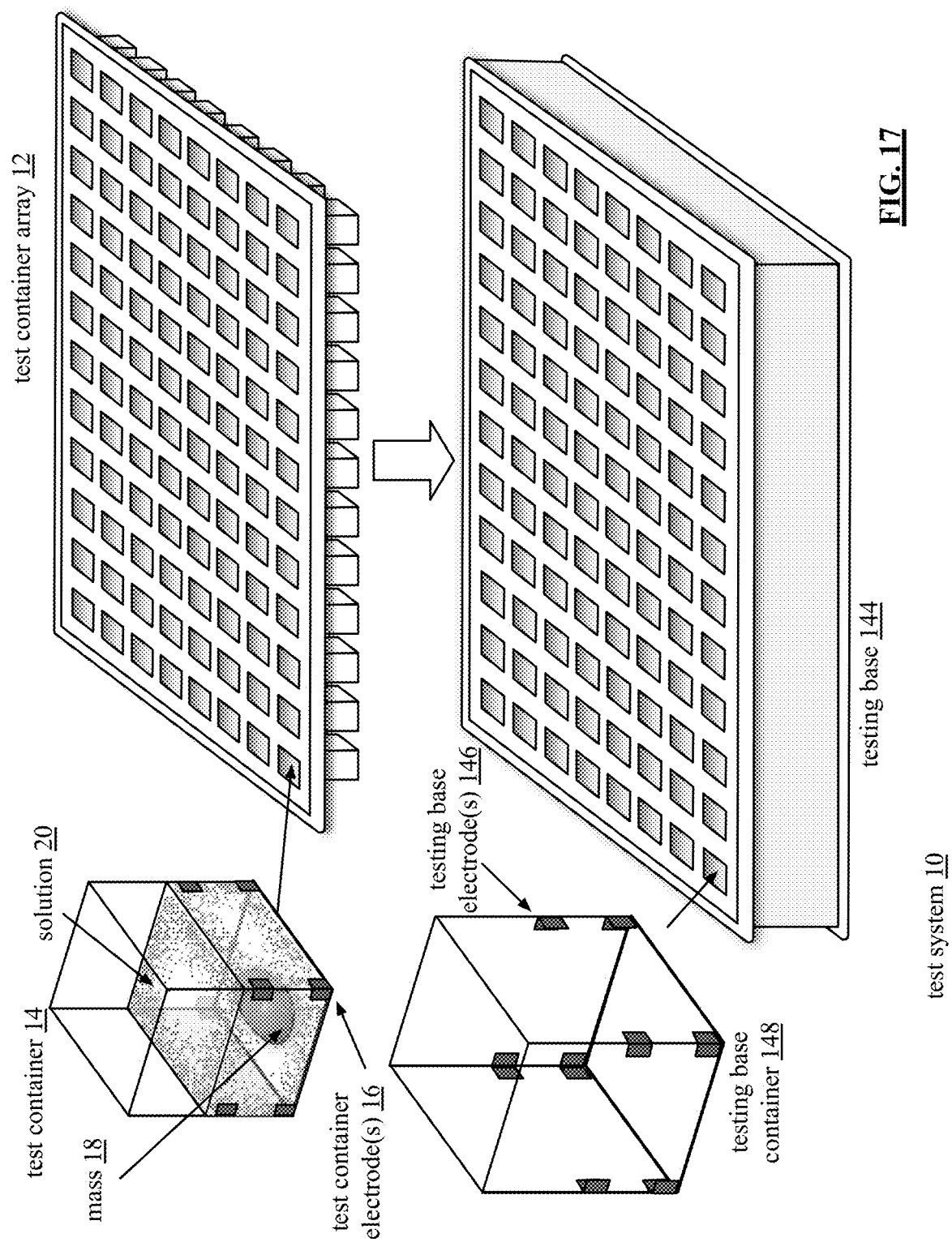
FIG. 17 is a schematic block diagram of another embodiment of a test system in accordance with the present invention.

FIG. 17 is a schematic block diagram of another embodiment of a test system 10 that includes a test container array 12 and a testing base 144. The test container array 12 includes a plurality of test containers 14 and the testing base 144 includes a plurality of testing base containers 148. The test container array 12 is constructed to fit into the testing base 144. As such, the testing base containers 148 are slightly larger than the test containers 14 but are of a similar shape.

Both the test container array 12 and the testing base 144 may include more or less test containers 14 and testing base containers 148 than shown. The test containers 14 and testing base containers 148 may be a variety of shapes, depths, and sizes (e.g., cylindrical, rectangular prism, circular, test tube, petri dish, etc.). Each test container 14 includes a set of test container electrodes 16 and each testing base container 148 includes a set of testing base electrodes 146. The set of test container electrodes 16 includes one or more test container electrodes. The set of testing base electrodes 146 includes one or more testing base electrodes 146.

The test container electrodes 16 and the testing base electrodes 146 are electric conductors used to carry current into, alter, or measure conductivity of non-metallic solids, liquids, gases, plasmas, or vacuums. The test container electrodes 16 and the testing base electrodes 146 are constructed of electrically conductive material. For example, the test container electrodes 16 and the testing base electrodes 146 may be a transparent conductive material, such that optical observations of the testing container 14 are unobstructed. As a specific example, an electrode is constructed from one or more of: Indium Tin Oxide, Graphene, Carbon Nanotubes, Thin Metal Films, Silver Nanowires Hybrid Materials, Aluminum-doped Zinc Oxide (AZO), Amorphous Indium-Zinc Oxide, Gallium-doped Zinc Oxide (GZO), and poly polystyrene sulfonate (PEDOT).

The test container electrodes 16 and the testing base electrodes 146 may be a variety of shapes (e.g., coil, cylindrical, conical, flat, square, circular, domed, spherical, spear shaped, etc.) and may be placed in a variety of positions within the test container 14 and the testing base 144 such that the test container electrodes 16 and the testing base electrodes 146 align for electric coupling. Here, four test container electrodes 16 are shown near the bottom corners of the test container 14 and four test container electrodes 16 are below a solution 20 fill line of the test container 14. Likewise, four testing base electrodes 146 are shown near the bottom corners of the testing base 148 and four testing base electrodes 146 are in a position corresponding to the solution 20 fill line of the test container 14.

The test system 10 is operable to detect and interpret electrical characteristics of a mass such as an inorganic material or an organic material. For example, an organic material includes one or more of: one or more cells (e.g., an individual cell, multiple cells, tissue, etc.) and one or more portions of a cell (e.g., a section of cell membrane). A cell may be an animal, human, plant, and/or other biological cell and is any type of cell (e.g., heart, brain, neuron, muscle, skin, lung, etc.).

A mass 18 is shown in a solution 20 in the testing container 14. The solution 20 maintains the integrity and viability of the mass 18 and negligibly interferes with testing substances or biochemical reactions. For example, the solution 20 is a saline solution, a preservative, a cell culture solution, etc. The test system 10 is operable to detect and interpret the electrical characteristics of the testing container 14 with the solution 20, the electrical characteristics of the mass 18 in the solution 20, and the electrical characteristics of the mass 18 in the solution 20 when a testing substance is added.

Based on the differences between the detected electrical characteristics (e.g., with and without the testing substance), the test system 10 can determine the effect of a testing substance on a mass. The electrical characteristics of the mass 18 include one or more of cell impedance, membrane potential, size, shape, density, movement, orientation, cell excitation (e.g., beat amplitude), etc. For example, in a non-viable cell, the cell membrane of a cell is unable to maintain its potential resulting in a decreased capacitance (e.g., as a cell dies, its impedance drops). As another example, the shape of a cell responds very sensitively to chemical, biological, or physical stimuli. Therefore, a cell that has reduced or increased in shape as a result of exposure to a testing substance indicates a biological effect (e.g., cell destruction, etc.).

In an example of operation, the test container array 12 is placed in the testing base 144 such that the plurality of test container electrodes 16 electrically couple with the plurality of testing base electrodes 146. The coupling between the test container electrodes 16 and the plurality of testing base electrodes 146 may be direct, capacitive, or inductive (e.g., when the electrodes are coils). When the contents of the testing container 14 affect the electrical characteristics of the test container electrodes 16, the electrical characteristics of the plurality of testing base electrodes 146 are also affected due to the electric coupling between the test container electrodes 16 and the plurality of testing base electrodes 146.

Figure 18:
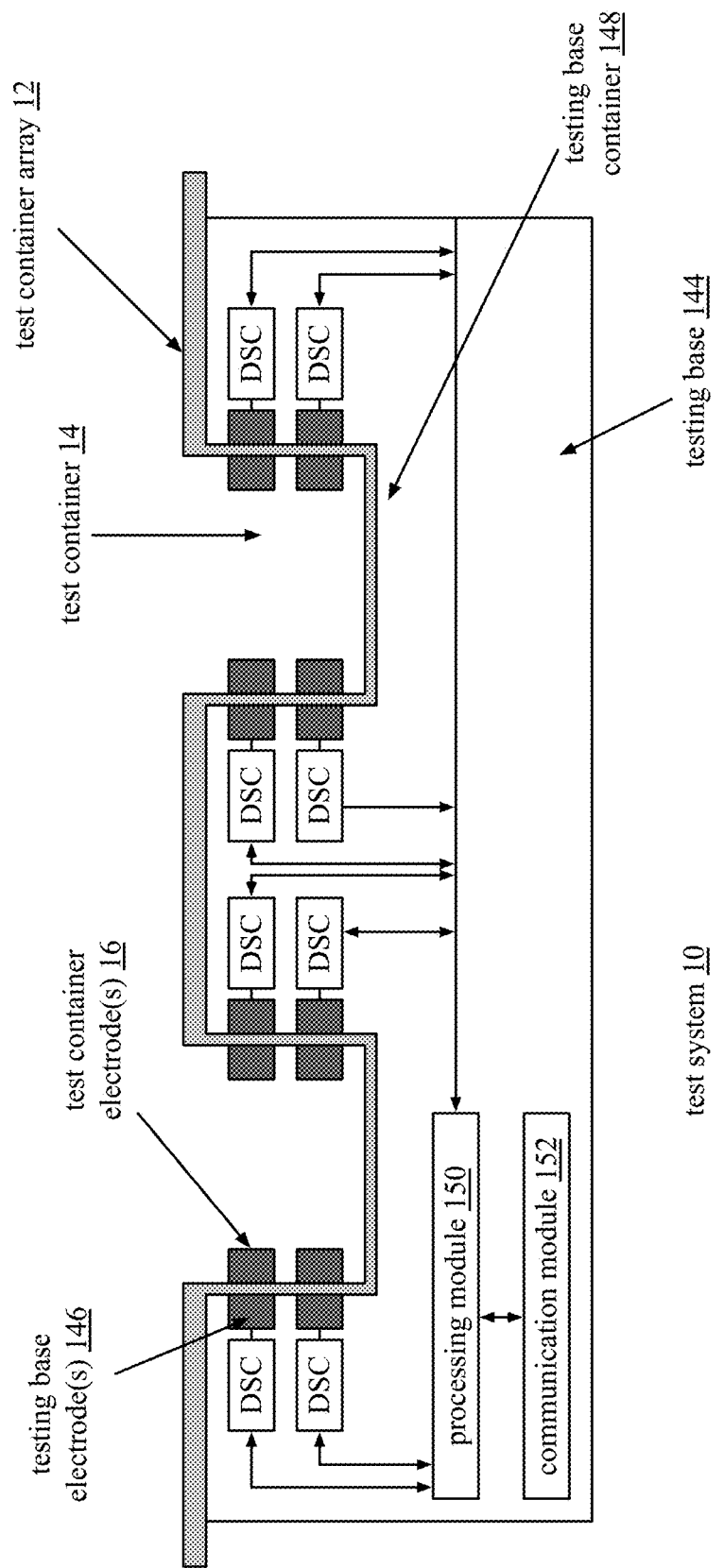
FIG. 18 is a cross section schematic block diagram of another embodiment of a test system in accordance with the present invention.

FIG. 18 is a cross schematic block diagram of another embodiment of a test system 10 that includes a cross sectional view of a test container array 12 resting in a testing base 144. The test container array 12 includes a plurality of test containers 14 and the testing base 144 includes a plurality of testing base containers 148. Each test container 14 includes a set of test container electrodes 16 and each testing base container 148 includes a set of testing base electrodes 146. The test container array 12 is placed in the testing base 144 such that the plurality of test container electrodes 16 electrically couple with the plurality of testing base electrodes 146. The coupling between the test container electrodes 16 and the plurality of testing base electrodes 146 may be direct, capacitive, or inductive (e.g., when the electrodes are coils).

The testing base 144 further includes a plurality of drive-sense circuits (DSCs), a processing module 150, and a communication module 152. The communication module 152 is constructed in accordance with one or more wired communication protocol and/or one or more wireless communication protocols that is/are in accordance with the one or more of the Open System Interconnection (OSI) model, the Transmission Control Protocol/Internet Protocol (TCP/IP) model, and other communication protocol module.

Each testing base electrode 146 is coupled to a drive-sense circuit (DSC). The DSCs provide electrode signals to the test container electrodes 16 and detect changes in electrical characteristics of the test container electrodes. The DSCs function as described in co-pending patent application entitled, "DRIVE SENSE CIRCUIT WITH DRIVE-SENSE LINE", having a Ser. No. 16/113,379, and a filing date of Aug. 27, 2018 and in accordance with the discussion of previous Figures.

When the contents of the testing container 14 affect the electrical characteristics of the test container electrodes 16, the electrical characteristics of the plurality of testing base electrodes 146 are also affected due to the electric coupling between the test container electrodes 16 and the plurality of testing base electrodes 146. The DSCs provide the detected changes in electrical characteristics of the testing base electrodes 146 to the processing module 150. The processing module 150 is described in greater detail at the end of the detailed description of the invention section and operates similarly to the test container array processing module and the test container processing module of previous Figures. The processing module 150 processes the detected changes in electrical characteristics of the testing base electrodes 146 from the DSCs to determine the electrical characteristics of biological material present in the testing containers 14. The processing the detected changes in electrical characteristics of the testing base electrodes 146 from the DSCs to determine the electrical characteristics of biological material occurs similarly to the methods described with reference to FIGS. 7-16.

The processing module 150 communicates the electrical characteristics of the biological material to the communication module 152. Communicating the electrical characteristics of biological material to the communication module 152 may include formatting the data in a particular format with respect to the communication protocol of the communication module. The communication module 152 is operable to communicate the electrical characteristics of cells via one or more communication protocols.

Figure 19:
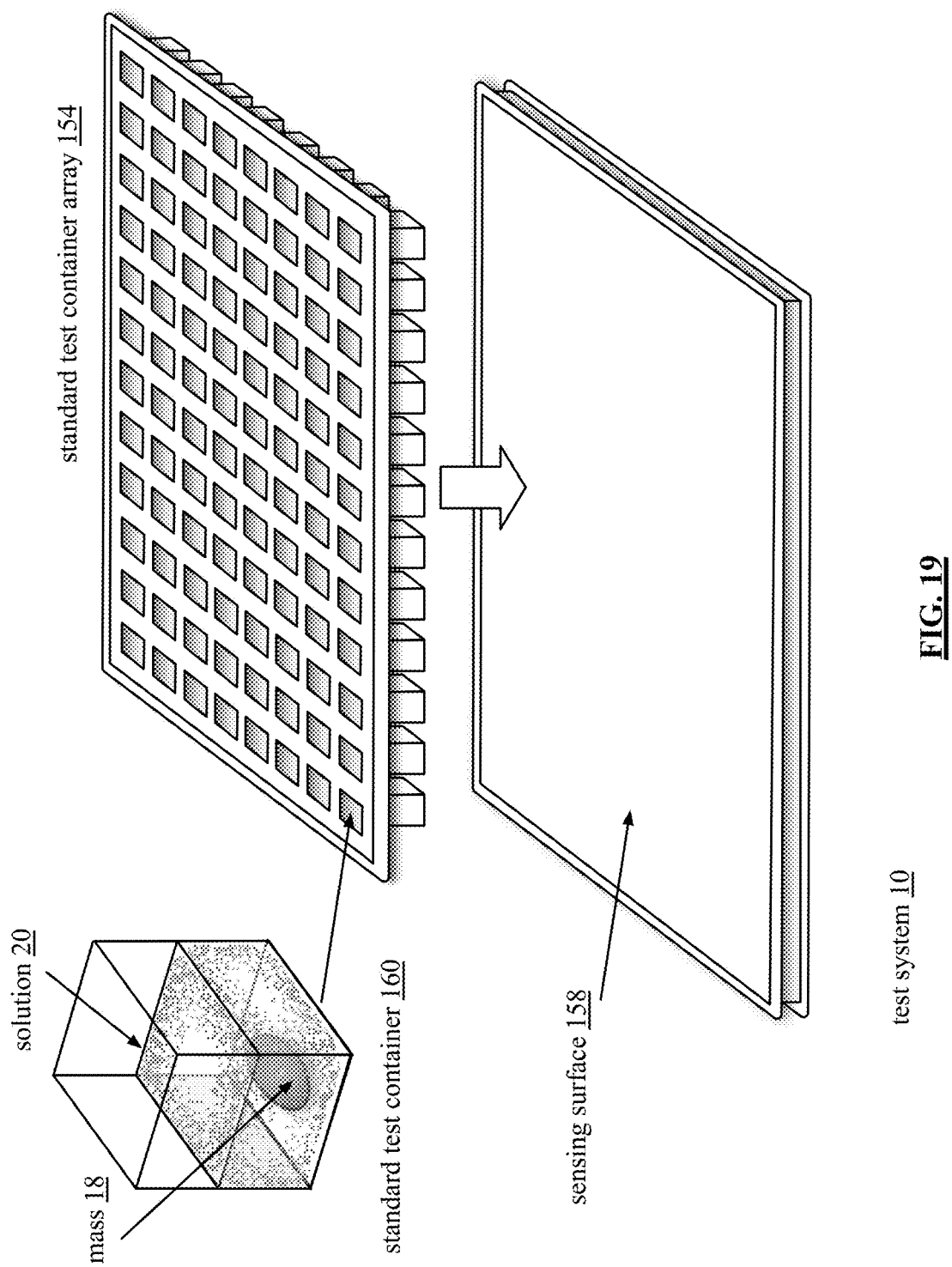
FIG. 19 is a schematic block diagram of another embodiment of a test system in accordance with the present invention.

FIG. 19 is a schematic block diagram of another embodiment of a test system 10 that includes a sensing surface 158 and a standard test container array 154. The standard test container array 154 includes a plurality of standard test containers 160. The plurality of standard test containers 160 do not include electrodes as compared to the test container array of previous Figures. The standard test container array 154 may be comprised of a variety of materials such as polystyrene, polypropylene, glass, flexible plastic tape, and quartz, and may be a variety of shapes and sizes. The standard test container array 154 is shown as a rectangular array of 8×12 cubical standard test containers 160. The standard test container array may include more or less standard test containers 160 than shown and the standard test containers 160 may be a variety of shapes, depths, and sizes (e.g., cylindrical, rectangular prism, circular, test tube, petri dish, etc.).

The sensing surface 158 includes a plurality of sensors (e.g., electrodes, capacitor sensing cells, capacitor sensors, inductive sensor, etc.) to detect electrical characteristics of a mass 18 (e.g., a biological material such as one or more cells) present in the standard test container array 154 when the standard test container array 154 is placed in close proximity (e.g., is in physical contact) to the sensing surface 158.

FIG. 20 is a schematic block diagram of an embodiment of a sensing surface 158 that includes a plurality of drive-sense circuits (DSCs), a sensing surface processing module 164, and a communication module 166. The sensing surface processing module 164 (i.e., a processing module) is described in greater detail at the end of the detailed description of the invention section and operates similarly to the test container array and test container processing modules of previous Figures.

The communication module 166 is constructed in accordance with one or more wired communication protocol and/or one or more wireless communication protocols that is/are in accordance with the one or more of the Open System Interconnection (OSI) model, the Transmission Control Protocol/Internet Protocol (TCP/IP) model, and other communication protocol module. The communication module 166 may include a wireless communication unit or a wired communication unit. A wireless communication unit includes a wireless local area network (WLAN) communication device, a cellular communication device, a Bluetooth device, and/or a ZigBee communication device. A wired communication unit includes a Gigabit LAN connection, a Firewire connection, and/or a proprietary computer wired connection.

The sensing surface 158 includes integrated electrodes 162 that are distributed throughout the sensing surface 158 or where sensing functionality is desired. For example, a first group of the electrodes are arranged in rows and a second group of electrodes are arranged in columns. As will be discussed in greater detail with reference to one or more of FIGS. 21A-28, the row electrodes are separated from the column electrodes by a dielectric material.

The sensing surface 158 may include one or more layers (e.g., dielectric layers) and the electrodes 162 are comprised of a conductive material such as one or more of: Indium Tin Oxide, Graphene, Carbon Nanotubes, Thin Metal Films, Silver Nanowires Hybrid Materials, Aluminum-doped Zinc Oxide (AZO), Amorphous Indium-Zinc Oxide, Gallium-doped Zinc Oxide (GZO), and poly polystyrene sulfonate (PEDOT). The electrodes 162 are in-cell or on-cell with respect to layers of the sensing surface 158. For example, a conductive trace is placed in-cell or on-cell of a layer of the sensing surface 158.

Each drive-sense circuit (DSC) is coupled to a row or a column electrode 162 of the sensing surface and detects changes to the electrical characteristics of the electrodes.

The sensing surface processing module 164 is coupled to the plurality of DSCs and interprets the detected changes in electrical characteristics of the electrodes as changes in the impedance of the electrode. The impedance of an electrode depends on a self-capacitance (e.g., the capacitance of the electrode with respect to a reference (e.g., ground, etc.) and a mutual capacitance (e.g., the capacitance between a row electrode and a column electrode).

In an example of operation, a standard test container array (e.g., a test container array with no integrated electrodes) is placed onto or within close proximity to the sensing surface 158. The standard test container array and its contents have an effect on the mutual capacitance of the electrodes 162 and a negligible effect on the self-capacitance of the electrodes 162. A standard test container array (filled with a solution) has a first effect on the mutual capacitance of the electrodes 162 due to the properties of the standard test container array and/or the solution. When biological material (e.g., one or more biological cells, biological tissue, a portion of a cell, etc.), solutions, testing substances, etc., are added to the standard test container array, the mutual capacitance of the electrodes are affected.

The plurality of DSCs detect changes in electrical characteristics of the electrodes 162 (e.g., due to mutual capacitance change). When detected, the plurality of DSCs send a set of changes in electrical characteristics of a set of electrodes 162 to the sensing surface processing module 164. The sensing surface processing module 164 receives the set of changes in electrical characteristics of the set of electrodes 162 and interprets the set of changes in electrical characteristics as a mutual capacitance value representative of electrical characteristics of biological material. The sensing surface processing module 164 interprets the set of changes in electrical characteristics as a mutual capacitance value representative of electrical characteristics of biological material using similar methods as described in FIGS. 7-15.

The sensing surface processing module 164 communicates the electrical characteristics of the biological material to the communication module 166. Communicating the electrical characteristics of biological material to the communication module 32 may include formatting the data in a particular format with respect to the communication protocol of the communication module. The communication module 166 is operable to communicate the electrical characteristics of biological material via one or more communication protocols.

Figure 21A:
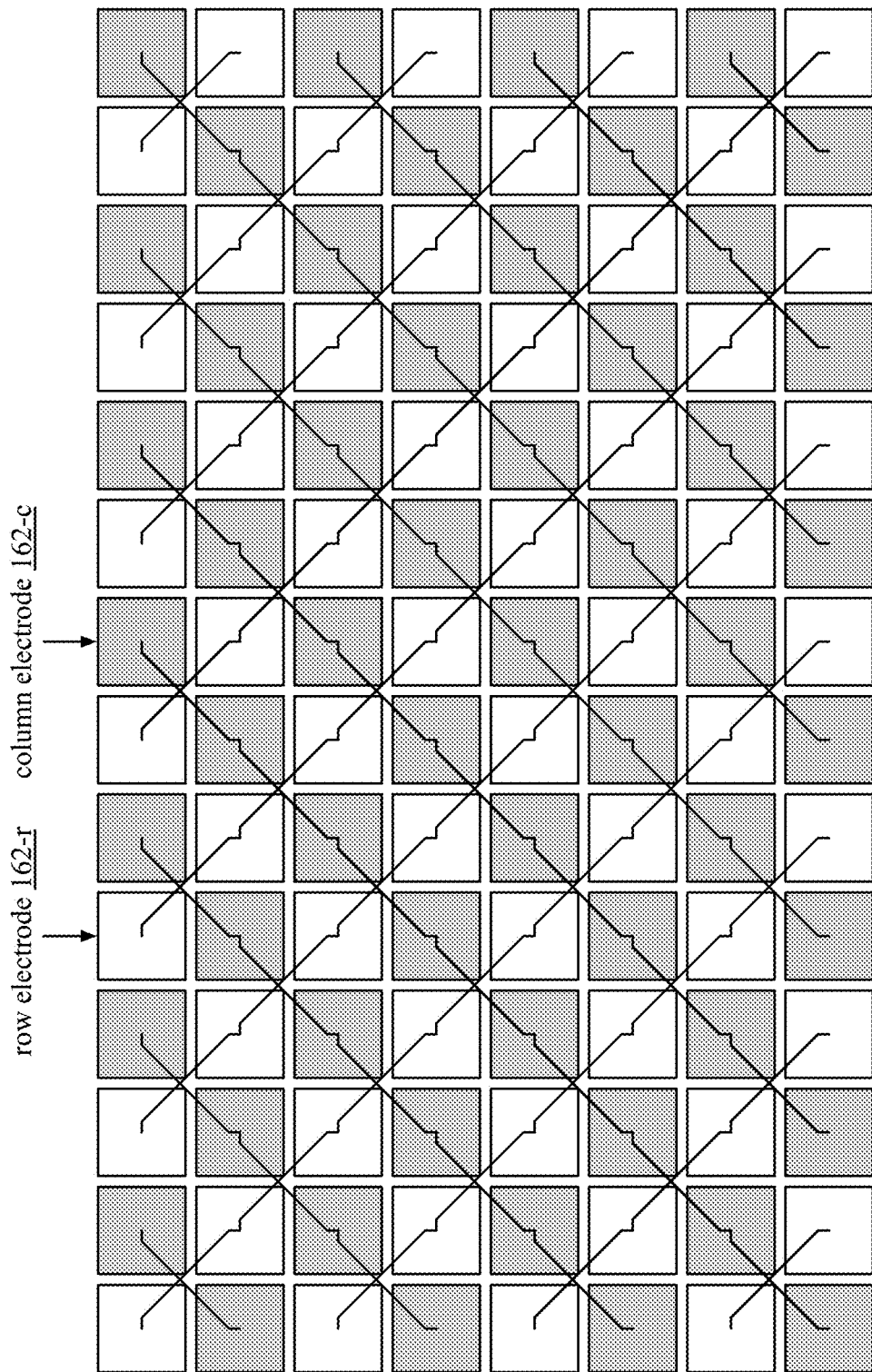
FIGS. 21A-21B are schematic block diagrams of embodiments of a sensing surface electrode pattern in accordance with the present invention.
Figure 21B:
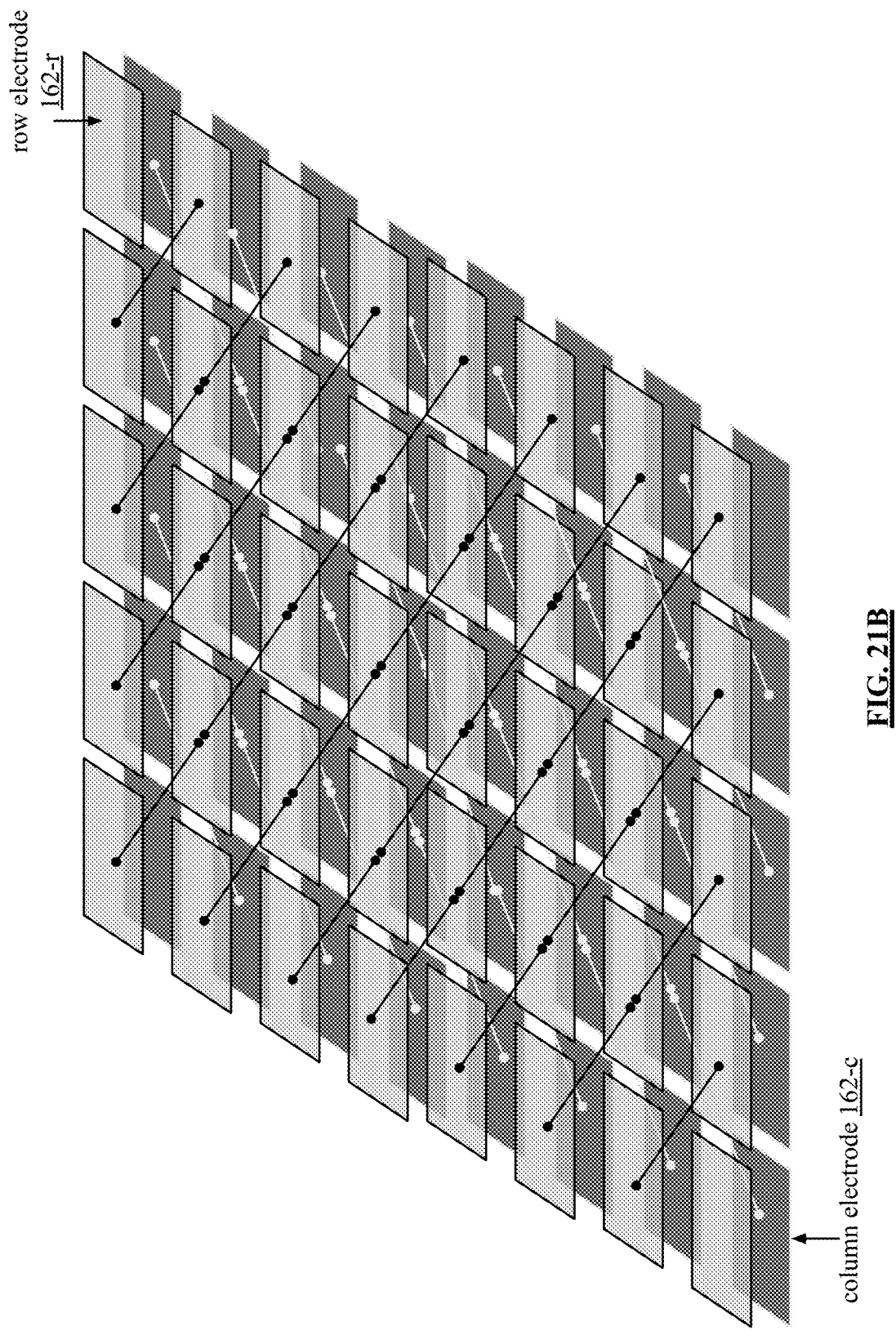

FIGS. 21A-21B are schematic block diagrams of embodiments of a sensing surface electrode pattern that includes rows of electrodes 162-$r$ and columns of electrodes 162-$c$. Each row of electrodes 162-$r$ and each column of electrodes 162-$c$ includes a plurality of individual conductive cells (e.g., capacitive sense plates) (e.g., light gray squares for rows, dark gray squares for columns) that are electrically coupled together. The size of a conductive cell depends on the desired resolution of sensing.

For example, a conductive cell size may be 1 millimeter by 1 millimeter or less to 5 millimeters by 5 millimeters or more and based on the size of a standard test container, the size and type of biological materials to be sensed, and the type of information to be sensed. For example, a larger conductive cell size may be appropriate when measuring the electrical network properties of brain tissue or heart tissue. However, the testing of single biological cells requires higher resolution. Making the conductive cells smaller improves sensing resolution and will typically reduce sensor errors (e.g., prevention of sensing electrical characteristics from more than one testing container). While the cells are shown to be square, they may be of any polygonal shape, diamond, or circular shape.

The cells for the rows and columns may be on the same layer or on different layers. In FIG. 21A, the cells for the rows and columns are shown on the same layer. In FIG. 21B, the cells for the rows and columns are shown on different layers. The electric coupling between the cells is done using vias and running traces (e.g., wire traces) on another layer. Note that the cells are on one or more layers (e.g., ITO layers) of the sensing surface.

Figure 22A:
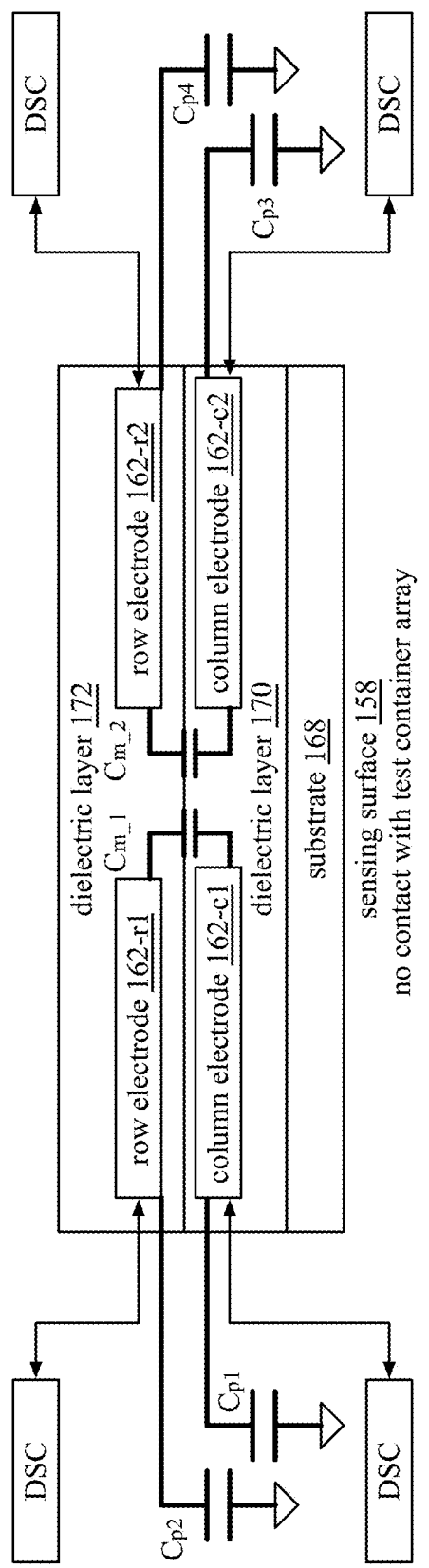
FIGS. 22A-22B are cross section schematic block diagrams of examples of capacitance of a sensing surface in accordance with the present invention.
Figure 22B:
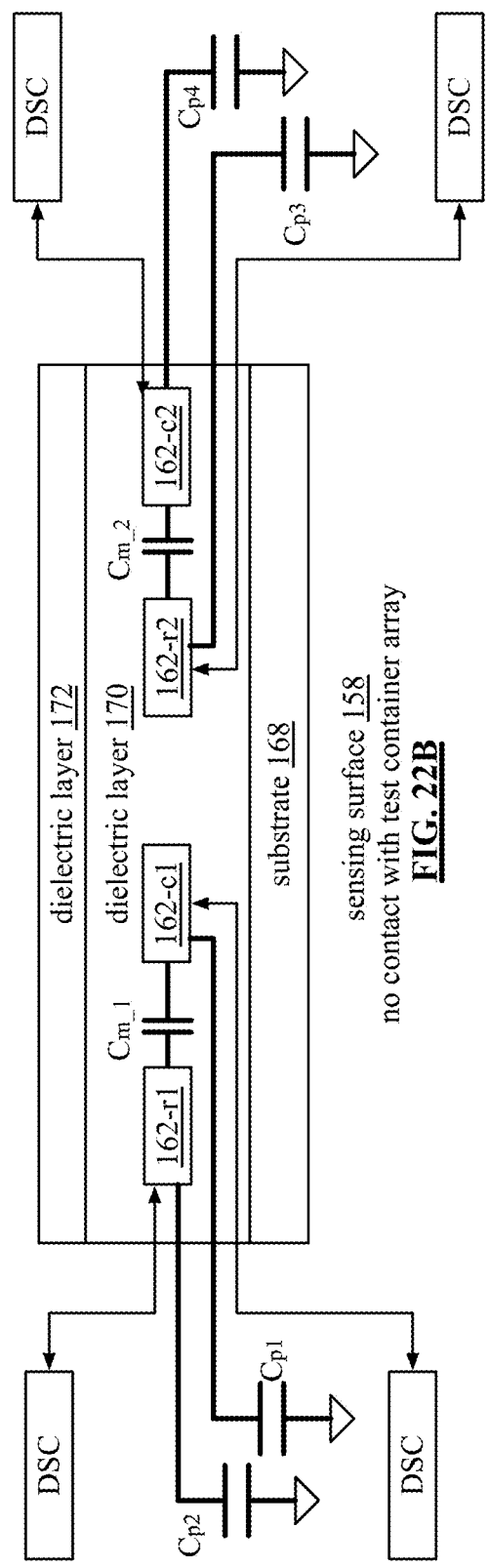

FIGS. 22A-22B are cross section schematic block diagrams of examples of capacitance of a sensing surface 158 with no contact with a test container array. The sensing surface 158 includes electrodes 162s positioned proximal to a dielectric layer 170, which may be between a top dielectric layer 172 and a substrate 168.

In FIG. 22A, the row electrodes 162-r1 and 162-r2 are on the top dielectric layer 172 above the column electrodes 162-c1 and 162-c2 which are on the dielectric layer 170. In FIG. 22B, the row electrodes 162-r and the column electrodes 162-c are on the same layer (e.g., dielectric layer 170). Each electrode 162 has a self-capacitance, which corresponds to a parasitic capacitance created by the electrode with respect to other conductors in the sensing surface 158 (e.g., ground, conductive layer(s), and/or one or more other electrodes).

For example, row electrode 162-r1 has a parasitic capacitance $C_{p2}$, column electrode 162-c1 has a parasitic capacitance $C_{p1}$, row electrode 162-r2 has a parasitic capacitance $C_{p4}$, and column electrode 162-c2 has a parasitic capacitance $C_{p3}$. Note that each electrode includes a resistance component and, as such, produces a distributed R-C circuit. The longer the electrode, the greater the impedance of the distributed R-C circuit. For simplicity of illustration the distributed R-C circuit of an electrode will be represented as a single parasitic self-capacitance.

As shown, the sensing surface 158 includes a plurality of layers 168-172. Each illustrated layer may itself include one or more layers. For example, the dielectric layer 172 may include a surface protective film, a glass protective film, and/or one or more pressure sensitive adhesive (PSA) or temperature sensitive layers. As another example, the second dielectric layer 170 may include a glass cover, a polyester (PET) film, a support plate (glass or plastic) to support, or embed, one or more of the electrodes 162-c1, 162-c2, 162-r1, and 162-r2 (e.g., where the column and row electrodes are on different layers), a base plate (glass, plastic, or PET), an ITO layer, and one or more PSA layers. As yet another example, the substrate 168 includes one or more of a base plate (glass, plastic, or PET), an ITO layer, and one or more PSA layers.

A mutual capacitance (Cm_1 and Cm_2) exists between a row electrode and a column electrode. When no test container array is present, the self-capacitances and mutual capacitances of the sensing surface 158 are at a nominal state. Depending on the length, width, and thickness of the electrodes, separation from the electrodes and other conductive surfaces, and dielectric properties of the layers, the self-capacitances and mutual capacitances can range from a few pico-Farads to 10's of nano-Farads.

The sensing surface 158 includes a plurality of drive sense circuits (DSCs). The DSCs are coupled to the electrodes of the sensing surface 158 and detect changes in electrical characteristics of affected electrodes. The DSCs function as described in co-pending patent application entitled, "DRIVE SENSE CIRCUIT WITH DRIVE-SENSE LINE", having a serial number of Ser. No. 16/113,379, and a filing date of Aug. 27, 2018 and as described in previous Figures.

Figure 23:
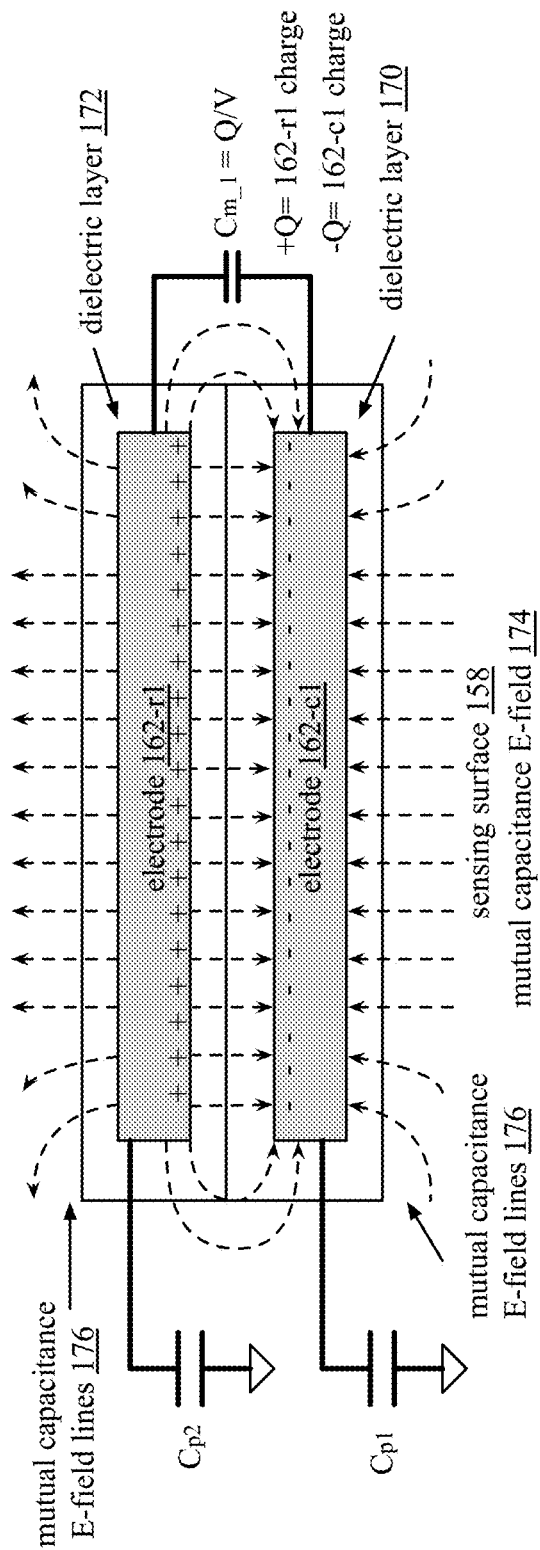
FIG. 23 is a cross section schematic block diagram of an example of a mutual capacitance electric field in accordance with the present invention.

FIG. 23 is a cross section schematic block diagram of an example of a mutual capacitance electric field (E-field) 174 of electrodes 162 of a sensing surface 158. A row electrode 162-r1 and a column electrode 162-c1 of the sensing surface 158 are shown on separate dielectric layers 172-170 respectively. The row electrode 162-r1 has a self-capacitance $C_{p2}$ (e.g., the capacitance of the row electrode 162-r1 with respect to a reference (e.g., ground, etc.)) and the column electrode 162-c1 has a self-capacitance $C_{p1}$ (e.g., the capacitance of the column electrode 162-c1 with respect to a reference (e.g., ground, etc.)).

The mutual capacitance $C_{m\_1}$ is the capacitance between the row electrode 162-r1 and the column electrode 162-c1. When a charge of +Q is delivered to the row electrode 162-r1, a charge of −Q will be induced on the column electrode 162-c1 in order to keep the system neutral. The mutual capacitance $C_{m\_1}$ can be represented by the equation $C_{m\_1}=Q/V$ where V is the voltage difference between the row electrode 162-r1 and the column electrode 162-c1, and Q is the charge distribution between the row electrode 162-r1 and the column electrode 162-c1. As such, a mutual capacitance electric field (E-field) 174 exists between the row electrode 162-r1 and the column electrode 162-c1 as shown by the mutual capacitance E-field lines 176. When the row electrode 162-r1 has a charge of +Q, the mutual capacitance E-field lines 176 are shown with an arrow directed toward the negative charge −Q of the column electrode 162-c1.

Figure 24:
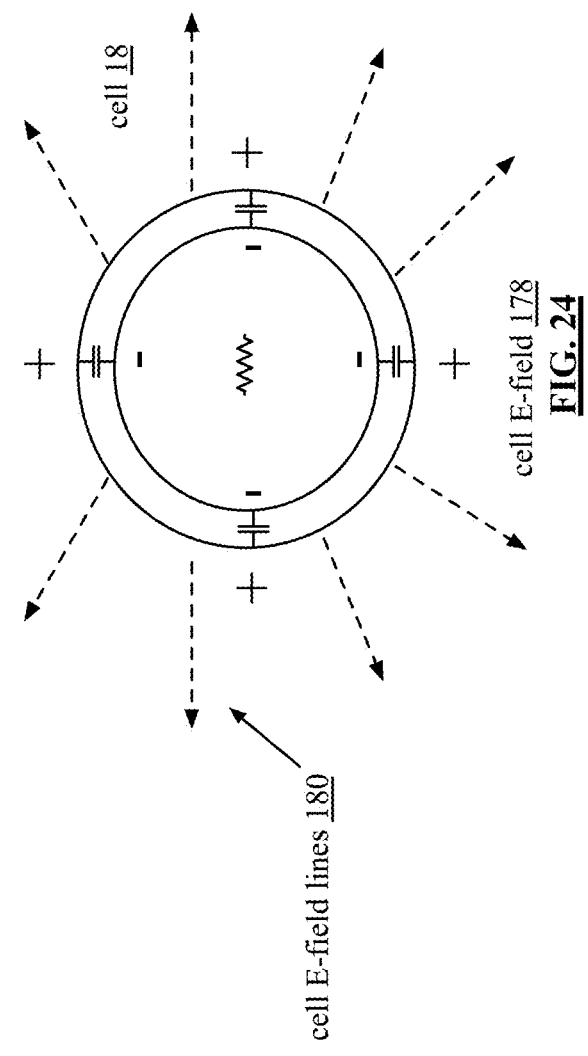
FIG. 24 is an example of a cell electric field in accordance with the present invention.

FIG. 24 is an example of a cell electric field (E-field) 178. As discussed previously, the inside of a cell 18 is more negatively charged than the outside due to the concentration difference of ions inside and outside of the cell 18. As such, the cell 18 has a cell membrane potential or cell membrane voltage, which is the difference in electric potential between the interior and exterior of the cell 18. Typical values of membrane potential from the exterior of the cell are measured in ranges from −35 mV to −90 mV.

The different concentrations of internal and external ions of the cell 18 result in a positive charge buildup on the outside of the membrane and a negative charge buildup on the inside of the cell membrane (e.g., the cell membrane capacitance). Thus, a cell E-field 178 exists shown by the cell E-field lines 180 with arrows directed outward from the positively charged exterior of the cell 18.

Figure 25:
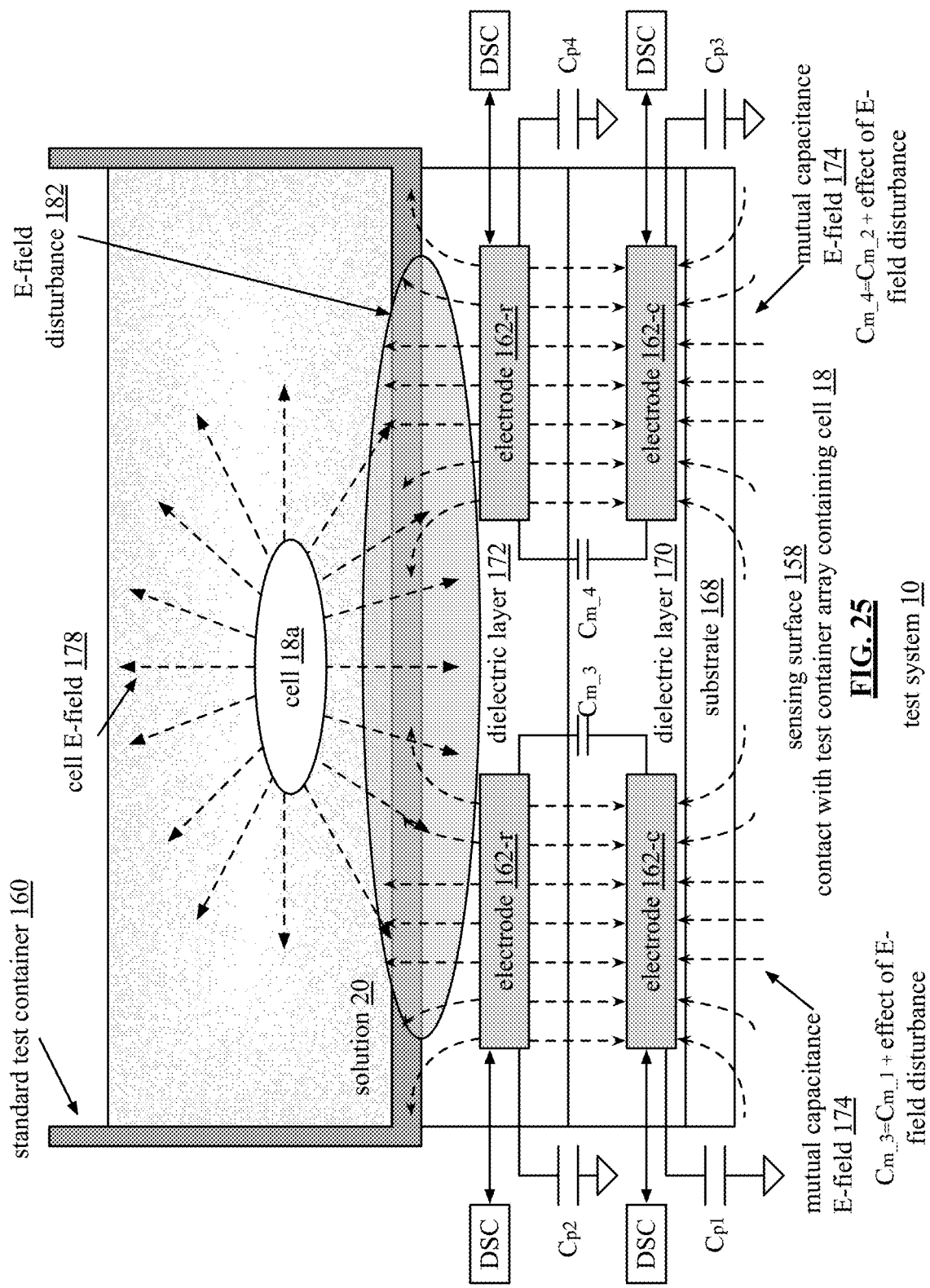
FIG. 25 is a cross section schematic block diagram of an embodiment of a test system in accordance with the present invention.

FIG. 25 is a cross section schematic block diagram of an embodiment of a test system 10 that includes a sensing surface 158 in contact with a standard test container 160 of a standard test container array 154. The sensing surface 158 includes the substrate 168, rows of electrodes 162-r on dielectric layer 172, columns of electrodes 162-c on dielectric layer 170, and a plurality of drive-sense circuits (DSCs).

Each electrode 162 has a self-capacitance, which corresponds to a parasitic capacitance created by the electrode with respect to other conductors in the sensing surface 158 (e.g., ground, conductive layer(s), and/or one or more other electrodes). For example, row electrode 162-r1 has a parasitic capacitance $C_{p2}$, column electrode 162-c1 has a parasitic capacitance $C_{p1}$, row electrode 162-r2 has a parasitic capacitance $C_{p4}$, and column electrode 162-c2 has a parasitic capacitance $C_{p3}$. As previously discussed, mutual capacitance electric fields (E-fields) 174 exist between the row electrodes 162-r and the column electrodes 162-c.

A cross section of the standard test container 160 of the standard test container array is shown containing one or more cells ("cell") 18a and a solution 20 (e.g., a saline solution, preservative, etc.). The cell 18*a* has a cell membrane potential (e.g., voltage) as previously discussed and thus has a cell E-field 178. When the test container array containing the cell 18*a* is placed on the sensing surface 158, the cell E-field 178 interferes with the mutual capacitance E-field 174 in a subtractive or additive manner. This interference or E-field disturbance 182 affects the mutual capacitance of the electrodes 162. For example, a reduction in the mutual capacitance E-field 174 results in a higher mutual capacitance and an increase in the mutual capacitance E-field 174 results in a lower mutual capacitance.

A mutual capacitance Cm_3 exists between the row electrode 162-*r*1 and the column electrode 162-*c*1 where Cm_3 is equal to Cm_1 (of FIG. 22A, i.e., the mutual capacitance prior to the E-field disturbance) plus the effect of the E-field disturbance 182. A mutual capacitance Cm_4 exists between the row electrode 162-*r*2 and the column electrode 162-*c*2 where Cm_4 is equal to Cm_2 (of FIG. 22A, i.e., the mutual capacitance prior to the E-field disturbance) plus the effect of the E-field disturbance 182. Here, the cell E-field 178 lines and the mutual capacitance E-field 174 lines are in opposite directions such that the E-field disturbance 182 is likely subtractive. With a subtractive E-field disturbance 182, Cm_3 and Cm_4 are greater than the values of Cm_1 and Cm_2 of FIG. 22A. The self-capacitance values are unaffected.

The DSCs are coupled to the electrodes of the sensing surface 158 and detect changes in the electrical characteristics of the electrodes. For example, the DSCs detect a change in the mutual capacitance of the electrodes due to the E-field disturbance 182 created by the presence of the cell 18*a* in the solution 20. The DSCs are coupled to a sensing surface processing module 164 that interprets the detected changes in electrical characteristics of the electrodes 162 as a change in the impedance of the electrode and interpret the change in impedance as electrical characteristics of biological material (e.g., the cell 18*a*). The electrical characteristics of biological material may include position, impedance, shape, movement, density, excitability, and potential.

For example, a first mutual capacitance measurement corresponds to biological material in a solution 20 (e.g., the e-field of the biological material disturbs the mutual capacitance e-field of the electrode changing the mutual capacitance of the electrodes affected by the biological material). The first mutual capacitance measurement may correspond to the strength of the biological material's electric field and thus indicate biological material characteristics such as cell membrane capacitance, cell membrane potential, etc. Depending on which electrodes are experiencing a change and at what level, a position, orientation, shape etc., of the biological material can be determined.

When a testing substance is added to the standard test container 160, a second mutual capacitance measurement may correspond to the strength of the biological material's electric field as affected by the testing substance. Comparing the first and second mutual capacitance measurements indicates biological material characteristics such as cell membrane capacitance, cell membrane potential, etc., when the cell is exposed to the testing substance. Depending on which electrodes are experiencing a change and at what level, a change in the position, orientation, shape etc., of the biological material can be determined.

Figure 26:
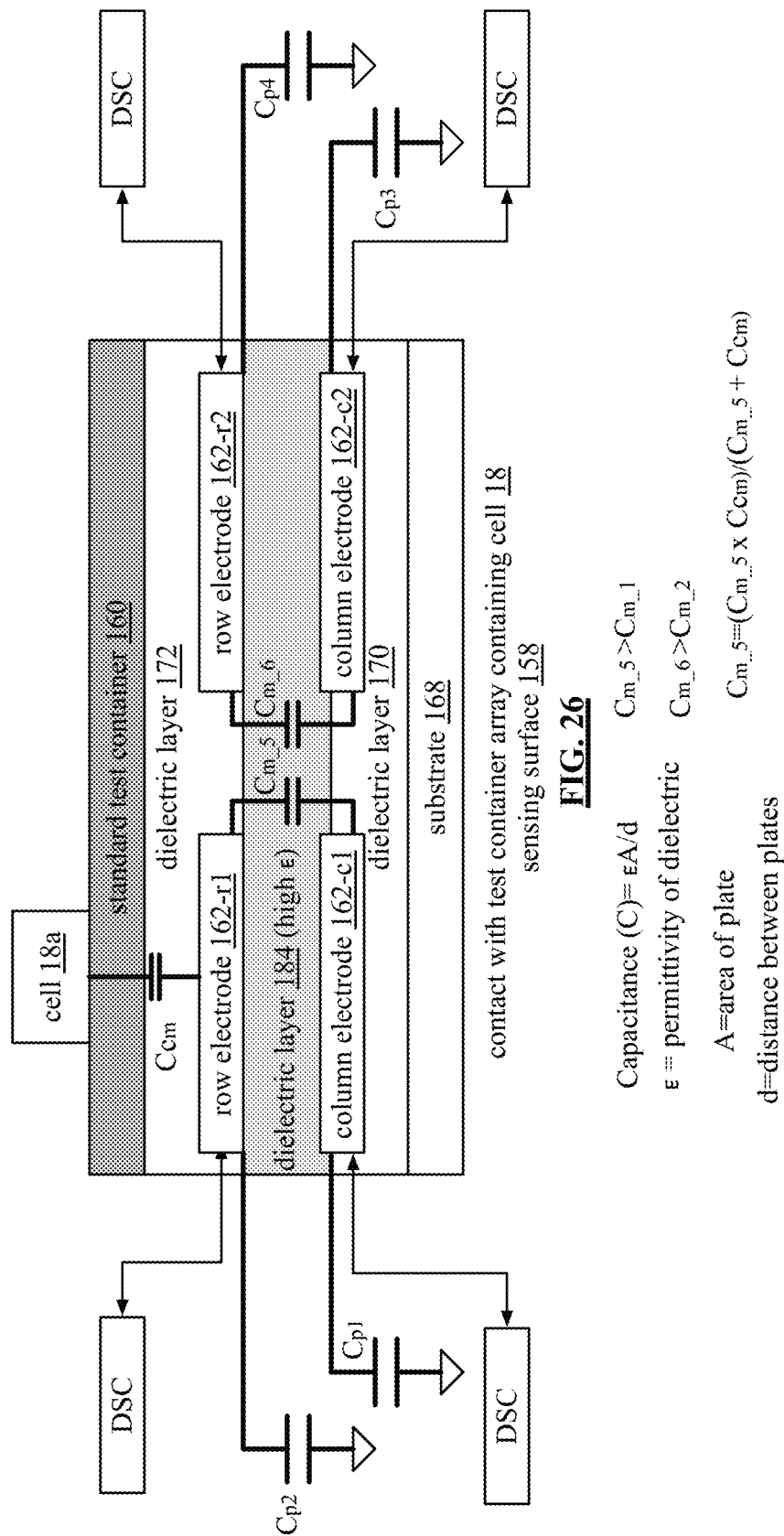
FIG. 26 is a cross section schematic block diagram of an example of capacitance of a sensing surface in accordance with the present invention.

FIG. 26 is a cross section schematic block diagram of an example of capacitance of a sensing surface 158 in contact with a standard test container 160 containing one or more cells ("cell") 18*a*. The sensing surface 158 includes the row electrodes 162-*r*1 and 162-*r*2 positioned on a top dielectric layer 172 and the column electrodes 162-*c*1 and 162-*c*2 positioned on a dielectric layer 170. An additional dielectric layer 184 is between the row electrodes 162-*r*1 and 162-*r*2 and the column electrodes 162-*c*1 and 162-*c*2.

Each electrode 162 has a self-capacitance, which corresponds to a parasitic capacitance created by the electrode with respect to other conductors in the sensing surface 158 (e.g., ground, conductive layer(s), and/or one or more other electrodes). For example, row electrode 162-*r*1 has a parasitic capacitance $C_{p2}$, column electrode 162-*c*1 has a parasitic capacitance $C_{p1}$, row electrode 162-*r*2 has a parasitic capacitance $C_{p4}$, and column electrode 162-*c*2 has a parasitic capacitance $C_{p3}$.

A mutual capacitance (Cm_5 and Cm_6) exists between a row electrode and a column electrode. The dielectric layer 184 has a high dielectric constant in order to increase the mutual capacitance between the row electrode and column electrodes according to the equation $C = \varepsilon A/d$ where $\varepsilon$ is the dielectric constant, A is the area of an electrode, and d is the distance between the row and column electrodes. Cell membrane capacitances ($C_{CM}$) range from 0.9 $\mu F/cm^2$ to 2 $\mu F/cm^2$ (e.g., 90-200 $pF/\mu m^2$) and cell diameters range from 5-150 μm. The mutual capacitance between a row and column electrode is in the range of 1-2 pF. Capacitive coupling between a cell 18*a* (e.g., the cell membrane capacitance $C_{CM}$) and the row and column electrodes alters the mutual capacitance. For example, capacitance of two capacitors (e.g., C1 and C2) in series is calculated by the equation $C1 \times C2/(C1+C2)$. As such, when $C_{CM}$ is at 90 pF and mutual capacitance (e.g., $C_{m\_5}$) is at 2 pF, the mutual capacitance drops to 1.956 pF. While the DSCs are able to detect slight changes in the electrical characteristics of electrodes, increasing mutual capacitance through dielectrics enhances the detection of subtle mutual capacitance changes.

Here, the mutual capacitance $C_{m\_5}$ between the row electrode 162-*r*1 and the column electrode 162-*c*1 is greater than Cm_1 of FIG. 22A and mutual capacitance Cm_6 between the row electrode 162-*r*2 and the column electrode 162-*c*2 is greater than Cm_2 of FIG. 22A due to the high dielectric constant of dielectric layer 184 to enhance the capacitive coupling effect between the electrodes and the cell 18*a*.

Figure 27:
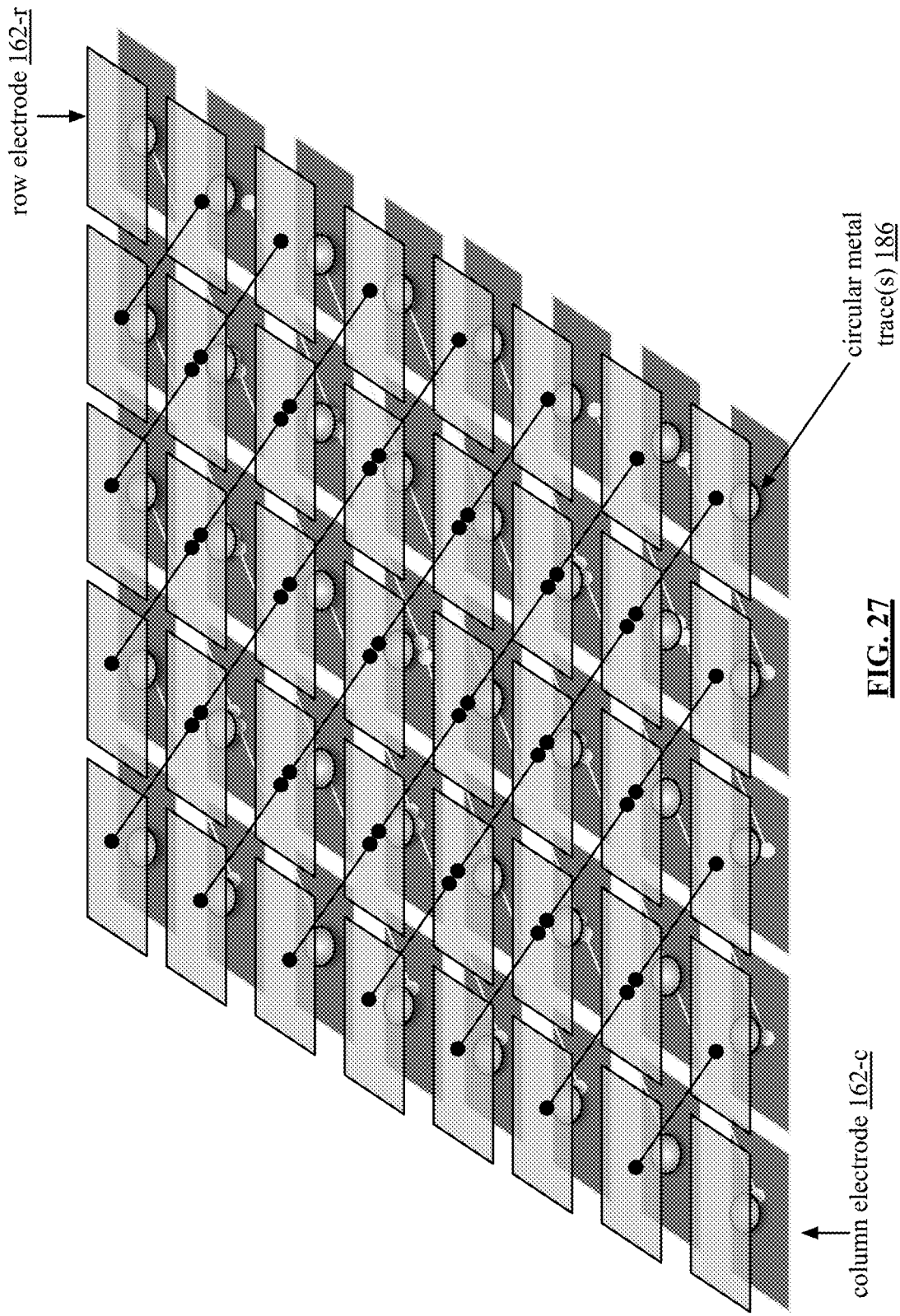
FIG. 27 is a schematic block diagram of an embodiment of a sensing surface electrode pattern in accordance with the present invention.

FIG. 27 is a schematic block diagram of an embodiment of a sensing surface electrode pattern that includes rows of electrodes 162-*r* and columns of electrodes 162-*c* on different layers of the sensing surface. Each row of electrodes 162-*r* and each column of electrodes 162-*c* includes a plurality of individual conductive cells (e.g., capacitive sense plates) (e.g., light gray squares for rows, dark gray squares for columns) that are electrically coupled together.

The pattern further includes circular metal traces 186 that are positioned in between the column and row layers and located where a row electrode overlaps a column electrode. The addition of the circular metal traces 186 increase the mutual capacitance between the row and column electrodes. While a circular metal trace 186 is shown, a variety of conductive traces and conductive trace sizes and shapes could be used.

Figure 28:
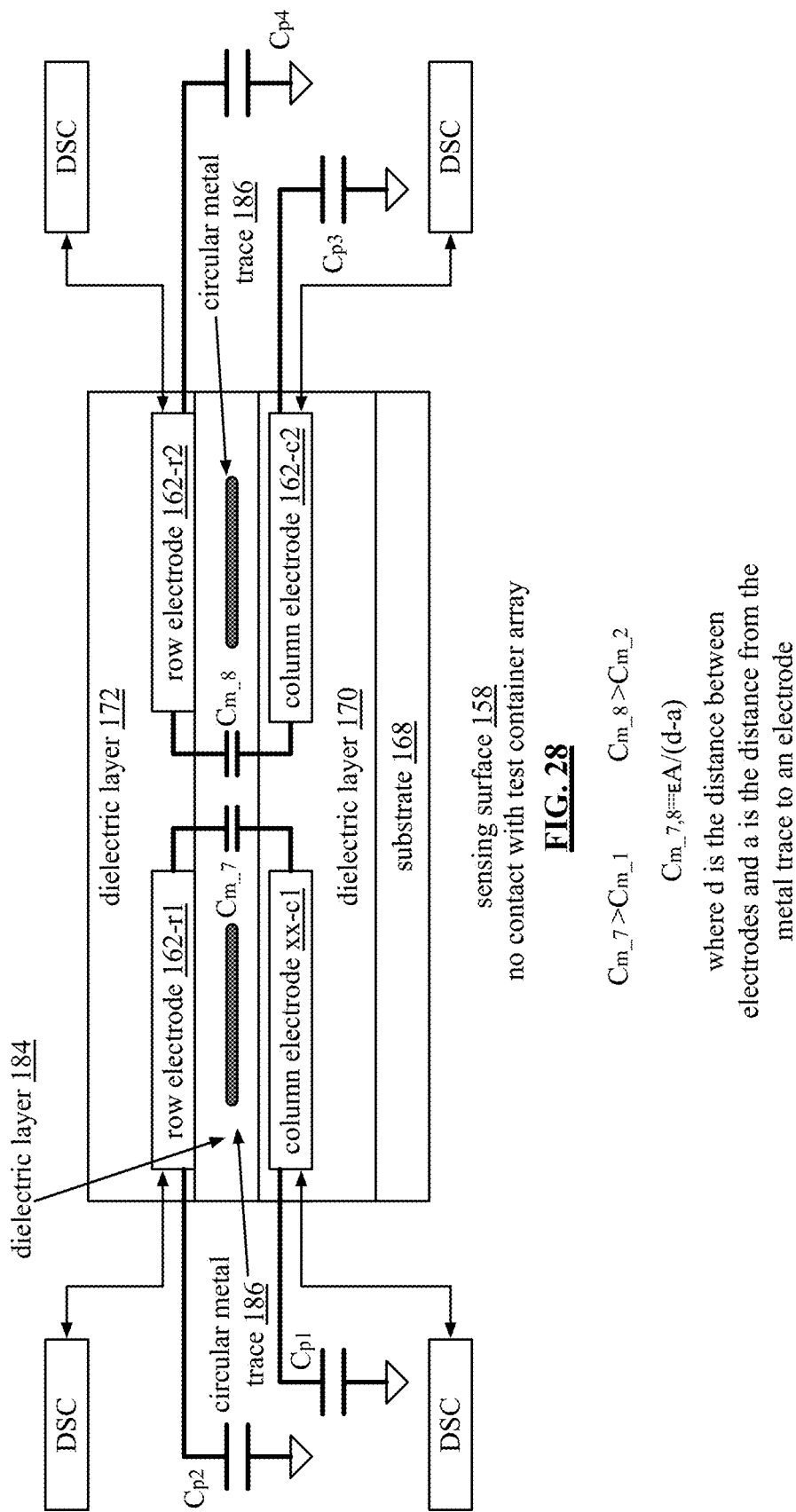
FIG. 28 is a cross section schematic block diagram of an examples of capacitance of a sensing surface in accordance with the present invention.

FIG. 28 is a cross section schematic block diagram of an examples of capacitance of a sensing surface 158 with no contact with the standard test container array. The sensing surface 158 includes the row electrodes 162-*r*1 and 162-*r*2 positioned on a top dielectric layer 172 and the column electrodes 162-*c*1 and 162-*c*2 positioned on a dielectric layer 170. An additional dielectric layer 184 is between the row electrodes 162-*r*1 and 162-*r*2 and the column electrodes 162-*c*1 and 162-*c*2 includes circular metal traces 186 positioned between the row and column electrodes.

Each electrode 162 has a self-capacitance, which corresponds to a parasitic capacitance created by the electrode with respect to other conductors in the sensing surface 158 (e.g., ground, conductive layer(s), and/or one or more other electrodes). For example, row electrode 162-*r*1 has a parasitic capacitance $C_{p2}$, column electrode 162-*c*1 has a parasitic capacitance $C_{p1}$, row electrode 162-*r*2 has a parasitic capacitance $C_{p4}$, and column electrode 162-*c*2 has a parasitic capacitance $C_{p3}$.

A mutual capacitance (Cm_7 and Cm_8) exists between a row electrode and a column electrode. The addition of the circular metal trace 186 between the row and column electrodes creates two capacitors in series between a row and column electrodes. The equivalent capacitance for these two in series capacitors is given by the equation Ceq=εA/(d−a) where d is the distance between a row and column electrode and a is the distance between an electrode and the circular metal trace 186. Therefore, adding the circular metal trace 186 increases the mutual capacitance between a row and column electrode since d is effectively reduced.

Here, the mutual capacitance Cm_7 between the row electrode 162-*r*1 and the column electrode 162-*c*1 is greater than Cm_1 of FIG. 22A and mutual capacitance Cm_8 between the row electrode 162-*r*2 and the column electrode 162-*c*2 is greater than Cm_2 of FIG. 22A due to the addition of the circular metal traces 186. Increasing the mutual capacitance enhances the detection of subtle mutual capacitance changes caused by the capacitive coupling of biological material.

Figure 29:
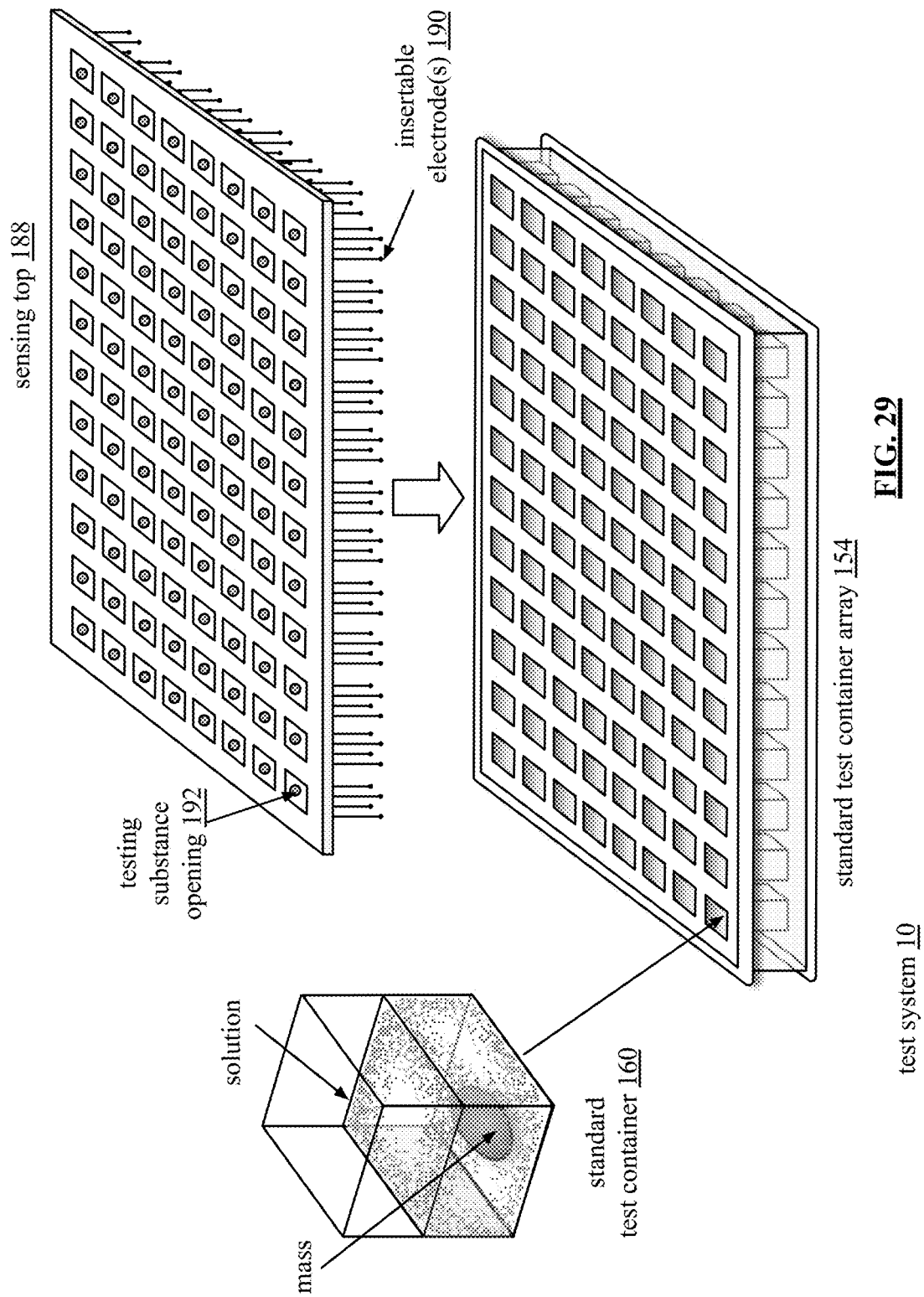
FIG. 29 is a schematic block diagram of another embodiment of a test system in accordance with the present invention.

FIG. 29 is a schematic block diagram of another embodiment of a test system 10 that includes a standard test container array 154 and a sensing top 188. The standard test container array 154 includes a plurality of standard test containers 160. The plurality of standard test containers 160 do not include electrodes. The standard test container array 154 may be comprised of a variety of materials such as polystyrene, polypropylene, glass, flexible plastic tape, and quartz, and may be a variety of shapes and sizes. The standard test container array 154 is shown as a rectangular array of 8×12 cubical standard test containers 160. The standard test container array may include more or less standard test containers 160 than shown and the standard test containers 160 may be a variety of shapes, depths, and sizes (e.g., cylindrical, rectangular prism, circular, test tube, petri dish, etc.).

The sensing top 188 includes a plurality of insertable electrodes 190 and a plurality of testing substance openings 192. The plurality of insertable electrodes 190 project outward from the sensing top 188 such that they may be placed into the tests containers of the standard test container array 154. The plurality of insertable electrodes 190 may be of various widths, lengths, and conductive materials. The plurality of insertable electrodes 190 may be disposable pieces or have a disposable coating and/or removable layer.

The plurality of insertable electrodes 190 detect electrical characteristics of biological material (e.g., cell 18) present in the standard test container array 154 when the plurality of sensing insertable 190 of the insertable sensing top 188 are placed into the standard test container array 154. With the plurality of testing substance openings 192, testing substances can be added to the standard test container array 154 without removing the insertable electrodes 190.

Figure 30:
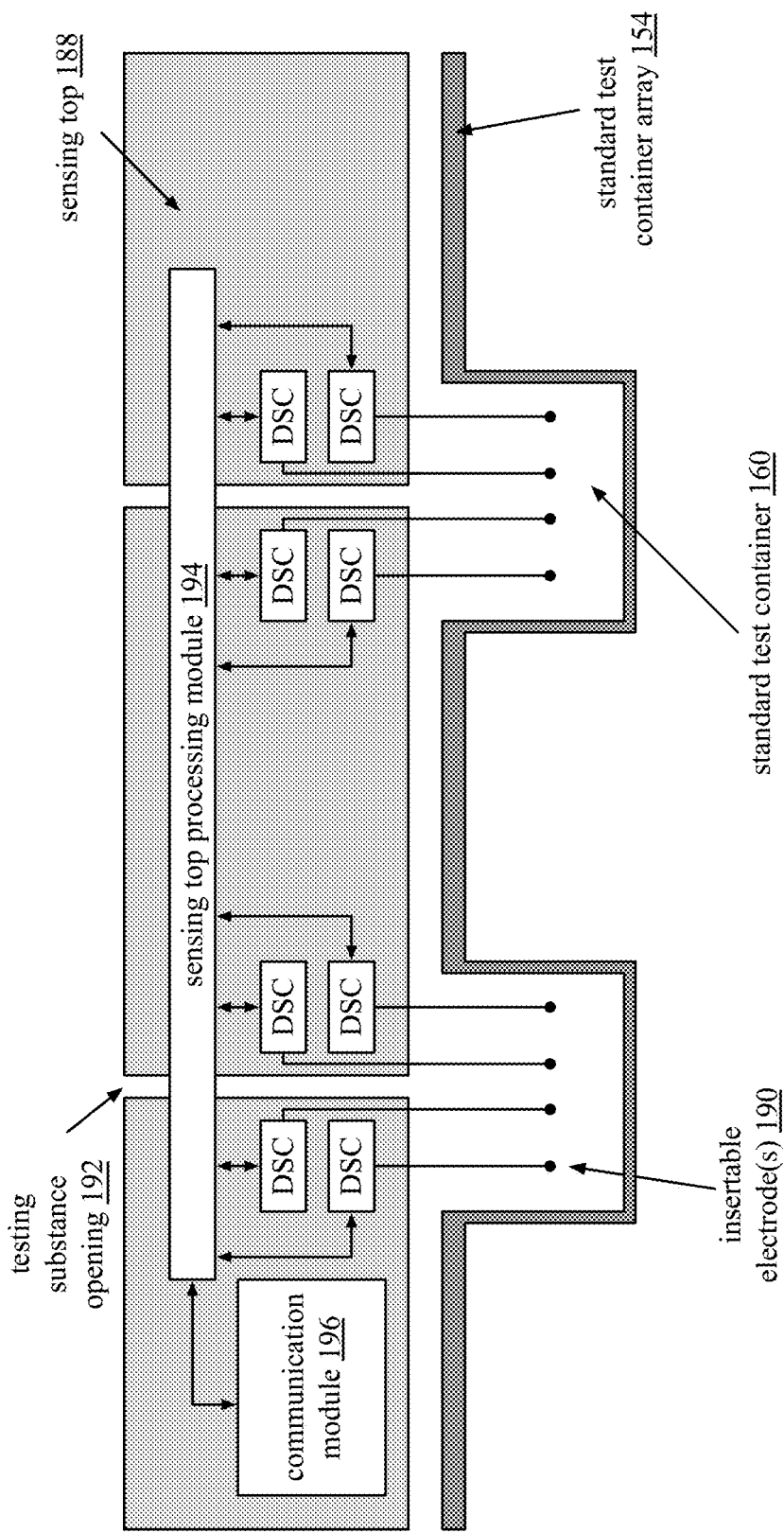
FIG. 30 is a cross section schematic block diagram of another embodiment of a test system in accordance with the present invention.

FIG. 30 is a cross section schematic block diagram of another embodiment of a test system 10 that includes a cross sectional view of a sensing top 188 resting in a standard test container array 154. The standard test container array 154 includes a plurality of standard test containers 160. The sensing top 188 includes a plurality of insertable electrodes 190, a plurality of drive-sense circuits (DSCs), a plurality of testing substance openings 192, a sensing top processing module 194, and a communication module 196. The communication module 196 is constructed in accordance with one or more wired communication protocol and/or one or more wireless communication protocols that is/are in accordance with the one or more of the Open System Interconnection (OSI) model, the Transmission Control Protocol/Internet Protocol (TCP/IP) model, and other communication protocol module.

Each insertable electrode 190 is coupled to a drive-sense circuit (DSC). The DSCs provide electrode signals to the test container electrodes 16 and detect changes in electrical characteristics of the test container electrodes. The DSCs function as described in co-pending patent application entitled, "DRIVE SENSE CIRCUIT WITH DRIVE-SENSE LINE", having a serial number of Ser. No. 16/113,379, and a filing date of Aug. 27, 2018 and in accordance with the discussion of previous Figures.

Contents of the standard test containers 160 affect the electrical characteristics of the insertable electrodes 188. In order to detect the effect of testing substances on biological material present in the standard test containers 160, the sensing top 188 includes the plurality of testing substance openings 192. With the plurality of testing substance openings 192, testing substances can be added to the standard test container array 154 without removing the electrodes 190.

The DSCs provide the detected changes in electrical characteristics of the insertable electrodes 190 to the sensing top processing module 194. The sensing top processing module 194 is described in greater detail at the end of the detailed description of the invention section and operates similarly to the processing modules of previous Figures. The sensing top processing module 194 processes the detected changes in electrical characteristics of the insertable electrodes 190 from the DSCs to determine the electrical characteristics of biological material present in the standard testing containers 160. The sensing top processing module 194 processes the detected changes in electrical characteristics of the insertable electrodes 190 from the DSCs to determine the electrical characteristics of biological material in accordance with the methods described in FIGS. 8-15.

The sensing top processing module 194 communicates the electrical characteristics of the biological material to the communication module 196. Communicating the electrical characteristics of biological material to the communication module 196 may include formatting the data in a particular format with respect to the communication protocol of the communication module. The communication module 196 is operable to communicate the electrical characteristics of cells via one or more communication protocols.

Figure 31:
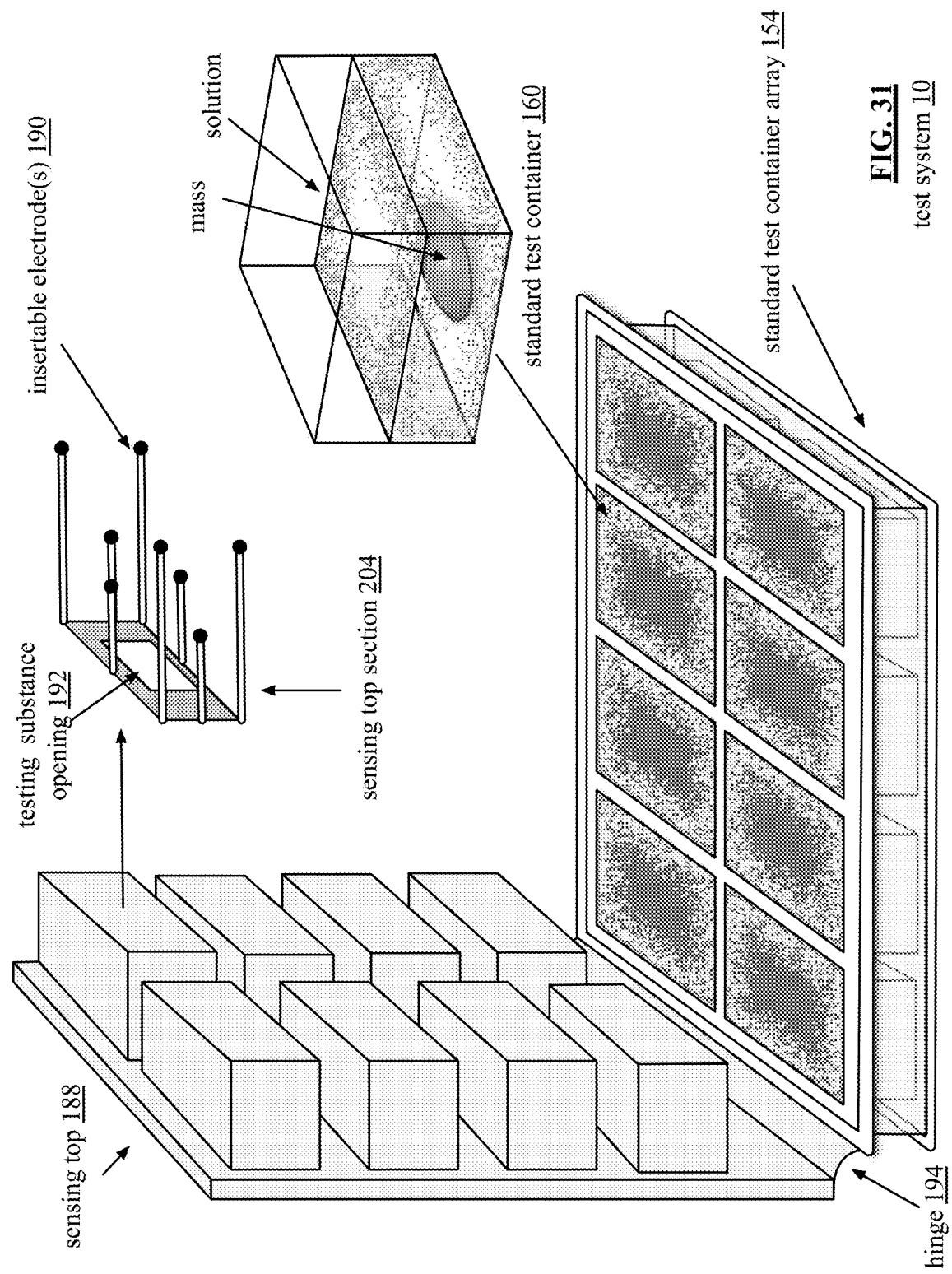
FIG. 31 is a schematic block diagram of another embodiment of a test system in accordance with the present invention.

FIG. 31 is a schematic block diagram of another embodiment of a test system 10 that includes a standard test container array 154 and a sensing top 188. The standard test container array 154 includes a plurality of standard test containers 160. The sensing top 188 includes a plurality of insertable electrodes 190 and a plurality of testing substance openings 192. The plurality of insertable electrodes 190 project outward from the sensing top 188 such that they may be placed into the standard test container array 154. The plurality insertable electrodes 190 may be of various widths, lengths, and conductive materials. The plurality of insertable electrodes 190 may be disposable pieces or have a disposable coating and/or removable layer.

A sensing top section 204 of the sensing top 188 has eight insertable electrodes 190 for inserting into a corresponding standard test container 160 of the standard test container array 154. The plurality of standard test containers 160 do not include electrodes. The standard test container array 154 is shown as a rectangular array of 2×4 cubical standard test containers 160. The standard test container array may include more or less standard test containers 160 than shown and the standard test containers 160 may be a variety of shapes, depths, and sizes (e.g., cylindrical, rectangular prism, circular, test tube, petri dish, etc.).

The test system 10 of FIG. 31 operates similarly to the test systems of FIGS. 29 and 30 except that the standard test container array 154 and the sensing top 188 are connected via a hinge 194. The plurality of sensing top electrodes 190 detect electrical characteristics of biological material (e.g., cell 18) present in the standard test container array 154 when the plurality of sensing top electrodes 190 of the insertable sensing top 188 are placed into the standard test container array 154.

Figure 32:
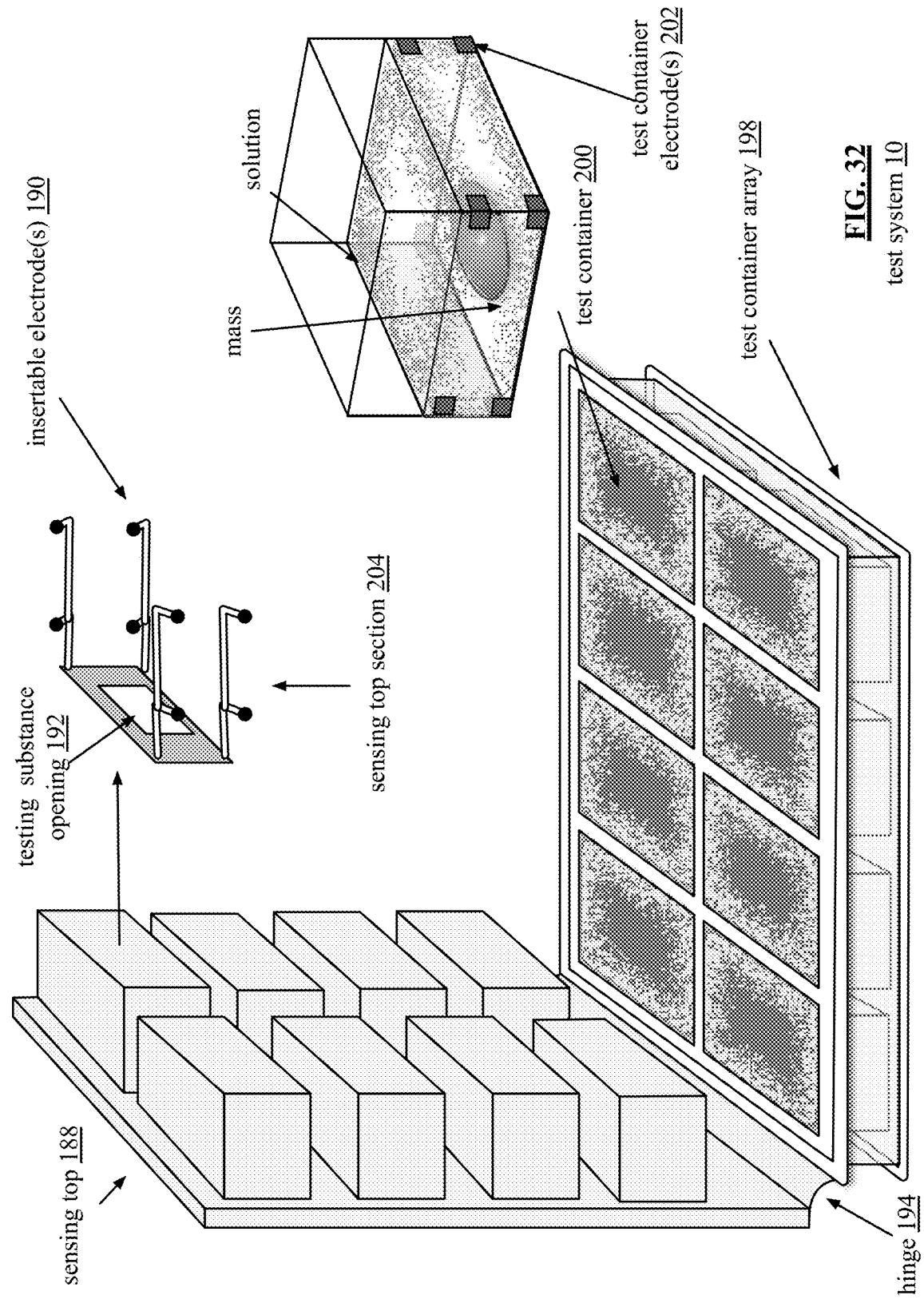
FIG. 32 is a schematic block diagram of another embodiment of a test system in accordance with the present invention.

FIG. 32 is a schematic block diagram of another embodiment of a test system 10 that includes a test container array 198 and a sensing top 188. The test container array 198 includes a plurality of test container electrodes 202. The sensing top 188 includes a plurality of testing substance openings 192 and a plurality of insertable electrodes 190 that project outward and are positioned to align with the plurality of test container electrodes 202 when inserted into the test container array 198.

A sensing top section 204 of the sensing top 188 has eight insertable electrodes 190 for inserting into a corresponding test container 200 of the test container array 198. The plurality of insertable electrodes 190 and the plurality of test container electrodes 202 may be of various shapes, widths, lengths, and conductive materials. The plurality of insertable electrodes 190 may be disposable pieces or have a disposable coating and/or removable layer. The sensing top 188 is connected to the test container array 198 by a hinge 194.

The test container electrodes 202 and the insertable electrodes 190 may be placed in a variety of positions such that the test container electrodes 202 and the insertable electrodes 190 align for electric coupling. Here, four test container electrodes 202 are shown near the bottom corners of the test container 200 and four test container electrodes 202 are below a solution 20 fill line of the test container 200. Therefore, in the sensing top section 204, four insertable electrodes 190 are shown at one length to align with the bottom four test container electrodes 202 and four insertable electrodes 190 are shown at another length to align with the solution line test container electrodes 202.

When the sensing top 188 is lowered onto the test container array 198 the plurality of insertable electrodes 190 electrically couple with the plurality of testing container electrodes 202. The coupling between the plurality of insertable electrodes 190 and the plurality of testing container electrodes 202 may be direct, capacitive, or inductive (e.g., when the electrodes are coils). When the contents (e.g., cell 18 and solution 20) of a test container 200 affect the electrical characteristics of the test container electrodes 202, the electrical characteristics of the plurality of insertable electrodes 190 are also affected due to the electric coupling.

Figure 33:
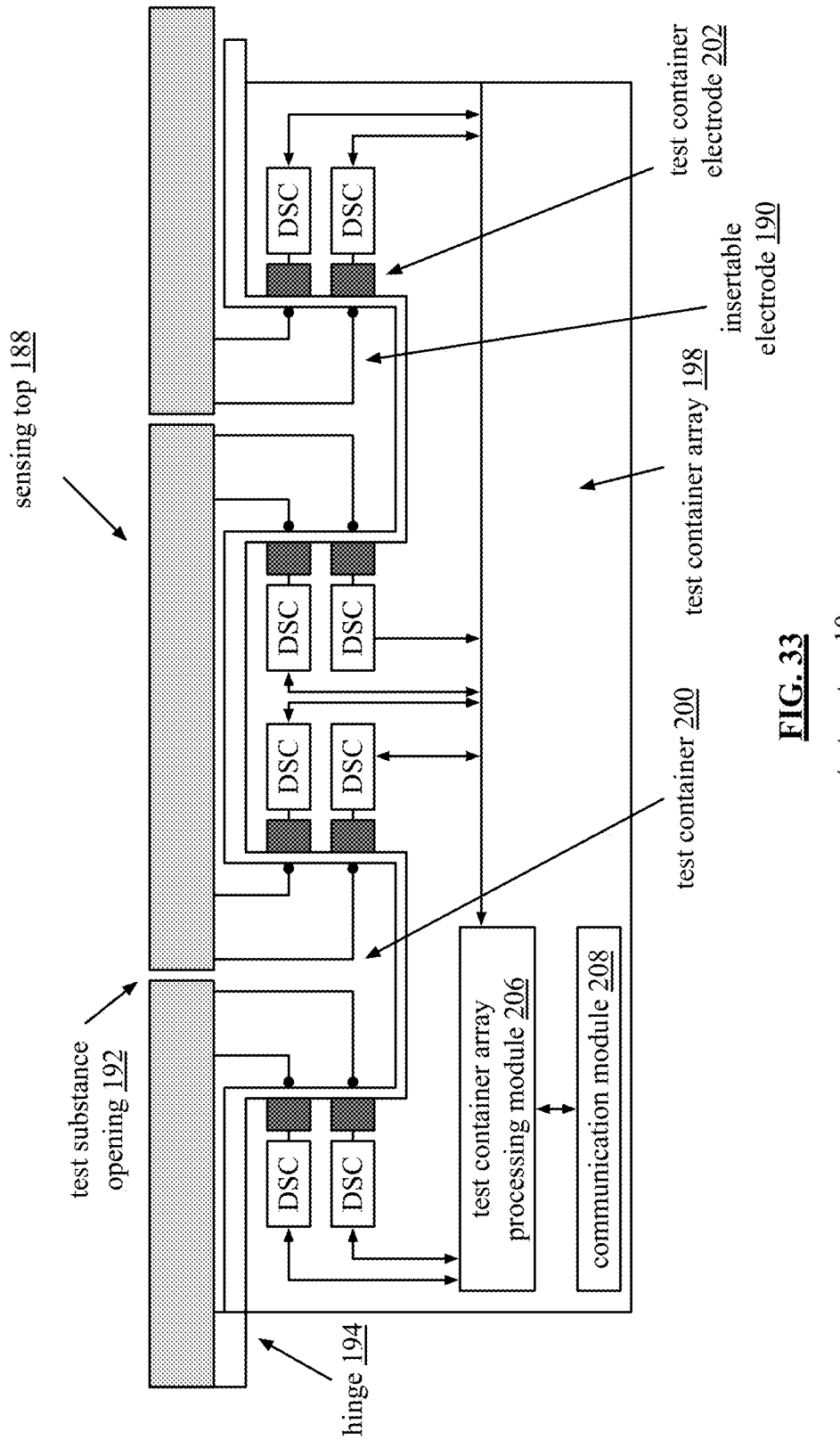
FIG. 33 is a cross section schematic block diagram of another embodiment of a test system in accordance with the present invention.

FIG. 33 is a cross section schematic block diagram of another embodiment of a test system 10 that includes a cross sectional view of a sensing top 188 resting on a test container array 198 where the sensing top 188 and test container array are connected by a hinge 194.

The sensing top 188 includes a plurality of insertable electrodes 190, and a plurality of testing substance openings 192. The test container array 198 includes a plurality of test containers 200, a plurality of test container electrodes 202, a plurality of drive-sense circuits (DSCs), a test container array processing module 206, and a communication module 208. The communication module 196 is constructed in accordance with one or more wired communication protocol and/or one or more wireless communication protocols that is/are in accordance with the one or more of the Open System Interconnection (OSI) model, the Transmission Control Protocol/Internet Protocol (TCP/IP) model, and other communication protocol module.

Each test container electrode 202 is coupled to a drive-sense circuit (DSC). The DSCs provide electrode signals to the test container electrodes 202 and detect changes in electrical characteristics of the test container electrodes. The DSCs function as described in co-pending patent application entitled, "DRIVE SENSE CIRCUIT WITH DRIVE-SENSE LINE", having a serial number of Ser. No. 16/113,379, and a filing date of Aug. 27, 2018 and in accordance with the discussion of previous Figures.

When the contents of the testing container 200 affect the electrical characteristics of the insertable electrodes 190, the electrical characteristics of the plurality of testing container electrodes 202 are also affected due to the electric coupling between the test container electrodes 202 and the plurality of insertable electrodes 190. The DSCs provide the detected changes in electrical characteristics of the test container electrodes 202 to the test container array processing module 206.

The test container array processing module 206 is described in greater detail at the end of the detailed description of the invention section and operates similarly to the processing modules of previous Figures. The test container array processing module 206 processes the detected changes in electrical characteristics of the test container electrodes 202 from the DSCs to determine the electrical characteristics of biological material present in the test containers 200. The test container array processing module 206 processes the detected changes in electrical characteristics of the test container electrodes 202 from the DSCs to determine the electrical characteristics of biological material present in accordance with the methods described in FIGS. 8-15.

The test container array processing module 206 communicates the electrical characteristics of the biological material to the communication module 208. Communicating the electrical characteristics of biological material to the communication module 208 may include formatting the data in a particular format with respect to the communication protocol of the communication module. The communication module 208 is operable to communicate the electrical characteristics of cells via one or more communication protocols.

Figure 34:
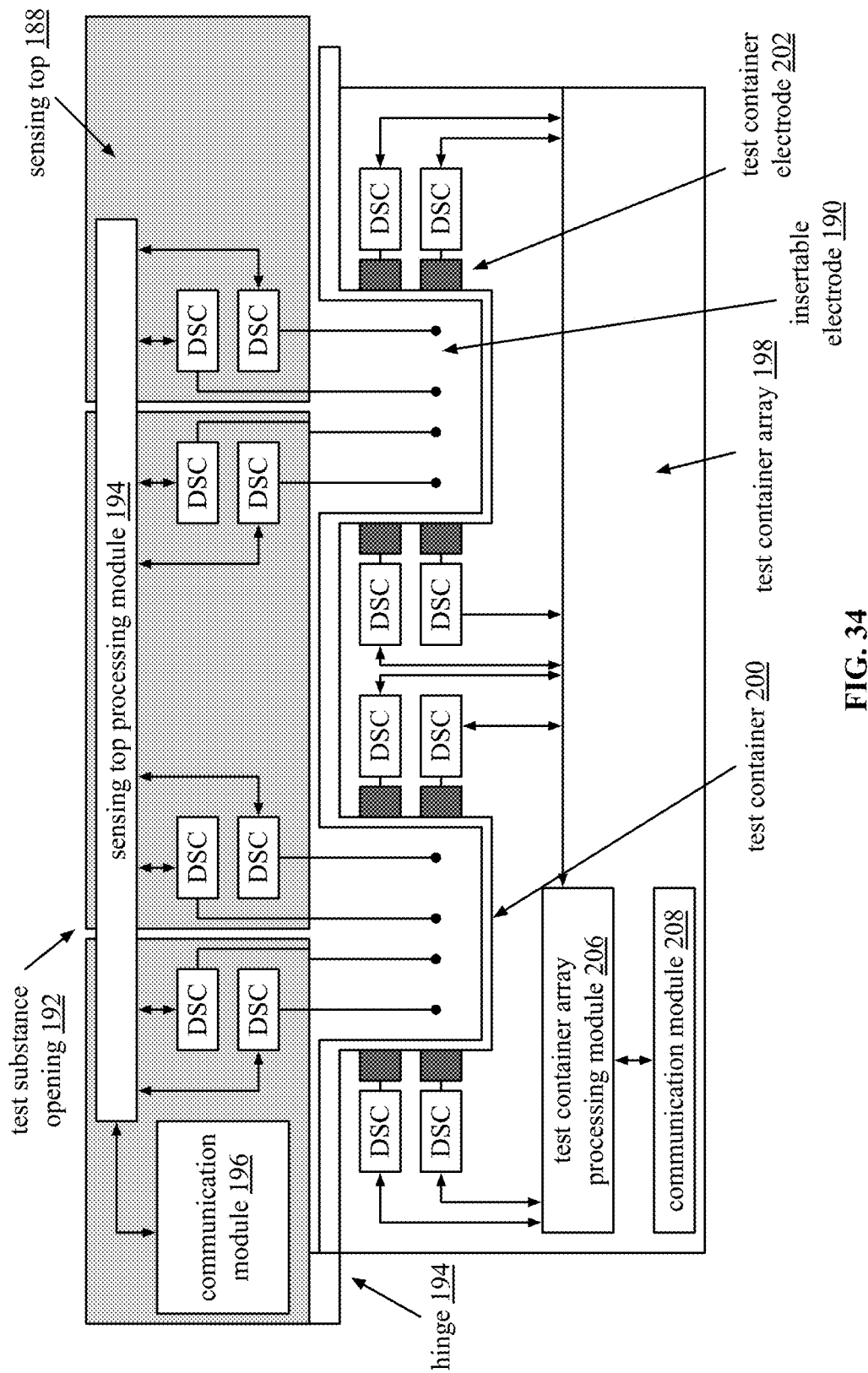
FIG. 34 is a cross section schematic block diagram of another embodiment of a test system in accordance with the present invention.

FIG. 34 is a schematic block diagram of another embodiment of the test system 10 that includes that includes a cross sectional view of a sensing top 188 resting in a test container array 198 where the sensing top 188 and test container array are connected by a hinge 194.

The sensing top 188 includes a plurality of insertable electrodes 190, a plurality of drive-sense circuits (DSCs), a plurality of testing substance openings 192, a sensing top processing module 194, and a communication module 196. The test container array 198 includes a plurality of test containers 200, a plurality of test container electrodes 202, a plurality of drive-sense circuits (DSCs), a test container array processing module 206, and a communication module

208. The communication modules 196 and 208 are constructed in accordance with one or more wired communication protocol and/or one or more wireless communication protocols that is/are in accordance with the one or more of the Open System Interconnection (OSI) model, the Transmission Control Protocol/Internet Protocol (TCP/IP) model, and other communication protocol module.

The sensing top processing module 194 and the test container array processing module 206 may be the same or different processing modules and may be located in the sensing top, the test container array, or both. The communication modules 196 and 208 may be the same or different communication modules and may be located in the sensing top, the test container array or both.

Each insertable electrode 190 and each test container electrode 202 is coupled to a drive-sense circuit (DSC). The DSCs of the sensing top 188 provide electrode signals to the test insertable electrodes 190 and detect changes in electrical characteristics of insertable electrodes 190. The DSCs of the test container array 198 provide electrode signals to the test container electrodes 202 and detect changes in electrical characteristics of the test container electrodes 202. The DSCs function as described in co-pending patent application entitled, "DRIVE SENSE CIRCUIT WITH DRIVE-SENSE LINE", having a serial number of Ser. No. 16/113,379, and a filing date of Aug. 27, 2018 and in accordance with the discussion of previous Figures.

Contents of the test containers 200 affect the electrical characteristics of both the insertable electrodes 190 and the test container electrodes 202. The DSCs of the sensing top 188 provide the detected changes in electrical characteristics of the insertable electrodes 190 to the sensing top processing module 194. The DSCs of the test container array 198 provide the detected changes in electrical characteristics of the test container electrodes 202 to the test container array processing module 206.

The test container array processing module 206 and the sensing top processing module 194 are described in greater detail at the end of the detailed description of the invention section and operate similarly to the processing modules of previous Figures. The sensing top processing module 194 processes the detected changes in electrical characteristics of the insertable electrodes 190 from the DSCs to determine first electrical characteristics of biological material present in the standard testing containers 160.

For example, the first electrical characteristics of biological material present in the standard testing containers 160 are measurements from the interior of the test containers 200. The test container array processing module 206 processes the detected changes in electrical characteristics of the test container electrodes 202 from the DSCs to determine second electrical characteristics of biological material present in the test containers 200. The second electrical characteristics of biological material present in the test containers 200 are regarding measurements from the perimeter of the test containers 200.

The sensing top processing module 194 communicates the first electrical characteristics of the biological material to the communication module 196. Communicating the first electrical characteristics of biological material to the communication module 196 may include formatting the data in a particular format with respect to the communication protocol of the communication module. The communication module 196 is operable to communicate the first electrical characteristics of cells via one or more communication protocols.

The test container array processing module 206 communicates the second electrical characteristics of the biological material to the communication module 208. Communicating the second electrical characteristics of biological material to the communication module 208 may include formatting the data in a particular format with respect to the communication protocol of the communication module. The communication module 208 is operable to communicate the second electrical characteristics of cells via one or more communication protocols.

It is noted that terminologies as may be used herein such as bit stream, stream, signal sequence, etc. (or their equivalents) have been used interchangeably to describe digital information whose content corresponds to any of a number of desired types (e.g., data, video, speech, text, graphics, audio, etc. any of which may generally be referred to as 'data').

As may be used herein, the terms "substantially" and "approximately" provide an industry-accepted tolerance for its corresponding term and/or relativity between items. For some industries, an industry-accepted tolerance is less than one percent and, for other industries, the industry-accepted tolerance is 10 percent or more. Other examples of industry-accepted tolerance range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances may be more or less than a percentage level (e.g., dimension tolerance of less than +/−1%). Some relativity between items may range from a difference of less than a percentage level to a few percent. Other relativity between items may range from a difference of a few percent to magnitude of differences.

As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to".

As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may be used herein, one or more claims may include, in a specific form of this generic form, the phrase "at least one of a, b, and c" or of this generic form "at least one of a, b, or c", with more or less elements than "a", "b", and "c". In either phrasing, the phrases are to be interpreted identically. In particular, "at least one of a, b, and c" is equivalent to "at least one of a, b, or c" and shall mean a, b, and/or c. As an example, it means: "a" only, "b" only, "c" only, "a" and "b", "a" and "c", "b" and "c", and/or "a", "b", and "c".

As may also be used herein, the terms "processing module", "processing circuit", "processor", "processing circuitry", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, processing circuitry, and/or processing unit may be, or further include, memory and/or an integrated memory element, which may be a single memory device, a plurality of memory devices, and/or embedded circuitry of another processing module, module, processing circuit, processing circuitry, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, processing circuitry, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, processing circuitry and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, processing circuitry and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with one or more other routines. In addition, a flow diagram may include an "end" and/or "continue" indication. The "end" and/or "continue" indications reflect that the steps presented can end as described and shown or optionally be incorporated in or otherwise used in conjunction with one or more other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While the transistors in the above described figure(s) is/are shown as field effect transistors (FETs), as one of ordinary skill in the art will appreciate, the transistors may be implemented using any type of transistor structure including, but not limited to, bipolar, metal oxide semiconductor field effect transistors (MOSFET), N-well transistors, P-well transistors, enhancement mode, depletion mode, and zero voltage threshold (VT) transistors.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid-state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A test system comprises:
a test container array including a plurality of test containers;
a plurality of electrodes integrated into the test container array, wherein a set of electrodes of the plurality of electrodes is integrated into a test container of the test container array;
a plurality of drive-sense circuits coupled to the plurality of electrodes, wherein a set of drive-sense circuits of the plurality of drive-sense circuits is coupled to the set of electrodes, wherein an electrode of the set of electrodes is coupled to a drive-sense circuit of the set of the drive-sense circuits via a single line and wherein the drive-sense circuit is operable to simultaneously both drive and detect a change in electrical characteristics of the electrode via the single line;
a processing module operably coupled to:
receive, from the set of drive-sense circuits, a set of changes in electrical characteristics of the set of electrodes; and
interpret the set of changes in electrical characteristics of the set of electrodes as a set of impedance values representative of electrical characteristics of biological material present in the test container; and
a communication module operably coupled to communicate the electrical characteristics of the biological material.

2. The test system of claim 1, wherein the biological material comprises one or more of:
one or more biological cells; and
a portion of one or more biological cells.

3. The test system of claim 1, wherein the electrical characteristics of the biological material include one or more of:
position;
impedance;
size;
shape;
movement;
density;
excitability; and
potential.

4. The test system of claim 1, wherein the processing module is operable to interpret the set of changes in electrical characteristics as the set of impedance values by:
receiving, from the set of drive-sense circuits, the set of changes in electrical characteristics from the set of electrodes;
filtering the set of changes in electrical characteristics in accordance with a set of bandpass frequency ranges to produce a set of filtered signals; and
interpreting the set of filtered signals to identify the set of impedance values representative of the electrical characteristics of the biological material.

5. The test system of claim 1 further comprises:
a plurality of multiplexors coupled to the plurality of drive-sense circuits and the plurality of electrodes, wherein a first multiplexor of the plurality of multiplexors is coupled to a first drive sense-circuit of the plurality of drive-sense circuits and the set of electrodes; and
the processing module is further operable to:
generate a plurality of multiplexor control signals for selecting electrodes of the plurality of electrodes for sensing via the plurality of drive-sense circuits, wherein a first multiplexor control signal of the plurality of multiplexor control signals selects a first electrode of the set of electrodes for sensing via the first drive-sense circuit.

6. A test system comprises:
a test container array including a plurality of test containers;
a plurality of electrodes integrated into the test container array, wherein a set of electrodes of the plurality of electrodes is integrated into a test container of the test container array;
a plurality of drive-sense circuits coupled to the plurality of electrodes, wherein a set of drive-sense circuits of the plurality of drive-sense circuits is coupled to the set of electrodes, wherein an electrode of the set of electrodes are coupled to a drive-sense circuit of the set of the drive-sense circuits via a single line, wherein the drive-sense circuit is operable to simultaneously both drive and detect a change in electrical characteristics of the electrode via the single line, and wherein the change in the electrical characteristics are representative of electrical characteristics of biological material present in the test container; and
a communication module operably coupled to communicate the electrical characteristics of the electrode.

7. The test system of claim 6 further comprises:
a processing module operably coupled to:
receive, from the set of drive-sense circuits, a set of changes in electrical characteristics of the set of electrodes; and
interpret the set of changes in electrical characteristics of the set of electrodes as a set of impedance values representative of electrical characteristics of the biological material present in the test container.

8. The test system of claim 7, wherein the processing module is operable to interpret the set of changes in electrical characteristics as the set of impedance values by:
receiving, from the set of drive-sense circuits, the set of changes in electrical characteristics from the set of electrodes;

filtering the set of changes in electrical characteristics in accordance with a set of bandpass frequency ranges to produce a set of filtered signals; and interpreting the set of filtered signals to identify the set of impedance values representative of the electrical characteristics of the biological material.

9. The test system of claim 7 further comprises:

a plurality of multiplexors coupled to the plurality of drive-sense circuits and the plurality of electrodes, wherein a first multiplexor of the plurality of multiplexors is coupled to a first drive sense-circuit of the plurality of drive-sense circuits and the set of electrodes; and the processing module is further operable to:

generate a plurality of multiplexor control signals for selecting electrodes of the plurality of electrodes for sensing via the plurality of drive-sense circuits, wherein a first multiplexor control signal of the plurality of multiplexor control signals selects a first electrode of the set of electrodes for sensing via the first drive-sense circuit.

10. The test system of claim 6, wherein the biological material comprises one or more of:

one or more biological cells; and a portion of one or more biological cells.

11. The test system of claim 6, wherein the electrical characteristics of the biological material include one or more of:

position;
impedance;
size;
shape;
movement;
density;
excitability; and
potential.

* * * * *